United States Patent
Rubbert et al.

(10) Patent No.: US 7,197,179 B2
(45) Date of Patent: Mar. 27, 2007

(54) METHODS FOR REGISTRATION OF THREE-DIMENSIONAL FRAMES TO CREATE THREE-DIMENSIONAL VIRTUAL MODELS OF OBJECTS

(75) Inventors: Rüdger Rubbert, Berlin (DE); Thomas Weise, Berlin (DE); Peer Sporbert, Berlin (DE); Hans Imgrund, Berlin (DE); Dimitrij Kouzian, Berlin (DE)

(73) Assignee: OraMetrix, Inc., Richardson, TX (US)

( * ) Notice: Subject to any disclaimer, the term of this patent is extended or adjusted under 35 U.S.C. 154(b) by 352 days.

(21) Appl. No.: 10/953,240

(22) Filed: Sep. 29, 2004

(65) Prior Publication Data
US 2005/0069188 A1  Mar. 31, 2005

Related U.S. Application Data

(60) Division of application No. 09/835,007, filed on Apr. 13, 2001, now Pat. No. 7,027,642, and a continuation-in-part of application No. 09/560,645, filed on Apr. 28, 2000, now Pat. No. 6,728,423, and a continuation-in-part of application No. 09/560,644, filed on Apr. 28, 2000, now Pat. No. 6,413,084, and a continuation-in-part of application No. 09/560,584, filed on Apr. 28, 2000, now Pat. No. 7,068,836, and a continuation-in-part of application No. 09/560,583, filed on Apr. 28, 2000, now Pat. No. 6,738,508, and a continuation-in-part of application No. 09/560,132, filed on Apr. 28, 2000, now Pat. No. 6,771,809, which is a continuation-in-part of application No. 09/560,131, filed on Apr. 28, 2000, now Pat. No. 6,744,914.

(51) Int. Cl.
*G06K 9/00* (2006.01)
*G06K 15/00* (2006.01)

(52) U.S. Cl. .................... 382/154; 382/285; 348/42; 345/419; 356/12

(58) Field of Classification Search ............... 382/154, 382/285; 345/419–427; 356/12–14; 348/42–60; 359/462–477; 352/57–65; 33/20.4; 353/7–9; 378/41–42; 396/324–331
See application file for complete search history.

(56) References Cited

U.S. PATENT DOCUMENTS 5,257,203 A * 10/1993 Riley et al. ............... 700/163

(Continued)

*Primary Examiner*—Jingge Wu
*Assistant Examiner*—Aaron Carter
(74) *Attorney, Agent, or Firm*—McDonnell, Boehnen, Hulbert & Berghoff LLP

(57) ABSTRACT

A method and system are provided for constructing a virtual three-dimensional model of an object using a data processing system, and at least one machine-readable memory accessible to said data processing system. A set of at least two digital three-dimensional frames of portions of the object are obtained from a source, such as a computing system coupled to an optical or laser scanner, CT scanner, Magnetic Resonance Tomography scanner or other source. The at least two frames comprise a set of point coordinates in a three dimensional coordinate system providing differing information of the surface of the object. The frames provide a substantial overlap of the represented portions of the surface of the object, but do not coincide exactly for example due to movement of the scanning device relative to the object between the generation of the frame. Data representing the set of frames are stored in the memory. The data processing system processes the data representing the set of frames with said data processing system so as to register the frames relative to each other to thereby produce a three-dimensional virtual representation of the portion of the surface of the object covered by said set of frames. The registration is performed without using pre-knowledge about the spatial relationship between the frames. The three-dimensional virtual model or representation is substantially consistent with all of the frames.

12 Claims, 51 Drawing Sheets

U.S. PATENT DOCUMENTS

| | | | |
|---|---|---|---|
| 5,649,032 A * | 7/1997 | Burt et al. | 382/284 |
| 6,078,701 A * | 6/2000 | Hsu et al. | 382/294 |
| 6,476,803 B1 * | 11/2002 | Zhang et al. | 345/419 |
| 6,621,491 B1 * | 9/2003 | Baumrind et al. | 345/419 |
| 2001/0043738 A1 * | 11/2001 | Sawhney et al. | 382/154 |
| 2003/0039389 A1 * | 2/2003 | Jones et al. | 382/154 |
| 2003/0169913 A1 * | 9/2003 | Kopelman et al. | 382/132 |

* cited by examiner

PIXEL COORDINATES FOR PORTIONS OF THE PATTERN ASSIGNED TO A CERTAIN Z-LEVEL

FIG. 24

CCD$_X$, CCD$_Y$ = PIXEL #, IN SUBPIXEL RESOLUTION

CALIBRATION TABLE #1 (BEFORE)

| | | ROW 1 | ROW 2 | ROW 3 | ROW 4 | ... | ROW M | ROW 1 | ROW 2 | ROW 3 | ROW 4 | ... | ROW M | ... | ROW 1 | ROW 2 | ... | ROW M |
|---|---|---|---|---|---|---|---|---|---|---|---|---|---|---|---|---|---|---|
| | | \multicolumn{6}{c}{LINE 1} | \multicolumn{6}{c}{LINE 2} | | \multicolumn{4}{c}{LINE N} |
| $z_1$ | CCD$_X$ | 1.0 | 1.1 | 1.5 | 2.1 | | | 27.1 | 29.5 | 30.2 | 37.1 | | | | | | | |
| | MM DIST. | | | | | | | | | | | | | | | | | |
| | CCD$_Y$ | 10.2 | 20.4 | 32.8 | 44.5 | | | | 21.6 | 36.2 | 44 | | | | | | | |
| | MM DIST. | | | | | | | | | | | | | | | | | |
| $z_2$ | CCD$_X$ | 3.9 | 4.5 | 6.8 | 12.2 | | | 34.0 | 41.1 | 43.0 | 46 | | | | | | | |
| | MM DIST. | | | | | | | | | | | | | | | | | |
| | CCD$_Y$ | 12.1 | 21.5 | 30.4 | 46.3 | | | 13.2 | 21.8 | 31.0 | 48.2 | | | | | | | |
| | MM DIST. | | | | | | | | | | | | | | | | | |

FIG. 25

CALIBRATION TABLE #2 (Q,P)

QUADRANT I

|  |  | (0,0) | (1,0) | (2,0) | (3,0) | ... | ROW 0 (Q/2 - ΔQ,0) | ... | (Q/2,0) | ROW 1 (0,1) | (1,1) | (2,1) | ... | (Q,P) | ... | (0, P/2) | ROW + P/2 (1, P/2) | ... | (Q/2, P/2) |
|---|---|---|---|---|---|---|---|---|---|---|---|---|---|---|---|---|---|---|---|
| $z_1$ | CCDx | 640.1 | 700.2 | 760.6 | 820.5 | ... | ... | ... | — | 640.1 | 700.2 | ... | ... | ... | ... | ... | ... | 1,279.5 |
| | CCDy | 640.1 | 640.1 | 640.3 | 640.4 | ... | ... | ... | — | 701.2 | 701.5 | ... | ... | ... | ... | ... | ... | 1,279.4 |
| $z_2$ | CCDx | 640.2 | 680.3 | 741.2 | 801.6 | ... | ... | ... | 1,279.5 | ... | 681.2 | ... | ... | ... | ... | ... | ... | 1,256.4 |
| | CCDy | 640.2 | 640.3 | 640.1 | 640.1 | ... | ... | ... | 640.2 | ... | 680.9 | ... | ... | ... | ... | ... | ... | 1,251.5 |

QUADRANT II

|  |  | (-1,0) | (-2,0) | (-3,0) | (-4,0) | ... | ROW (-Q/2 - ΔQ,0) | ... | (-Q/2,0) | ROW 1 (-1,1) | (-2,1) | (-3,1) | ... | ... | ... | (-1, P/2) | ROW +P/2 (-2, P/2) | ... | (-Q/2, P/2) |
|---|---|---|---|---|---|---|---|---|---|---|---|---|---|---|---|---|---|---|---|
| $z_1$ | CCDx | | | | | | | | | | | | | | | | | | |
| | CCDy | | | | | | | | | | | | | | | | | | |
| $z_2$ | CCDx | | | | | | | | | | | | | | | | | | |
| | CCDy | | | | | | | | | | | | | | | | | | |

QUADRANT III

|  |  | (-1,-1) | (-2,-1) | ... |
|---|---|---|---|---|
| $z_1$ | CCDx | | | |
| | CCDy | | | |
| $z_2$ | CCDx | | | |
| | CCDy | | | |

QUADRANT IV

|  |  | (0,-1) | (1,-1) | ... |
|---|---|---|---|---|
| $z_1$ | CCDx | | | |
| | CCDy | | | |
| $z_2$ | CCDx | | | |
| | CCDy | | | |

FIG. 26

CCDx, CCDy = PIXEL #, IN SUBPIXEL RESOLUTION

CALIBRATION TABLE #1 (AFTER)

| | PATTERN LINE 1 | | | | | PATTERN LINE 2 | | | | | | LINE N | | | |
|---|---|---|---|---|---|---|---|---|---|---|---|---|---|---|---|
| | ROW 1 | ROW 2 | ROW 3 | ROW 4 | ... | ROW M | ROW 1 | ROW 2 | ROW 3 | ROW 4 | ... | ROW M | ROW 1 | ROW 2 | ... | ROW M |
| $z_1$ CCDx | 1.0 | 1.1 | 1.5 | 2.1 | | ... | 27.1 | 29.5 | 30.2 | 37.1 | | | | | | |
| $z_1$ MM DIST | | | | | | | | | -14.6 | | | | | | | |
| $z_1$ CCDy | 10.2 | 20.4 | 32.8 | 44.5 | | | 11.5 | 21.6 | 36.2 | 44 | | | | | | |
| $z_1$ MM DIST | | | | | | | | | -14.4 | | | | | | | |
| $z_2$ CCDx | 3.9 | 4.5 | 6.8 | 12.2 | | | 34.0 | 41.1 | 43.0 | 46 | | | | | | |
| $z_2$ MM DIST | | | | | | | | | -14.8 | | | | | | | |
| $z_2$ CCDy | 12.1 | 21.5 | 30.4 | 46.3 | | | 13.2 | 21.8 | 31.0 | 48.2 | | | | | | |
| $z_2$ MM DIST | | | | | | | | | -15.8 | | | | | | | |

L = 1.0 mm

△ = POINTS OF FRAME i
+ = POINTS OF FRAME i + 1
o = POINTS OF FRAME i + 2

FRAME i

FRAME i + 1

SUM OF NORMAL VECTORS 254

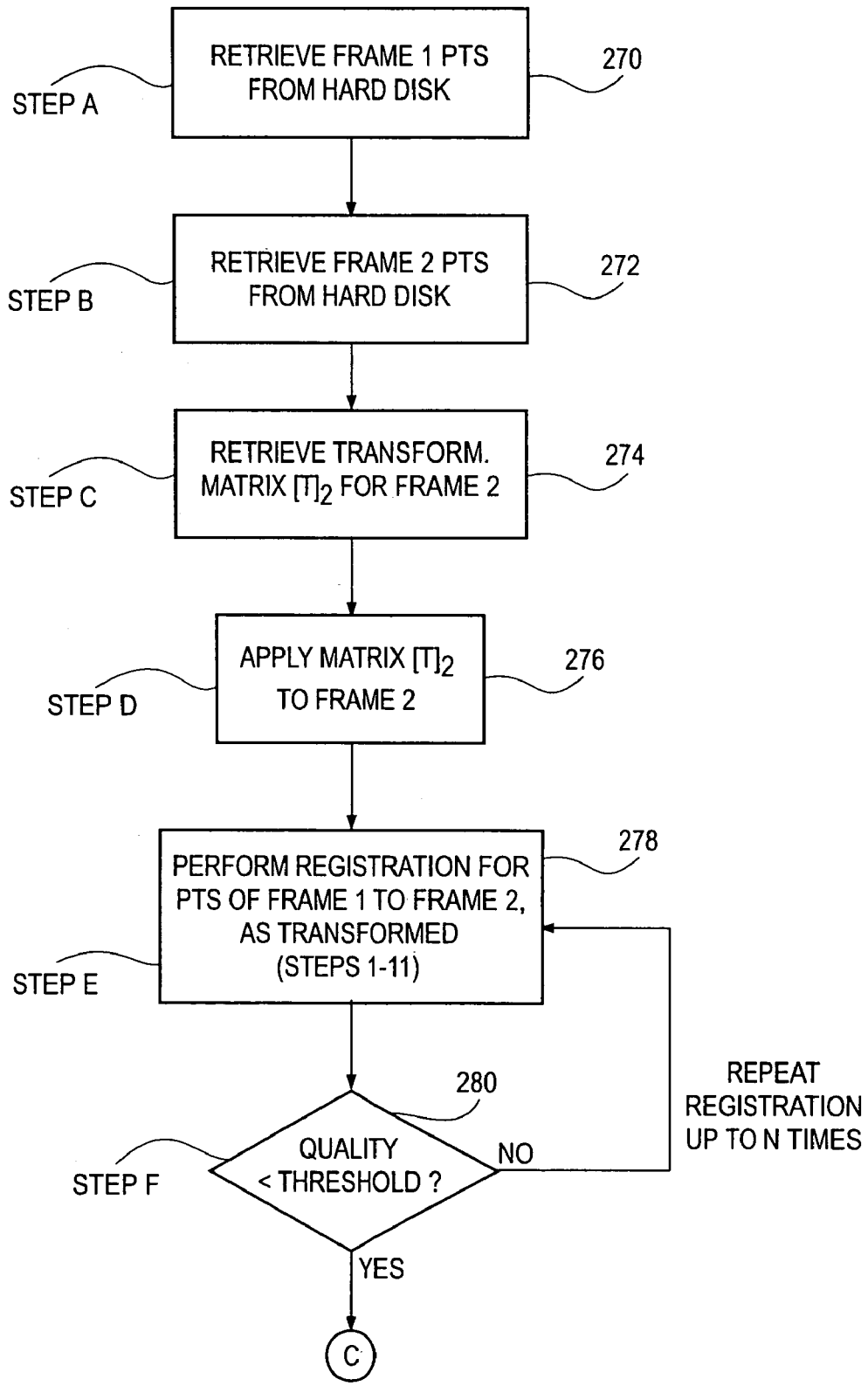

FIG. 54

○ Single
○ Cumulative

| X | Y | Z |
|---|---|---|
| 0.00 | 0.00 | 0.00 |
| 3.00 | 0.00 | 0.00 |
| -3.00 | 0.00 | 0.00 |
| 0.00 | 3.00 | 0.00 |
| 0.00 | -3.00 | 0.00 |

Registration (raw)
- Distance limit (SYX): 250.00y
- Stationary count: 5
- Radius (SYX): 2.000mm
- Convergence factor: 0.100
- Number of points to register: 400
- Accelerate factor: 1.6

Registration (raw + fine)
- Maximal iteration count: 400
- Overlap size: 6.000
- Minimum quote of active points (0..1): 0.200
- Maximal triangle size (larger triangles are treated as gaps): 0.500
- Maximal edge length (longer edges have no attraction): 1.800mm
- Maximal count of unsuccessful files new segment is started when exceeded: 2
- Form factor: Proportion of point distance and element size (>=0): 0.1

Registration (line)
- Distance limit (SYX): 50.000y
- Final distance: 40.000y
- Stationary count: 10
- Radius (SYX): 0.500mm
- Convergence factor: 0.010
- Number of points to register: 400
- Accelerate factor: 1.3

☑ Combine frames cumulative
☑ Combine segments cumulative general
- Count of SYX surfaces for animation (0= off): 20
- Cell size: 16

Merging
- Radius of sphere inside which is to replace: 0.500mm
- Minimal triangle plane size for closing gaps: 0.010
- Minimal distance from point of base quantity: 0.400mm
- Maximal count of edge lines for closing gaps: 16
- Maximal edge length for closing gaps: 1.500mm
- Maximal distance from edge of base quantity: 0.000mm 0.00    0.00    0.00    0.00

308 302

310

308
310

312

METHODS FOR REGISTRATION OF THREE-DIMENSIONAL FRAMES TO CREATE THREE-DIMENSIONAL VIRTUAL MODELS OF OBJECTS

CROSS-REFERENCE TO RELATED APPLICATIONS

This application is a divisional application of the pending U.S. patent application Ser. No. 09/835,007 filed Apr. 13, 2001 now U.S. Pat. No. 7,027,642 which is a continuation-in-part application of the following U.S. Patent applications:

Ser. No. 09/560,131 filed Apr. 28, 2000, now issued as U.S. Pat. No. 6,744,914;

Ser. No. 09/560,132 filed Apr. 28, 2000, now issued as U.S. Pat. No. 6,771,809;

Ser. No. 09/560,583 filed Apr. 28, 2000, now issued as U.S. Pat. No. 6,738,508;

Ser. No. 09/560,645 filed Apr. 28, 2000, now issued as U.S. Pat. No. 6,728,423;

Ser. No. 09/560,644 filed Apr. 28, 2000, now issued as U.S. Pat. No. 6,413,084;

Ser. No. 09/560,584 filed Apr. 28, 2000, now U.S. Pat. No. 7,068,836.

The entire contents of each of the above patent applications is incorporated by reference herein.

BACKGROUND OF THE INVENTION

A. Field of the Invention

This invention relates generally to systems and methods for generating three-dimensional virtual models of objects using a data processing system such as a general purpose computer.

B. Description of Related Art

Scanners are devices for capturing and recording information from a surface of an object. Scanners for obtaining information from a two-dimensional surface, such as reading bar codes or characters printed on a piece of paper, are widely known. Several scanners have been proposed for recording three-dimensional information as well.

Dentistry and orthodontics is one area where precise knowledge of a patient's dentition is desirable, and hence this is one area where three-dimensional scanners have been proposed. The key to efficiency in treatment and maximum quality in results is a realistic simulation of the treatment process. Today's orthodontists have the possibility of taking plaster models of the upper and lower jaw, cutting the cast into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. To make sure that the brackets will be bonded at exactly this position at the real patient's teeth, small templates for every tooth would have to be fabricated that fit over the bracket and a relevant part of the tooth and allow for reliable placement of the bracket at the patient. To increase efficiency of the bonding process, another option would be to transfer each single bracket onto a model of the malocclusion and then fabricate one single transfer tray per jaw that covers all brackets and relevant portions of every tooth. Using such a transfer tray guarantees a very quick and yet precise bonding.

However, it is obvious that such an approach requires an extreme amount of time and labor, and this is the reason why it is limited to scientific environments like orthodontic schools and universities. The normal orthodontist does not fabricate set-ups; he places the brackets directly at the patient to the best of his knowledge, uses an off-the-shelf wire and hopes for the best. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 4,837,732 and U.S. Pat. No. 4,575,805 to Brandestini and Moermann propose a scanning system for in vivo, non-contact scanning of teeth. The patents describe a procedure for optically mapping a prepared tooth with a non-contact scan-head. The scan-head delivers the contour data, converted to electrical format, to be stored in a memory. A computer reads the memory following a line scan pattern. A milling device is slaved to follow this pattern by means of position control signals and mills an implant for the prepared tooth cavity.

The scan-head of the '732 and '805 patents includes a light emitting diode, with integral lens that radiates light onto the cavity. Before reaching the object, the rays of light are reflected by a mirror and pass through a ruling consisting of a plurality of parallel slits, or an alternating pattern of parallel opaque and transparent stripes. The reflected light is focused by a lens onto a charge-coupled device (CCD) sensor. Depth information is determined in accordance with a principle known as "active triangulation," using parameters shown in FIG. 9 of this document and described subsequently. Basically, the object is viewed under an angle different from the incident rays due to a parallax effect. Each light stripe will have an apparent positional shift and the amount of the shift at each point along each light stripe is proportional to the vertical height of the corresponding portion of the surface on the object.

U.S. Pat. No. 5,372,502 to Massen et al. describes an optical probe for measuring teeth that works on the similar principle. As noted in the Massen et al. patent, the Brandestini et al. technique is difficult to use when there are large variations in surface topography since such large jumps displace the pattern by an amount larger than the phase constant of the pattern, making it difficult to reconstruct the pattern of lines. Furthermore, precise knowledge of the angle of incidence and angle of reflection, and the separation distance between the light source and the detector, are needed to make accurate determinations of depth.

U.S. Pat. No. 5,027,281 to Rekow et al. describes a scanning method by which a digitized comprising a three axis positioning head with a laser source and detector, a rotational stage and a computer controller. The computer controller positions both the rotational stage and the positioning head. An object is placed on the rotational stage and the laser beam reflects from it. The reflected laser beam is used to measure the distance between the object and the laser source. X and Y coordinates are obtained by movement of the rotational stage or the positioning head. A three-dimensional virtual model of the object is created from the laser scanning. The '281 patent describes using this scanning method for scanning a plaster model of teeth for purposes of acquiring shape of the teeth to form a dental prosthesis. The system of the '281 patent is not particularly flexible, since it requires the object to be placed on the rotational stage and precise control of the relative position of the object and the positioning head is required at all times. It is unsuited for in vivo scanning of the teeth.

U.S. Pat. No. 5,431,562 to Andreiko et al. describes a method of acquiring certain shape information of teeth from a plaster model of the teeth. The plaster model is placed on a table and a picture is taken of the teeth using a video camera positioned a known distance away from the model, looking directly down on the model. The image is displayed on an input computer and a positioning grid is placed over the image of the teeth. The operator manually inputs X and Y coordinate information of selected points on the teeth, such as the mesial and distal contact points of the teeth. An alternative embodiment is described in which a laser directs a laser beam onto a model of the teeth and the reflected beam is detected by a sensor. The patent asserts that three-dimensional information as to teeth can be acquired from this technique but does not explain how it would be done. Neither of the techniques of Andreiko have met with commercial success or acceptance in orthodontics. Neither technique achieves in vivo scanning of teeth. Moreover, the video technique does not produce complete three-dimensional information as to the teeth, but rather a limited amount of two-dimensional information, requiring significant operator input. Even using this technique, additional equipment is required even to describe the labial surface of a tooth along a single plane.

The above-cited patents do not teach or suggest a method by which overlapping three-dimensional point clouds of data can be registered to each other to generate a consistent representation of the object, without pre-knowledge of the spatial relationship between the frames, such as may occur with hand-held scanning of an object where the distance or spatial relationship of the scanner to the object is not known in advance. For example, if the scanner of the Brandestini et al. patents were to be used by hand to obtain overlapping images, the patent does not teach how the two overlapping images could be reconciled with each other to generate a consistent three-dimensional representation of the object. The present invention solves this problem.

In accordance with the present invention, highly accurate virtual models of objects are generated from a set of "frames", each of which contain three dimensional surface information of the object either in terms of a point cloud or a collection of surface segments. The frames can be derived from two-dimensional image data taken from an optical scanner (e.g., a hand-held optical scanner) using techniques described herein, or the frames can be obtained from some other type of scanning device, such as a CT scanner, MRT scanner or otherwise. The plurality of frames are registered relative to each other to yield an highly accurate virtual three-dimensional model of the object that is consistent with all the frame, without requiring or using pre-knowledge of the spatial relationship between the frames.

SUMMARY OF THE INVENTION

A method is provided for constructing a virtual three-dimensional model of an object. The method uses a scanner or other source of frames, a data processing system, and at least one machine-readable memory accessible to the data processing system. In an optical scanner embodiment, the method includes the step of scanning the object with the scanner and thereby obtaining a set of two-dimensional images of the object. In a preferred embodiment, the scanner projects a pattern onto the object and an electronic imaging device detects the reflected pattern and generates two-dimensional images of the reflected pattern. During scanning, the scanner and object are moved relative to each other resulting in each image being taken from a different position relative to the surface of the object. The method continues with a step of processing the data representing the set of images with the data processing system so as to convert each of the two-dimensional images into a data representing a frame. The frame is essentially a cloud of individual points, each point in each frame is expressed as a location in a three-dimensional coordinate system. Thus, the set of images are processed to thereby generate a set of frames corresponding to the set of images.

Since each frame is associated with an image and the images are taken from different perspectives relative to the object, an individual point on the object may have different coordinates from one frame to another. The spatial discrepancy in both translation and rotation is corrected for in a registration procedure. The method thus continues with a step of further processing the data representing the set of frames with the data processing system so as to register the frames relative to each other to thereby produce a three-dimensional virtual model of the object substantially consistent with all of the frames.

The registration may comprise a frame to frame registration of the set of frames, wherein each frame is registered with respect to one other frame in the set of frames. Alternatively, the registration may be a cumulative registration of the set of frames, wherein at least some of the frames are registered to a plurality of other frames previously having been registered to other frames.

In another aspect, a method is provided of constructing a virtual three-dimensional model of an object using a data processing system, and at least one machine-readable memory accessible to said data processing system. The method includes the steps of:

(a) obtaining a set of at least two digital three-dimensional frames of portions of the object, wherein the at least two frames comprise a set of point coordinates in a three dimensional coordinate system providing differing information of the surface of the object, wherein those frames provide a substantial overlap of the represented portions of the surface of the the object;

(b) storing data representing the set of frames in the memory; and (c) processing said data representing the set of frames with the data processing system so as to register the frames relative to each other to thereby produce a three-dimensional virtual representation of the portion of the surface of the object covered by the set of frames, without using pre-knowledge about the spatial relationship between the frames; the three-dimensional virtual representation being substantially consistent with all of the frames.

In another aspect, a method is provided for registering a first frame, representing a first set of three-dimensional coordinates of points on the surface of an object, relative to second frame, representing a second set of three-dimensional coordinates of points on the surface of the object. The frames can be from any suitable source, such as a CT scanner, optical scanner, or other type of device. The method includes the steps of:

storing the sets of three-dimensional coordinates of points in a machine-readable memory;

processing the sets of three-dimensional coordinates with a data processing unit reading said machine-readable memory, said step of processing comprising the steps of:

a) determining ΔX, ΔY and ΔZ offsets between overlapping points in said frames;
b) changing the coordinates in second frame in accordance with said ΔX, ΔY and ΔZ offsets;
c) computing a surface for said first frame from points in said first frame;
d) computing normal vectors from said points in said second frame to the surface and a net normal vector;
e) determining X, Y and Z components of a rotation matrix from said surface and the points in said second frame, said rotation matrix indicting the amount of rotation required to fit said second frame to said first frame; and
f) applying the net normal vector and the rotation matrix to the points in said second frame to thereby generate a new set of coordinates of said second frame in three dimensions to fit the second frame to the first frame.

In another aspect, a method is provided for creating a virtual three-dimensional object, comprising the steps of:
a) scanning the object in a series of scans, each scan generating a set of images;
b) converting the of images into a set of three-dimensional frames;
c) registering the frames in each of the series of scans to each other to thereby generate a series of segments, each segment comprising a portion of a three-dimensional model of the object; and
d) registering the segments relative to each other to thereby create the virtual three-dimensional model.

BRIEF DESCRIPTION OF THE DRAWINGS

FIG. 10 illustrates a fundamental principle of the technique that is used for calibration of the scanner and generation of three-dimensional information of an object, which is considered to be an improvement over the calculations required by the method of FIG. 9.

FIG. 24 is an illustration of a first calibration table for the scanner after completion of the Z calibration step;

FIG. 25 is an illustration of a second calibration table for the scanner after completion of the X-Y calibration step. The entries in the second calibration table of FIG. 25 are used to complete the mm entries in the calibration table of FIG. 24.

FIG. 26 is an illustration of the first calibration table for the scanner after the calculations from the table of FIG. 25 have been performed for ray $R_{2,3}$ and the results entered in the first table. It will be understood that a similar calculation from calibration table #2 (FIG. 25) is done for each ray at both distances and the entries in mm for each ray are entered in calibration table #1 (FIG. 24).

FIG. 37D illustrates that the low resolution of the scanner's projection pattern, as indicated by the widely spaced points in FIG. 37C, is compensated by registration of large overlap of frames, as illustrated in FIG. 37C, and results in a high resolution surface.

FIG. 48A–48C are a flow diagram of a cumulative registration process.

FIG. 54 is a screen shot of a workstation computer (either scanning station or back office server workstation), showing the available registration parameters and variables that can be changed by the user when performing either a frame to frame registration or a cumulative registration.

FIG. 60 also shows the various parameters by which the orthodontist can adjust the shape of the arch, the distance between the teeth, the distance between the molars, and other parameters, so as to provide a unique and customized target situation for the patient.

DETAILED DESCRIPTION OF PREFERRED EMBODIMENT

Part 1. Overview

Figure 1:
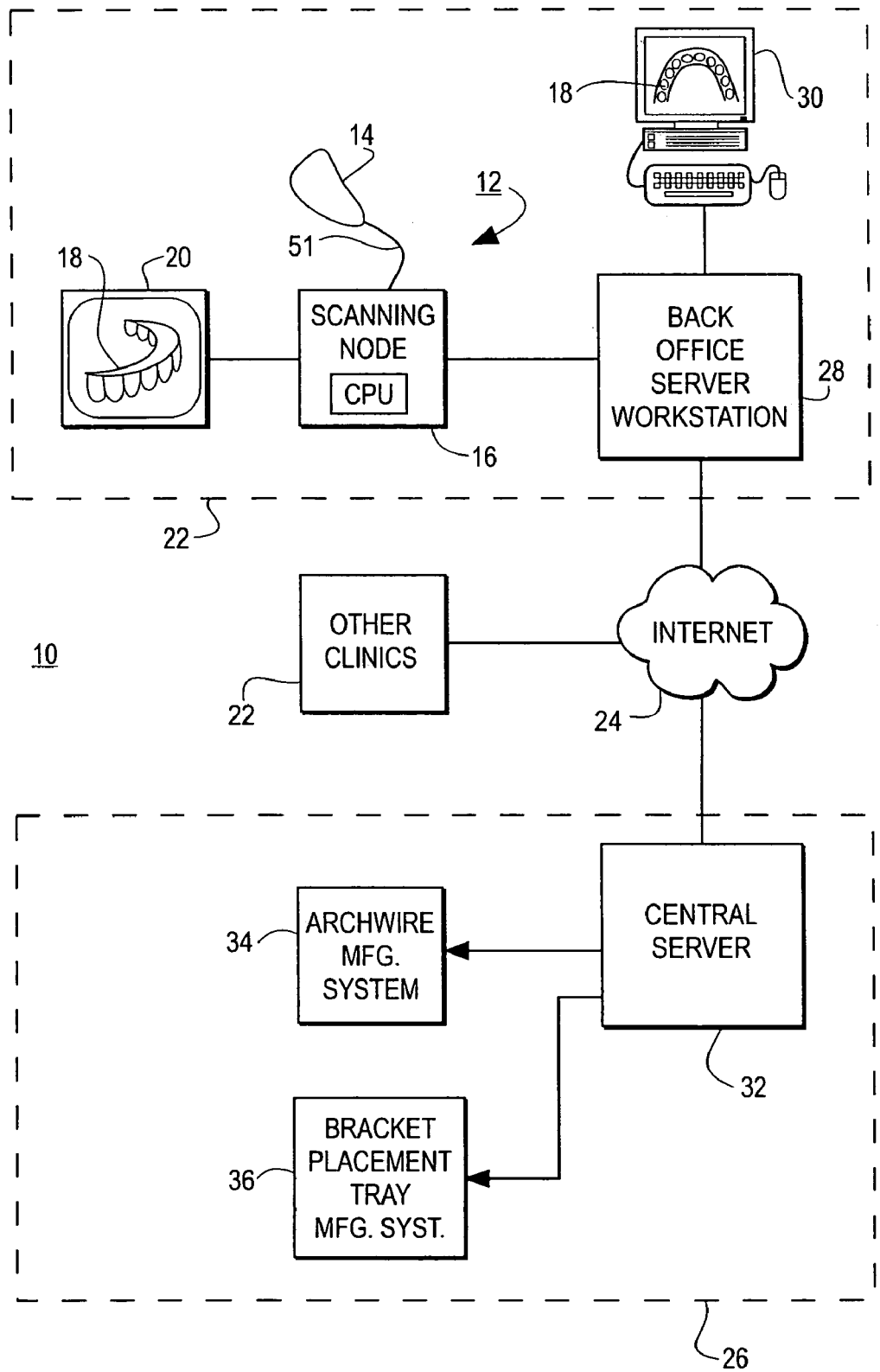
FIG. 1 is an illustration of an orthodontic care system incorporating a hand-held scanner system in accordance with a representative embodiment of the invention. The hand-held scanner is used by the orthodontist or the assistant to acquire three-dimensional information of the dentition and associated anatomical structures of a patient and provide a base of information to diagnose and plan treatment for the patient.

FIG. 1 is an illustration of an orthodontic care system 10 incorporating a scanner system 12. The scanner system 12 includes a hand-held scanner 14 that is used by the orthodontist or his assistant to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional computer model 18 of the dentition and provides the orthodontist with a base of information for diagnosis, planning treatment, and monitoring care for the patient. The model 18 is displayed to the user on a monitor 20 connected to the scanning node 16.

As noted above, the scanner system 12 described in detail herein is optimized for in-vivo scanning of teeth, or alternatively, scanning a plaster model of the teeth and/or an impression of the teeth. However, it will be apparent to persons skilled in the art that the scanning system 12 can by readily optimized for a variety of other diagnostic and/or treatment planning and/or monitoring uses in the medical arena. An example is scanning the face or head and planning plastic or orthopedic surgery. It can be readily adapted to virtually limitless number of applications in industrial, manufacturing, forensic, archeological, scientific, archival or other applications. Similarly the registration procedures described herein can be used for virtually any three dimemsional object, and the registration procedure can work with 3-D information of different sources besides the optical scanner.

The orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user interface, including a monitor 30. The back office server 28 executes an orthodontic treatment planning software program. The software obtains the three-dimensional digital data of the patient's teeth from the scanning node 16 and displays the model-18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized archwire for the patient given the selected bracket positions. When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22. The invention is also applicable to other types of appliance systems; brackets and archwires are shown in the illustrated embodiment but other types of appliance systems can benefit from the scanning system described herein, such as removable aligning devices; retainers, Herbst appliances, etc.

As shown in FIG. 1, the precision appliance service center 26 includes a central server 32, an archwire manufacturing system 34 and a bracket placement manufacturing system 36. These details are not particularly important to the scanning system 12 per se and are therefor omitted from the present discussion for sake of brevity. For more details on these aspects of the illustrated orthodontic care system, the interested reader is directed to the patent application of Rüdger Rubbert et al., filed on the same date as the instant application, entitled INTERACTIVE AND ARCHWIRE-BASED ORTHODONTIC CARE SYSTEM BASED ON INTRA-ORAL SCANNING OF TEETH, Ser. No. 11/285,629, the contents of which are incorporated by reference herein.

Figure 2:
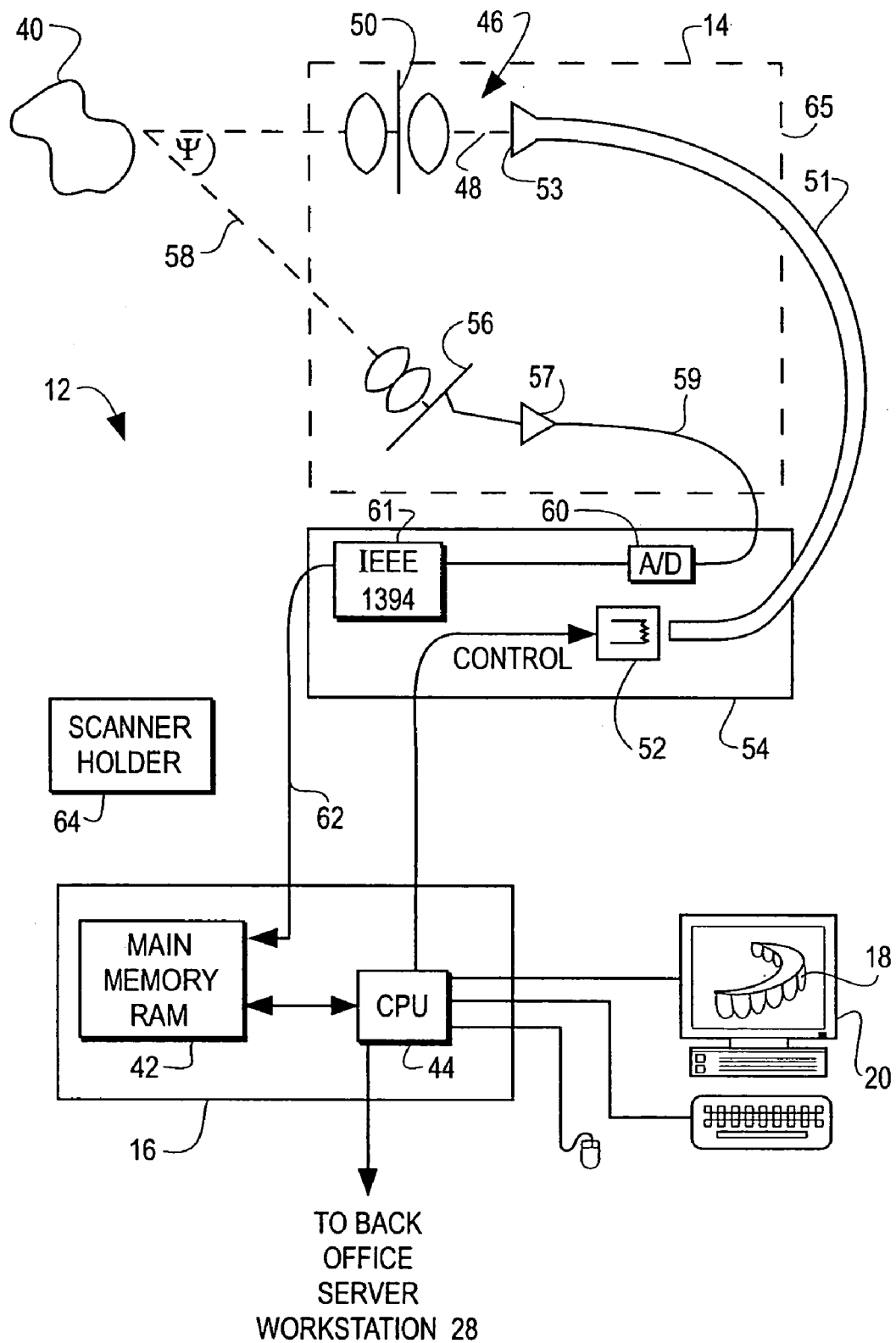
FIG. 2 is a block-diagram of a scanning system, suitable for use in the orthodontic care system of FIG. 1.

FIG. 2 is a more detailed block-diagram of the scanning system 12, suitable for use in the orthodontic care system of FIG. 1. The scanning system 12 is a mechanism for capturing three-dimensional information of an object 40, which in the present example is the dentition and surrounding anatomical structures of a human patient, e.g., gums, bone and/or soft tissue. The scanning system 12 includes a scanner 14 which is used for image capture, and a processing system, which in the illustrated example consists of the main memory 42 and central processing unit 44 of the scanning node or workstation 16.

The scanner 14 includes a projection system 46 that projects a pattern onto the object 40 along a first projection axis 48. The projected pattern is formed on a slide 50 which is placed in front of a light source 53. In the illustrated embodiment, the light source 53 comprises the terminus of a fiber-optic cable 51. The cable 51 carries a high intensity flash generated by a flash lamp 52 located in a base unit 54 for the scanner. A suitable flash lamp is the model FX-1160 flash unit available from Perkin Elmer. The illuminations of the flash lamp 52 cause the pattern contained in the slide 50 to be projected onto the three-dimensional surface of the object. Further details on the types of patterns suitable for the pattern are set forth in the following co-pending patent applications of Rüdger Rubbert et al:, Ser. No. 09/254,755 filed Mar. 9, 1999; Ser. No. 09/560,131 filed Apr. 28, 2000, and Ser. No. 09/673,863 filed Nov. 30, 2000 assigned to the assignee of the present invention, the contents of which are incorporated by reference herein. A presently preferred projection pattern is described below. The details on the optics of the projection system 46 are set forth in further detail below.

The scanner 14 further includes an electronic imaging device 56 comprising an array of photo-sensitive pixels. A preferred embodiment is an off-the-shelf, color-sensitive, charged-coupled device (CCD) of a size of 1,028×1,028 pixels arranged in an array of rows and columns. The Sony ICX205AK CCD chip is a suitable electronic imaging device. The electronic imaging device 56 is oriented perpendicular to a second imaging axis 58, which is off-set from the projection axis 48. The angle $\Psi$ between the projection and imaging axes need not be known in a preferred embodiment of the invention. However, if the 3D calculations are made in accordance with the parameters of FIG. 9, then the angle and the separation distance between the center of the imaging device 56 and the center of the light source 53 need to be known.

The angle $\Psi$ will be optimized during design and manufacture of the scanner depending on the desired resolution required by the scanner. This, in turn, is dependent on the degree to which the surface under scrutiny has undercuts and shadowing features which would result in the failure of the imaging device to detect the projection pattern. The greater the angle $\Psi$, the greater the accuracy of the scanner. However, as angle $\Psi$ increases, the presence of undercuts and shadowing features will block the reflected pattern and prevent capture of the pattern and subsequent three-dimensional analysis of those portions of the surface. Angle $\Psi$ is shown somewhat exaggerated in FIG. 2, and will generally range between 10 and 30 degrees for most applications.

The electronic imaging device 56 forms an image of the projection pattern after reflection of the pattern off of the surface of the object 40. The reflected patterns imaged by the imaging device contain three-dimensional information as to the surface of the object, and this information needs to be extracted from the images. The scanning system therefore includes a processing subsystem which is used to extract this information and construct a three-dimensional virtual model of the object 40. In the preferred embodiment, this processing subsystem consists of a memory 42 storing calibration information for the scanner, and at least one processing unit, such as the central processing unit 44 of the scanning workstation 16. The location of the memory and the processing unit is not important. They can be incorporated into the scanner 14 per se. Alternatively, all processing of the images can take place in the back office server 28 or in another computer. Alternatively, two or more processing units could share the processing in order to reduce the amount of time required to generate the three-dimensional information.

The memory 42 stores a calibration relationship for the scanner 14. The calibration relationship, which can be in the form of a table or one more mathematical functions, comprises information used to compute three-dimensional coordinates of points on the object that reflected the projection pattern onto the imaging device. The information for the table is obtained during a calibration step, performed at the time of manufacture of the scanner 14. The calibration table includes an array of data storage locations that contain two pieces of information. Firstly, the calibration table stores pixel coordinates in X and Y directions for numerous portions of the projection pattern that are imaged by the electronic imaging device 56, when the pattern is projected onto a calibration surface at two different distances during a calibration procedure. Secondly, the table stores distance information, (e.g., in units of tenths of millimeters), in X and Y directions, for the portions of the projection pattern imaged at the two different distances. A preferred method for generation and use of the calibration table is explained in further detail below.

The scanning system requires at least one processing unit to perform image processing, three-dimensional calculations for each image, and registration of frames to each other. The processing unit 44 in the illustrated embodiment is the central processing unit (CPU) of the scanning work station 16. The CPU 44 processes the image of the pattern after reflection of the pattern off the surface of the object 40 and compares data from the image to the entries in the calibration table. From that comparison (or, more precisely, interpolation relative to the entries in the table, as explained below), the processing unit 44 derives spatial information, in three dimensions, of points on the object that reflect the projected pattern onto the electronic imaging device.

Basically, during operation of the scanner to scan an object of unknown surface configuration, hundreds or thousands of images are generated of the projection pattern as reflected off of the object in rapid succession as the scanner and object are moved relative to each other. For each image, pixel locations for specific portions, i.e., points, of the reflected pattern are compared to entries in the calibration table. X, Y and Z coordinates (i.e., three dimensional coordinates) are obtained for each of these specific portions of the reflected pattern. For each picture, the sum total of all of these X, Y and Z coordinates for specific points in the reflected pattern comprise a three-dimensional "frame" or virtual model of the object. When hundreds or thousands of images of the object are obtained from different perspectives, as the scanner is moved relative to the object, the system generates hundreds or thousands of these frames. These frames are then registered to each other to thereby generate a complete and highly accurate three-dimensional model of the object 40.

Stray data points are preferably canceled out in generating the calibration table or using the calibration table to calculate three-dimensional coordinates. For example, a smoothing function such as a spline can be calculated when generating the entries for the calibration table, and the spline used to cancel or ignore data points that deviate significantly from the spline.

FIG. 2 also shows a few other features of the presently preferred scanning system 12. After the CCD imaging device 56 captures a single image, the analog voltage signals from the device 56 are amplified in an amplifier 57 and fed along a conductor 59 to an analog to digital converter 60. The digital signal is converted into a bitmap stream of digital image data. The data is formatted by a module 61 into an IEEE 1394 "firewire" format for transmission over a second conductor 62 to the main memory 42 of the scanner work station 16. The scanning system includes an optical scanner holder 64 for the user to place the scanner after the scanning of the dentition is complete. These details are not particularly important and can vary considerably from the illustrated embodiment. As noted earlier, preferably the scanning system is constructed to provide a minimum of equipment and clutter at the chair side. Hence, the scanning work station 16 is preferably located some distance away from the chair where the patient sits. The cable leading from the scanner 14 to the base station and/or workstation 16 could be suspended from the ceiling to further eliminate chairside clutter.

The scanning work station 16 also includes the monitor 20 for displaying the scanning results as a three-dimensional model 18 of the dentition in real time as the scanning is occurring. The user interface also includes a keyboard and mouse for manipulating the virtual model of the object, and for entering or changing parameters for the scanning, identifying sections or segments of scans that have been obtained, and other features. The scanning station may also include a foot switch, not shown, for sending a signal to the CPU 44 indicating that scanning is commencing and scanning has been completed. The base station may alternatively include a voice recognition module that is trained to recognize a small set of voice commands such as START, STOP, AGAIN, REPEAT, SEGMENT, ONE, TWO, THREE, FOUR, etc., thereby eliminating the need for the foot switch. Scanner start and stop commands from the CPU 44, in the form of control signals, are sent to the light source 52, thereby controlling the illumination of the lamp 52 during scanning.

The light source 52 operates at a suitable frequency, preferably at least greater than one flash per second, such as six flashes per second, and the frame rate of the CCD imaging device 56 is synchronized with the flash rate. With a frame rate of 6 frames per second, and a scanning motion of say 1–2 centimeters per second, a large of overlap between images is obtained. The size of the mirror at the tip 68 of the scanner influences the speed at which scanning is possible. The illustrated embodiment of the mirror at the tip 68 is 18 mm square. A larger mirror reflects more surface of the object and enables faster scanning. A smaller mirror requires slower scanning. The larger the mirror, the more difficult in-vivo scanning becomes, so some trade-off between size and utility for in-vivo scanning exists.

This overlap between images generated by the scanner 14, and resulting three dimensional frames, allows a smooth and accurate registration of frames relative to each other. The frame rate and permissible rate of scanner motion will depend on many factors and can of course vary within the scope of the invention. Flashing a high intensity flash lamp for a brief period of time is a preferred embodiment since it is desirable to reduce the exposure time of the CCD imaging device 56 to reduce blurring since relative motion exists between the scanner and the object. A high intensity lamp is desirable to achieve sufficient signal strength from the imaging device. A preferred embodiment uses 5 μsec flash times with similar exposure periods. An alternative embodiment would use a constant illumination source of high intensity, and control exposure of the imaging device using a shutter, either a physical shutter or using electronic shutter techniques, such as draining charge accumulating in the pixels prior to generating an image. Scanning using longer exposures would be possible without image blur, using electronic image motion compensation techniques described in Lareau, et al., U.S. Pat. No. 5,155,597.

Figure 3:
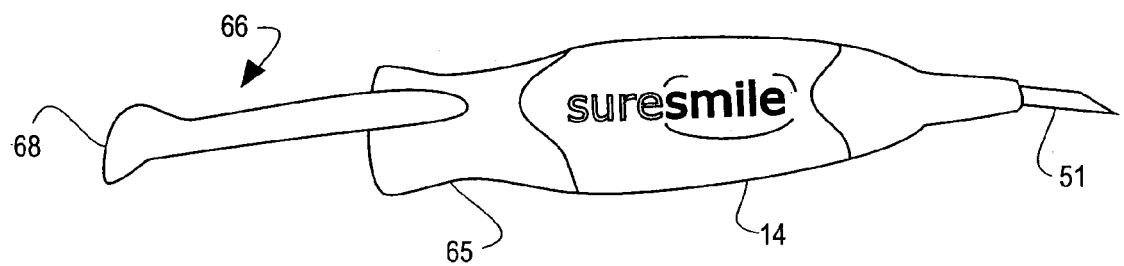
FIG. 3 is a perspective view of a hand-held scanner used to acquire information of an object under scrutiny, suitable for use in the orthodontic care system of FIG. 1.

FIG. 3 is a perspective view of a hand-held scanner 14 used to acquire information of an object under scrutiny, suitable for use in the orthodontic care system of FIG. 1. The projection system 46 and the electronic imaging device 56 of FIG. 2 are contained in the housing 65 for the scanner. The housing 65 is sized and shaped to be held in a human hand. The scanner 14 includes an elongate distal portion 66 having a tip 68. The tip 68 is sized and shaped such that it can be inserted into and moved within an oral cavity of a human so as to enable scanning of anatomical structures inside the oral cavity. A heating mirror (not shown) is placed on the underside of the tip 68 to direct the projection pattern from the optics of the scanner onto the object and to direct the reflected pattern from the object towards the imaging optics 108 of FIG. 7 associated with the electronic imaging device 56. The mirror housing has A/C conductive heating coil that heats the mirror. The mirror is heated to approximately 40 degrees to prevent fogging of the mirror while the scanner is used in-vivo.

Figure 4:
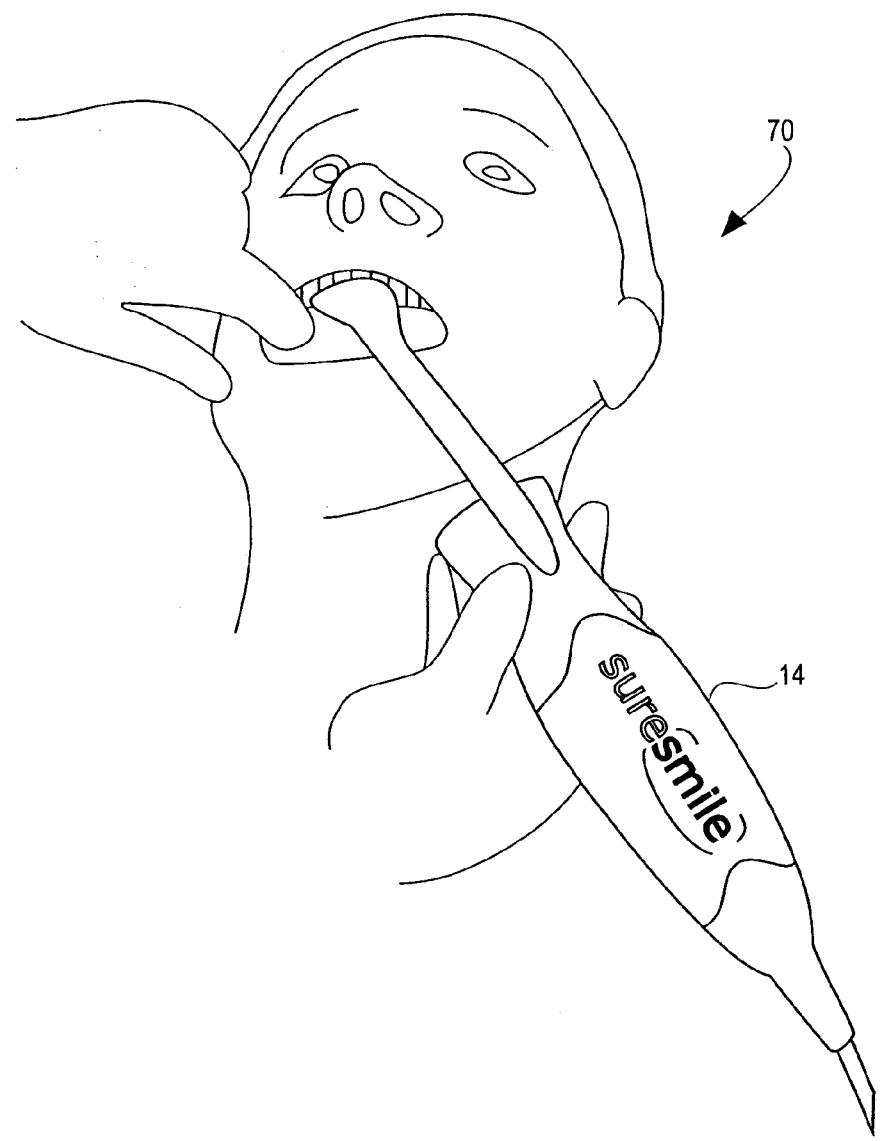
FIG. 4 is an illustration of a patient being scanned with the hand-held scanner of FIG. 3.

FIG. 4 is an illustration of a patient 70 being scanned with the hand-held scanner 14 of FIG. 3. The checks and lips are retracted from the teeth and the tip 68 of the scanner is moved over all the surfaces of the teeth in a sweeping motion at a velocity of perhaps 1–2 centimeters per second. The entire upper or lower jaw may need to be scanned in a series of scans, one for the left side, one for the right side, and one for the front. These individual scans are registered to each other as described below. Voice commands or activation of the foot switch (not shown) indicates when each scanning segment is initiated and terminated. The entire process takes just a few minutes. Depending on the color and translucency of the object and the illumination intensity and frequency of the light source in the scanner, it may be necessary to apply a very thin coating of a bright reflective substance such as Titanium Dioxide to the object.

While FIG. 4 illustrates in-vivo scanning of a human patient, the scanner can of course be used to scan a plaster model of the dentition if that is preferred, or an impression taken from the patient. When scanning an impression or a plaster model, the scanning may be formed in a single pass, without the need for registering scan segments to each other. It is also possible that a scan of a patient may be partially taken in vivo and the remainder from a model or an impression.

Figure 5:
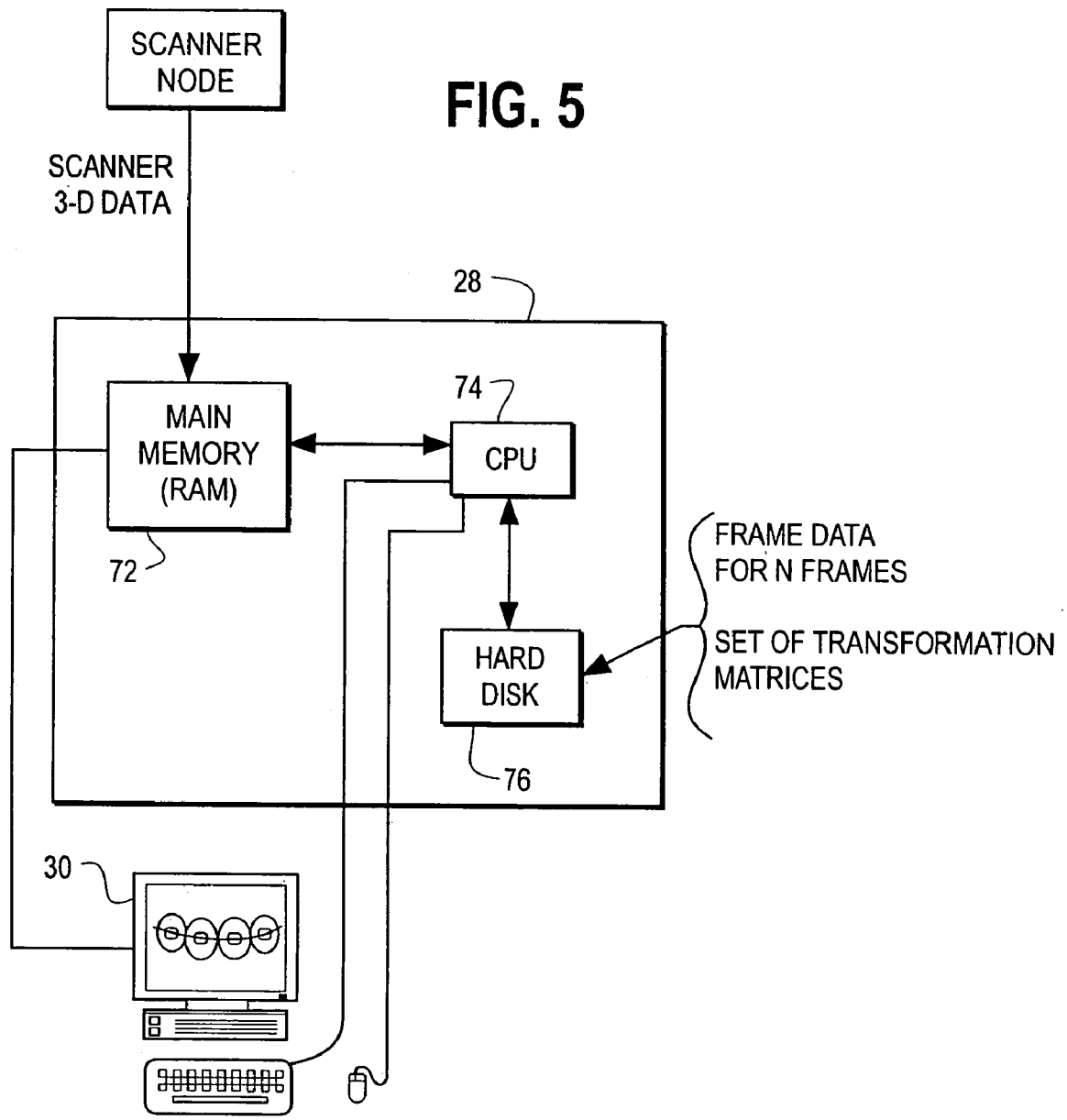
FIG. 5 is a block diagram of the back office server of FIG. 1 showing the elements used to calculate the digital model of the patient's dentition and display the digital model on a screen display of the server.

FIG. 5 is a block diagram of the back office server of FIG. 1 showing the elements used to calculate the digital model of the patient's dentition. After the scanning workstation has processed all the images captured by the scanner and generated a set of three dimensional frames, the frame data is transmitted to the back office server 28. The back office server 28 performs a cumulative registration process for the frames and ultimaty generates and displays the digital model on a screen display 30. The raw scanner data in the form of three-dimensional frames is stored in the main computer memory 72. The frame data for N captured images, $i=1 \ldots N$ from the scanner is stored in the hard disk 74. The hard disk also stores a set of (N−1) transformation matrices [T], for $i=2-N$. The transformation matrices basically contain information as to how each frame of three-dimensional points needs to be translated and rotated in a three-axis Cartesian coordinate system in order to be registered with the other frames in a best-fit manner. One of the frames, such as the first frame in the series, is a starting point for registration and no transformation matrix is obtained for that frame. The generation of the transformation matrices, and use of the matrices with the frame data to generate the three dimensional model, is described in further detail below.

Part 2. Three-Dimensional Image Generation

Figure 6:
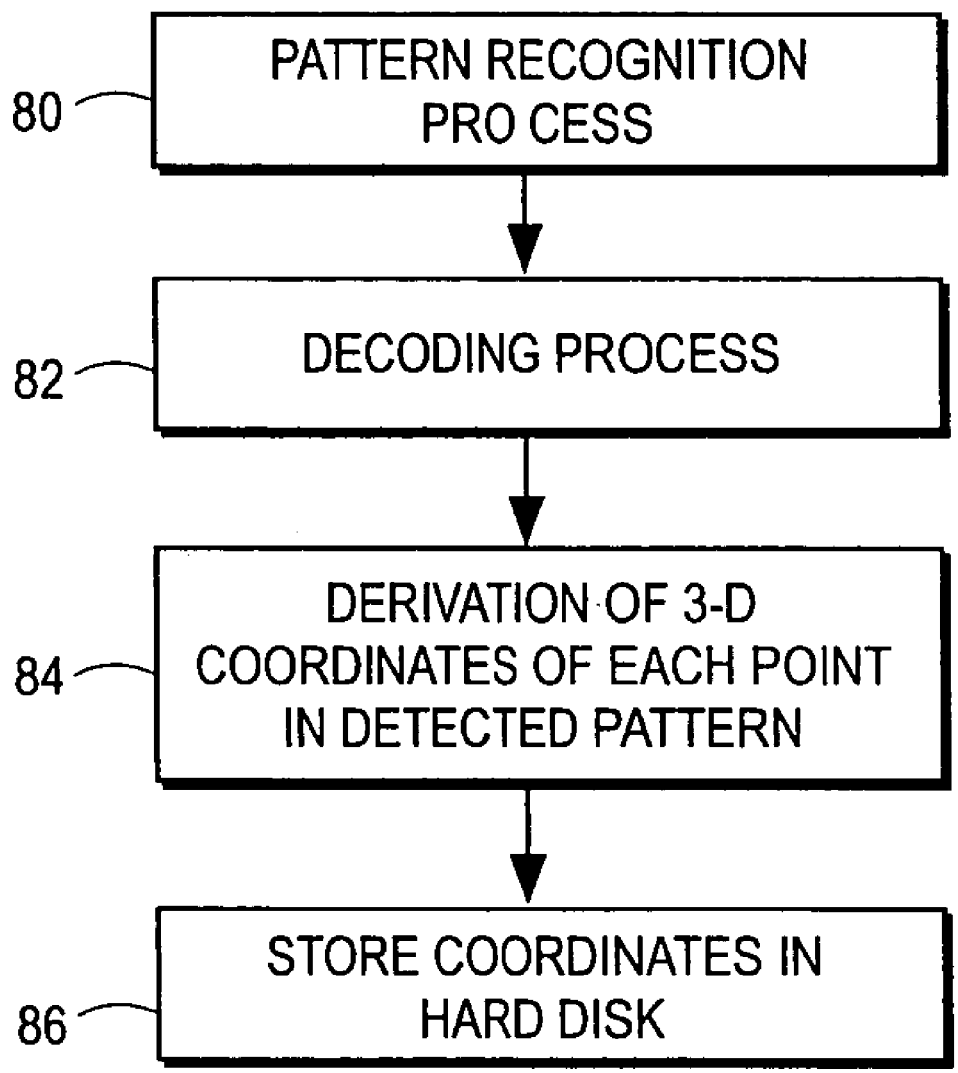
FIG. 6 is a flow diagram illustrating the sequence of steps used by the processing unit in the scanning station to calculate three-dimensional information of an object from images captured by the scanner.

With the above general introduction and overview in mind, a presently preferred process of capturing two dimensional images with the scanner and generation of a three-dimensional model for each image will now be described in detail in this section. FIG. 6 is a flow diagram illustrating the sequence of steps used by the processing unit 44 in the scanning station 16 (FIG. 2) to calculate three-dimensional information of an object for a single image captured by the scanner 14. This process shown in FIG. 6 is performed for each image.

This process can be executed in one processor, or may be performed or shared by multiple DSP processors sharing access to a memory storing the captured two-dimensional bitmap images from the scanner, e.g., memory 42 of FIG. 2. The type of processor is of course not important. The goal of distributed processing is to reduce the time required for processing the scanned image. For example, one processor could perform the cross-correlation process described below, another perform the pattern recognition, another decoding, and another 3-D calculation. These processes could be performed independently, each process associated with independent files shared on a disk memory. The processor assigned to one or more of the processes of FIG. 6 accesses the files as needed. For example, the output file from the decoding process is written on a disk or memory available to the other processing units. The processing units are on a network in this example. The processor assigned to 3-D calculation access the decoding output file and writes the result, a set of coordinates for N frames and N−1 transformation matrices, onto the disk or memory. Any one of the processors assigned to perform registration could then access the N frame data and the N−1 transformation matrices and perform the registration procedures described below.

The process of FIG. 6 consists of four principal steps: a pattern recognition process 80, a decoding process 82, a process 84 of derivation or calculation of three-dimensional coordinates for each point in the detected and decoded pattern, and finally a step 86 of storing the three dimensional coordinates in a memory, such as the memory 42 of the scanning work station 16. Again, this process is performed for each captured image during the scanning process. In a typical scanning scenario, hundreds or even thousands of images may be captured, hence this process of FIG. 6 may be performed hundreds of times. The result of the process is the storage of a large number of sets of three-dimensional coordinates, each set or "frame" associated with a single captured image. The registration of these frames relative to each other to generate a complete virtual model of the object is described in Part 3 of this document.

As the scanner is moved over the dentition, the imaging device acquires a series of bitmap images. The acquired bitmaps are analyzed using pattern recognition. Pattern recognition detects the median lines of the projected lines, endpoints of the lines and the centers of the colored dots. Other types of patterns are of course possible, such as using triangles, squares, or other coding features. The coding is in the vertical direction (in the direction of the parallel lines), since the distortion of the projection pattern provided by the surface of the object is in this direction, as explained more fully in the Rubbert et al. patent application Ser. No. 09/560,131 filed Apr. 28, 2000, incorporated by reference herein.

The pattern recognition process uses sub-pixel-precision. The color of every dot is analyzed as well. Based on the knowledge of the pattern structure and using the colored dots, the origin in the pattern for every recognized line is determined. This is necessary, as significant portions of the projected pattern may not be visible to the imaging optics due to shadowing, undercuts and un-sharp areas. A two-dimensional to three-dimensional conversion algorithm uses the knowledge of the origin of each imaged line with respect to the pattern to compute three-dimensional coordinates of the points in the object. As the lines are often captured only as fragments, the decoding algorithm does not always have sufficient information on each line to unequivocally assign that line to the pattern. The algorithm therefore examine several scenarios of possible affiliations and looks for conflicts. In this way the inconsistent scenarios are filtered out. The lines in the projection pattern do not change their order in the image. For example, if the lines in the projection pattern are sequentially numbered 1–80, and line 43 is to the left of line 44, in the captured image line 43 will be always be to the left of line 44 and never to the right of line 44. Inconsistent scenarios are indicated where the order of lines is violated. The correct order of the lines can be deduced by a suitable algorithm that examines the scenarios based on line order and eliminates all those where conflicts or inconsistent line numberings exists. A unique solution will be found.

While the preferred embodiment of the three-dimensional conversion algorithm is based on a sophisticated calibration process and does not make use of any knowledge of the optical parameters, an alternative embodiment could use general principle of analytical triangulation assuming that we do have such knowledge. Analytical triangulation will be explained with reference to FIG. 9. The projecting device projects a pattern of distinguishable elements onto a surface. This projected pattern is imaged. For each captured element, is must be possible to tell its origin at the pattern. This allows us to determine the angle β between the optical axis of the projection device and the one ray that has projected that element. The location of the pixel at the CCD chip that has captured that element allows us to determine the angle β between the optical axis of the imaging system and the one ray that leads from the projected element at the surface to the CCD pixel. Knowing those two angles, the angles of the two optical axes with respect to the baseline and the length of the baseline, allows us to calculate the spatial position of the element relatively to the scanning device. This calculation can be done for every detected element within one captured image and leads to a plurality of three-dimensional points. It is important to understand that as a result from this calculation we receive an undistorted, true to scale representation of the surface. While every two dimensional image shows distortions due to parallax effects, the triangulation process eliminates this effect.

The analytical triangulation method requires precise knowledge of optical parameters. The preferred embodiment using a calibration table for the scanner does not require this knowledge.

A. Scanner Manufacture and Calibration

Before describing the details of the process steps shown in FIG. 6, an illustrative embodiment of the scanner 14 itself and its manner of calibration will be described first.

Figure 7:
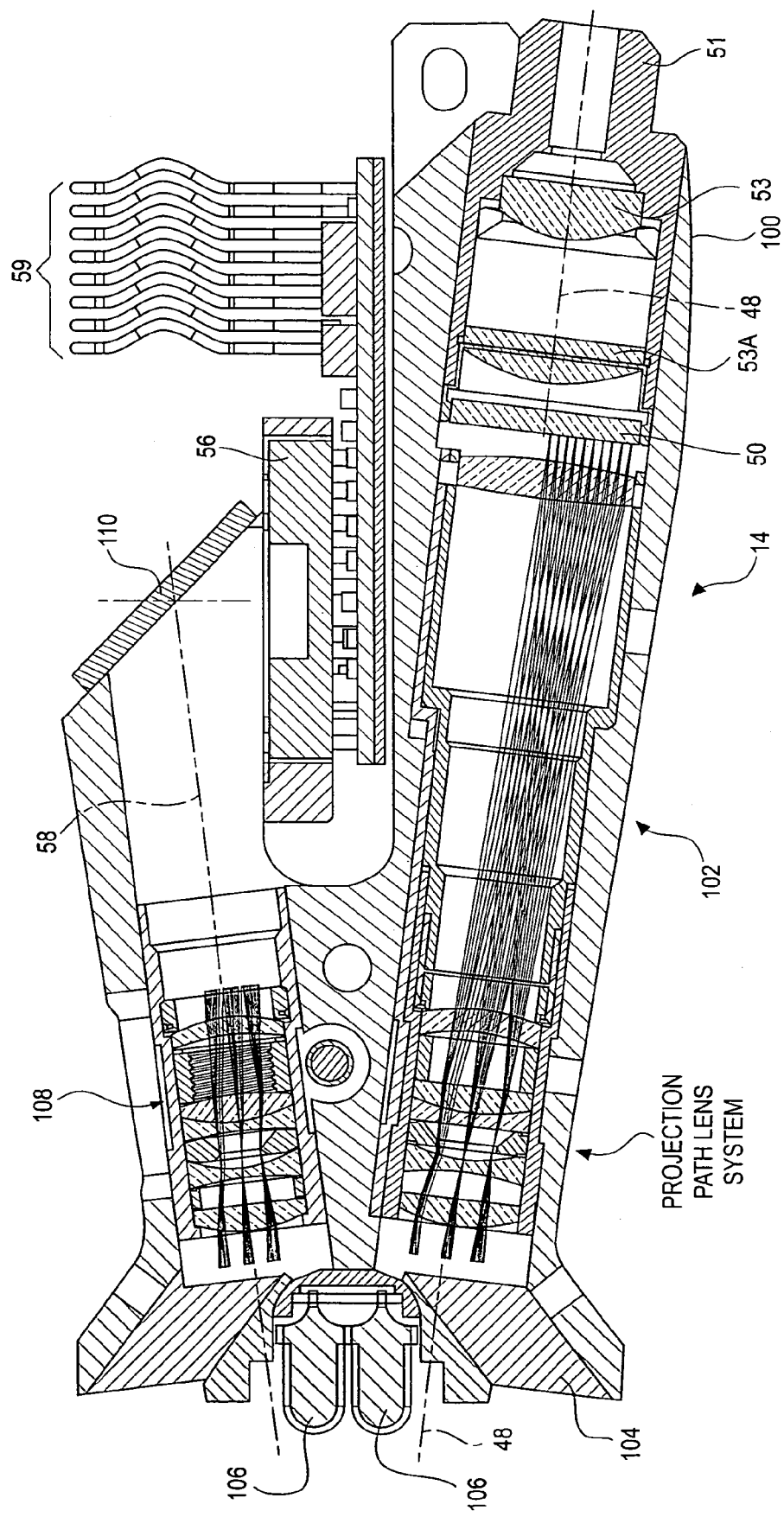
FIG. 7 is a cross-sectional view of the scanner of FIG. 3, showing the optical elements of the projection and imaging aspects of the scanner.

FIG. 7 is a cross-sectional view of a portion of the hand-held scanner 14 of FIG. 3, showing the optical elements of the projection and imaging aspects of the scanner. The scanner includes the fiber-optic cable 51 carrying flashes from a flash lamp in the base station 54 of FIG. 2 to a condenser system consisting of a group of lenses 53A. Light from the light source 53 illuminates a pattern formed in a slide 50. Wide variation is possible in the choice of the pattern. A presently preferred embodiment is described subsequently in conjunction with FIG. 11. The pattern is directed by a projection lens system 102 out of the scanner to the mirror housed at the tip 68 of the scanner (FIG. 3) and towards the object under investigation. The scanner further includes a several LED light sources 106 (e.g., 2 or 6), which are used to provide general illumination of the object during scanning to assist the user in scanning the dentition. A prism 104 surrounds the LED light sources. The axis of the projection system is shown as axis 48.

The projection pattern is reflected off of the object, reflected by the mirror in the tip 68 and received by an imaging lens system 108 centered about an imaging axis 58. The received pattern is reflected off a mirror 110 onto the CCD electronic imaging device 56. The CCD 56 produces a voltage signal for each pixel in the device. The level of the signal is an indication of the level of light impinging on that pixel, allowing an image to be produced from the CCD. The signals are read out of the CCD using known circuitry and amplified. The amplified analog signal is collected and transmitted along conductors 59 to the base unit for conversion to digital form. The signal from the CCD is converted into a colored bitmap image in the illustrated embodiment. Color is used in the projection pattern in the illustrated embodiment, therefore a CCD chip is selected which can detect colors. A black and white system is of course also possible.

In the illustrated embodiment, the separation distance between the light source and the projection pattern is not known or needed, nor is the angle between the axes 48 and 58.

However, some non-zero angle between the axes is required in order to obtain depth information. The angle selected will depend on the type of surface or object the scanner will be used for. These types of implementation details will vary considerably depending on the application. Furthermore, it is possible to make the two axes 48 and 58 completely independent of each other by locating the projection and imaging in separate, independently moveable devices. This is described in more detail in the patent application of Rüdger Rubbert et al, Ser. No. 09/254,843, the contents of which are incorporated by reference herein. The calibration procedures described herein are of particular advantage when the projection device and the imaging device are in two separate, independently moveable units.

Figure 8:
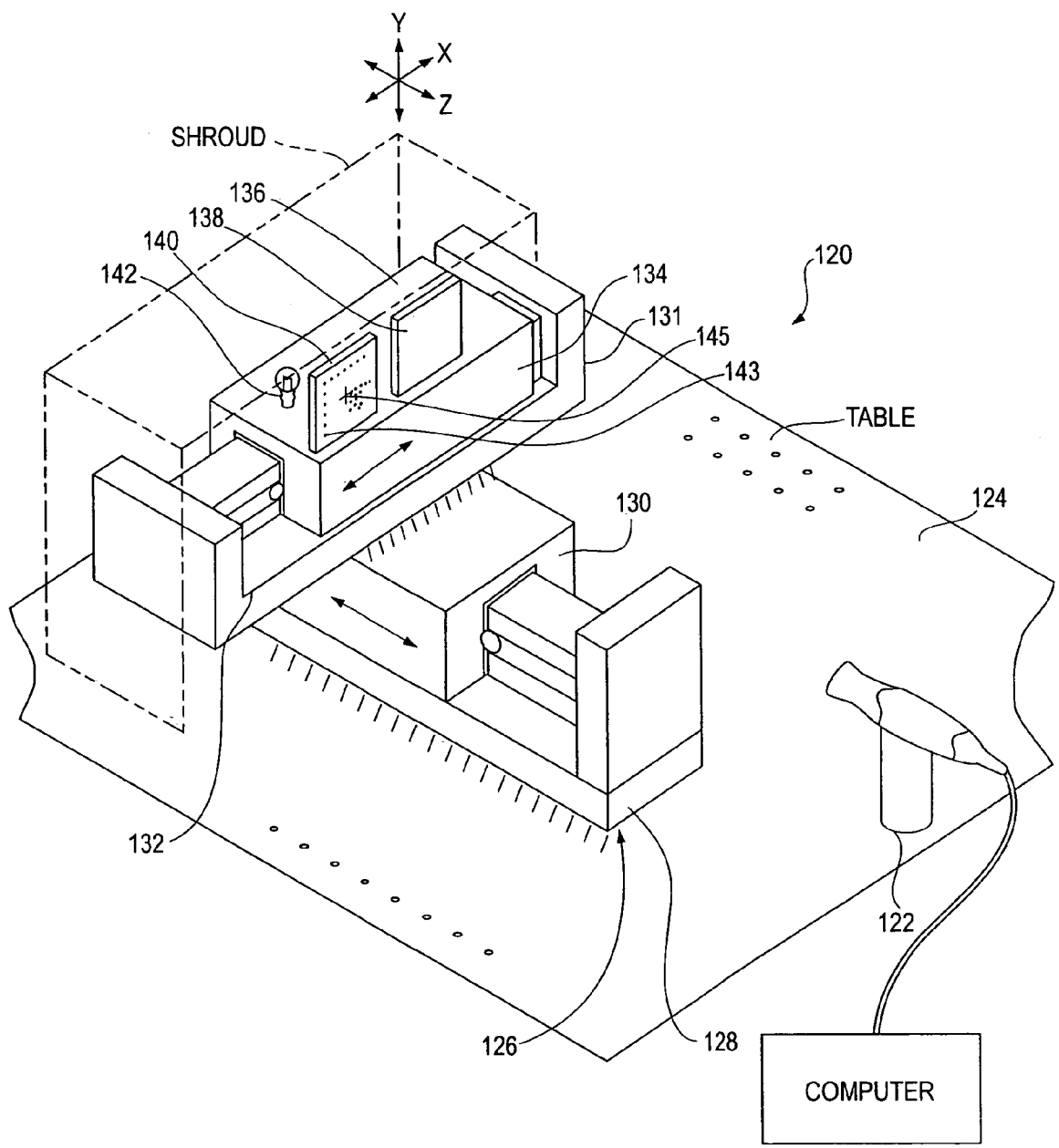
FIG. 8 is a perspective view of a scanner calibration apparatus of station that is used to calibrate the scanner and obtain data for entry in a calibration table stored in the memory of the scanner system.

FIG. 8 is a perspective view of a presently preferred scanner calibration station 120 that is used to calibrate the scanner 14 at the time of manufacture. The purpose of the station 120 is to obtain data for a calibration relationship for the scanner, such as a calibration table, which is stored in the memory of the scanner system. Some variation in the design of the calibration station is possible; the principle of operation of the calibration station is that the scanner is calibrated by projecting the pattern onto a reference object of precisely known geometry at two known distances (in the Z direction) and known spatial extent (X and Y directions). A planar reference object is preferred, but it is theoretically possible to use any object of known geometry, but more computationally complex to use such objects. The goal of the calibration procedure is to compile a set of information (e.g., in the form of a table) that completely calibrates the scanner and places it in condition for use to scan objects of unknown surface geometry, without the need for precise knowledge of the mechanical or optical properties of the scanner. While the present embodiment describes a calibration table as the result of the calibration process, the information may be in other equivalent forms, such as mathematical relationships or formulae between pixel address and distance, which are operated on to derive distance information at the time of use.

Before discussing the presently preferred calibration device and calibration relationship, a discussion of the principles of the calibration invention will be set forth for ease of understanding.

Figure 9:
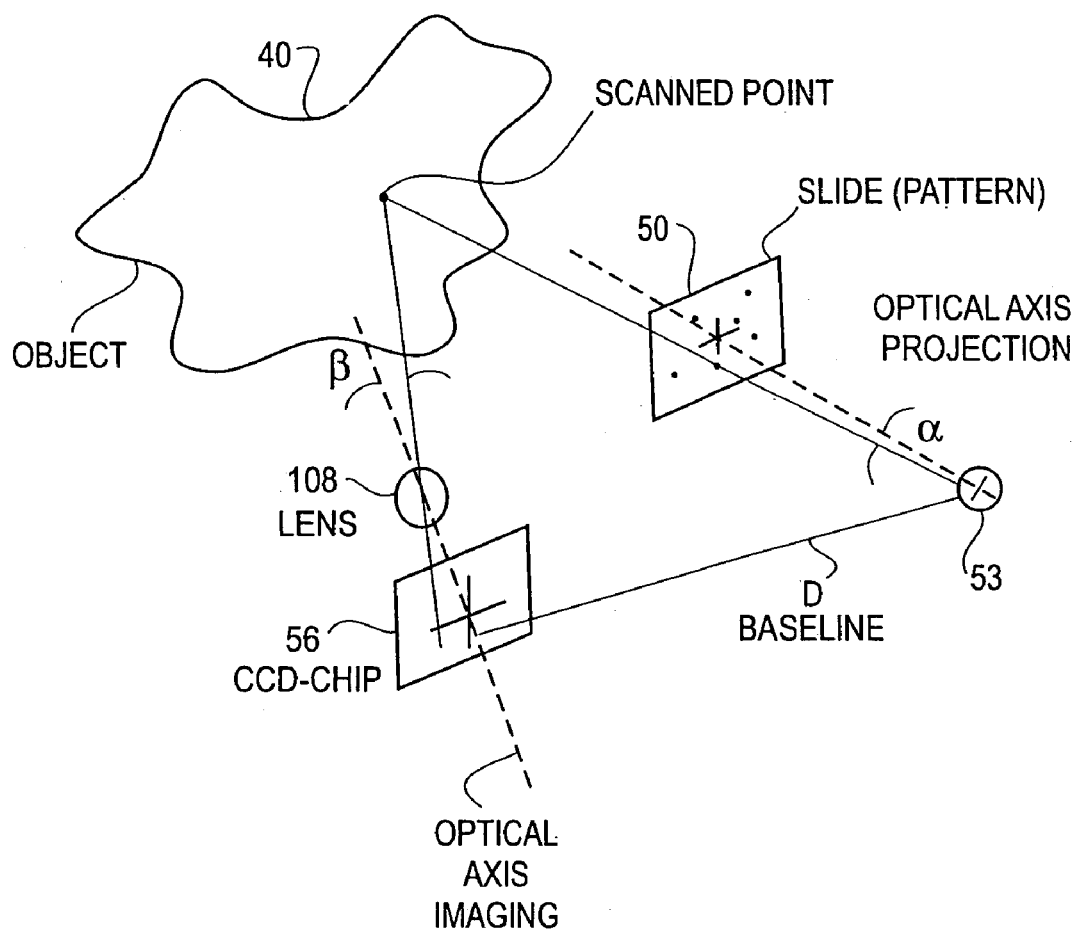
FIG. 9 is an illustration of the relevant parameters that can be used to calculate surface configuration of the object in accordance with a known fashion.
Figure 9A:
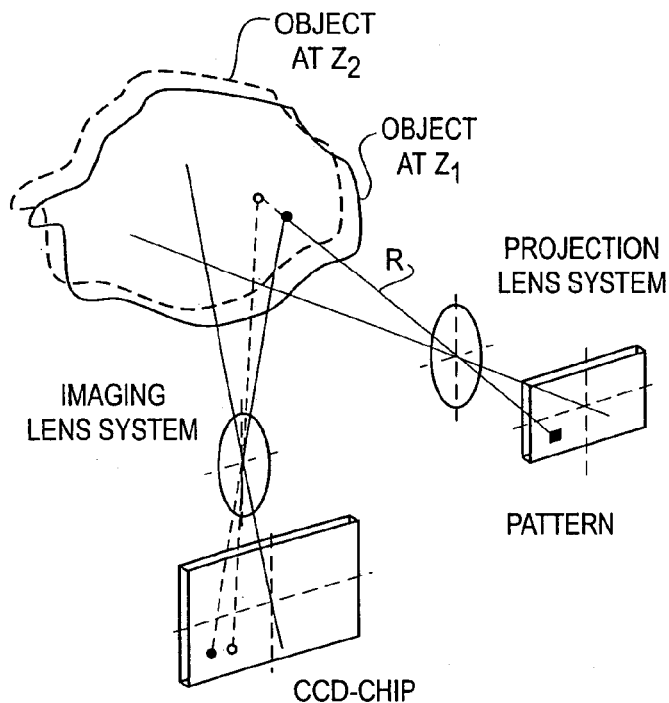
FIG. 9A is an illustration of an electronic imaging device of a scanner, associated imaging lens system, and an object reflecting a projection pattern onto the imaging device at two different distances.

A 3D imaging device as disclosed in this application does initially not deliver 3D information, but only 2D information as the CCD chip is a 2D imaging device. Information on the $3^{rd}$ dimension therefore has to be determined in an extra processing step. The additional information that we can use to perform such a 3D calculation is the spatial arrangement of the optical components, such as shown in FIG. 9A. FIG. 9A shows a schematic arrangement of components. One portion of the pattern is indicated with a small square, and the ray along which this portion would be projected is also displayed. The point, where this ray would intersect with the surface of the object, is displayed as a circle. At the center of this circle, the portion of the pattern would be projected onto the surface of the object. One of the reflected rays will run through the imaging lens system and such be projected onto the surface of the CCD chip, which will cause a corresponding signal. In this figure, only the center rays are displayed, e.g. the rays that run through the center of the lens systems.

Assuming that there is precise knowledge of the geometrical arrangement of the components, it would be possible to precisely calculate the spatial coordinates of the part of the surface of the object that reflects the considered portion of the pattern. This calculation is only possible under three preconditions:

(i) The geometric arrangement of all components of the scanning system must be precisely known, (ii) The exact characteristics of all components must be known (true x/y-coordinates of all CCD pixels, including precise knowledge of the dimensions of the pattern; and (iii) The lens systems must be 'ideal' which means that the center ray must be an ideal straight line.

In mass production scenario for a scanner, it will be almost impossible to guarantee these preconditions. One possible approach would be to calibrate the individual devices, which means that the deviations of the characteristics from the ideal configuration are determined and noted ("compensative calibration"). The 3D calculation will then base on algorithms like described before, but will additionally take into account known deviations to compensate for individual characteristics of each device. However, this compensational calculation has to be set up very carefully, and errors in terms of plus/minus signs will not easily be detected especially when the deviations are minor.

Another challenge is presented by scanning devices like disclosed in PCT/DE97/01797 by Rubbert, where imaging device and projection device are not physically connected to each other, and therefore the geometrical relationship may be completely unknown.

The calibration procedure that is described herein does not require any pre-knowledge of any dimensions of the optical and mechanical components, and thus can be termed "independent calibration". Furthermore, even any knowledge of the angle formed by the two optical axes (angle of triangulation) is not required.

Figure 9B:
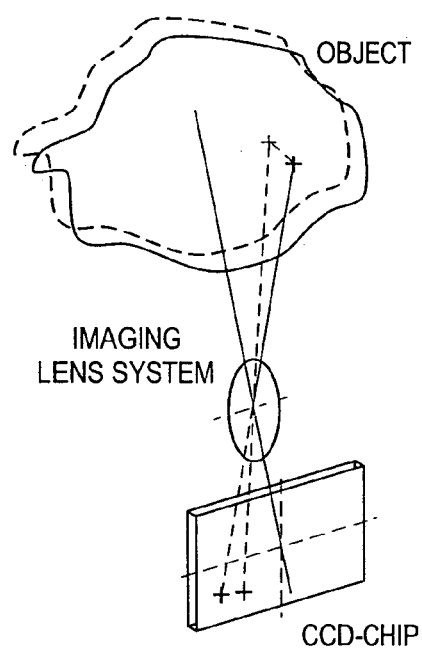
FIG. 9B is an illustration of how the different position of the object reflecting a given ray causes the ray to impinge on a different location of the imaging device (CCD chip).

The background of this procedure can be described best by again just looking at one specific portion of the pattern that is being projected along a ray onto the surface to be measured like indicated in FIG. 9B. It is important to understand that this portion of the pattern will always be projected along this specific ray R, which is defined by the optical characteristics of the lens system and the arrangement of the pattern and the lens system with respect to each other. If this portion of the pattern is being reflected from any surface sitting in the field of view, we can be absolutely sure that this point of the surface will be located somewhere along this ray R. However, we do not know at which position along this ray the point is located. To be able to determine this, the "independent calibration" method basically takes samples. The first sample will be a surface that is located at a certain distance $Z_1$ from the projection device. The reflected portion of the pattern will show up at a specific pixel at the CCD chip (or perhaps over several pixels depending on the size of the portion of the pattern). It is important to understand that every surface that is ever being hit by this ray at this Z-distance will always cause a reflection of this ray R directed to this pixel (we are dealing with diffuse reflection, so every point being reflected will send rays into many directions, regardless of the angle between ray and surface). This implies that every time when this portion of the pattern is being reflected onto the pixel, we know exactly that this point of the surface is located at distance $Z_1$.

Knowledge of the distance between Z and the scanner is not required as long as the scanner will not be used as an absolute measuring system. If we want to use the scanning system as an absolute measuring system, which means that we want to measure the location of points relative to the scanner and not only relative to each other, we would then need to use the Z-values with respect to the origin of the coordinate system of the scanner. The illustrated embodiment is not an absolute measuring system, but nevertheless generates accurate virtual models of the object true to scale.

During the calibration process, we will acquire a plurality of such "samples" for different portions of the pattern reflected off a calibration surface at different Z-distances, where the relative Z-distances of these levels with respect to each other must be known. It will be discussed further below, how many samples will typically be required to receive a complete calibration. The result of this sampling process is the first calibration relationship that is derived for the scanner: (1) pixel coordinates for the electronic imaging device for numerous portions of the pattern, said pixel coordinates associated with distance information from the projection system in a Z direction at at least two different Z distances.

Having this first part of the calibration procedure done, we can determine the Z-component of every part of the measured surface that is reflecting the pattern onto the CCD chip. However, we do not have knowledge of the X- and Y-coordinates. To get this information, we need to perform the second part of the calibration.

Figure 9C:
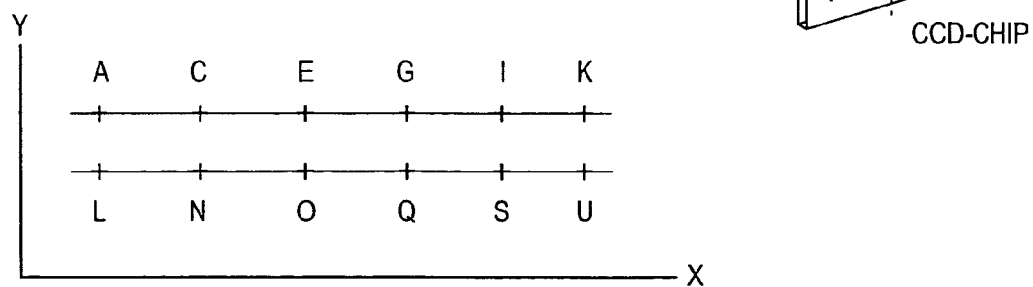
FIG. 9C is an illustration of pixel coordinates in X and Y directions for portions of the pattern (crosses A, L, C, E, G, etc.) at a certain Z distances, with a best fit line or mathematical function connecting the portions together.

Again, we will take "samples", but this time we will not make use of the pattern that is being projected onto the object during normal use of the scanner (the projection unit will be switched off). Rather, images are obtained of a reference object in the field of view that is equipped with features of a known geometry, i.e., known X-Y spatial relationship. The simplest implementation would be a point. In FIG. 9C, such a feature is a plurality of cross-hairs. The feature being projected onto the CCD chip will show up at a specific pixel (or several pixels depending on the size of the feature). The X/Y-coordinates of the pixel at the CCD chip are then assigned to the X/Y-value of the location of the feature (and assigned to a certain Z-distance).

It is obvious that if the feature is being moved in Z-direction, the location of the projection of the reference object at the CCD chip will change. We therefore have a dependence on the Z coordinate, which signifies that the Z-location of the feature must have a known reference to the Z-location(s) of the surfaces that have been used in the first part of the calibration. For instance, such a feature could be located at $Z_1$; other features might be located with a known reference to $Z_1$.

The first feature being captured in this manner would serve as a reference. A certain X- and Y-value (in mm or inches) would be assigned to the location of this feature. If such a feature would be placed close to the optical axis of the imaging system, it would be preferable to assign X=0 mm and Y=0 mm to this location. If we want to use the scanning system as an absolute measuring system, which means that we want to measure the location of points relative to the scanner and not only relative to each other, we would then need to use the X/Y/Z-values of this feature with respect to the origin of the coordinate system of the scanner.

During the calibration process, we will again acquire a plurality of such "samples" at different X- Y- and Z-locations, where the relative X-, Y- and Z-values of the locations of these features with respect to each other and with respect to the Z-values of the first part of the calibration must be known. It will be discussed further below, how many samples will typically be required to receive a complete calibration.

It is important to understand that the determined relationship between the X- and Y-coordinates of any feature being captured and specific pixel coordinates at the CCD chip exists only with respect to the Z-coordinate of the feature. A movement in Z will change the X/Y-value. Therefore, during normal operation of the scanner, when the calibration results are being used to calculate 3D coordinates, we first have to calculate the Z-coordinate of any point on a surface using the calibration values acquired in part 1, and basing on these results we can then perform the X/Y calculation, using the calibration results of part 2 of the calibration process.

There are several options with regard to the number of "samples" to take during calibration and the way how the results may be stored. The most straightforward approach would be to collect pixel coordinates for at least two Z-levels of the projected pattern. The number of pixel coordinates will depend on the resolution of the pattern. The Z-levels will preferably be defined within the depth of focus of the scanner projection lens systems and imaging lens systems, but close to the boundaries of this depth. Having collected pixel coordinates for at least two levels, would allow for interpolation of all other Z-levels. Part 2 of the calibration procedure could also comprise features (points) distributed evenly across the field of view, and those features could again be placed at two different Z-levels, which would allow for an easy interpolation of X- and Y-values. The pixel coordinates acquired in both parts of the calibration process could in the simplest embodiment be stored in a table.

However, this straightforward approach has certain disadvantages. First of all, an apparatus is required. Otherwise it would not be possible, to place the surfaces required for part 1 in a controllable manner with respect o each other, and the features being captured in part 2 also need to be precisely placed with respect to each other and to the calibration surface used in part 1. Usage of such a calibration apparatus is not a problem within an industrial production environment. But if scanners need to be calibrated for instance in an orthodontic office, it is not recommendable to always ship such a device to the location.

But there is no need to calibrate each portion of the pattern in various Z-levels. If a device is used, that comprises surfaces at different Z-levels, portions of the pattern will be projected onto levels that are closer to the scanner, and portions will be projected onto levels that are further away. It is well possible, to interpolate also the pixel coordinates that are not acquired during calibration.

Assuming that portions A and C of the pattern will be projected onto level $Z_1$, while portions C and D will be projected onto level $Z_2$, we will receive pixel coordinates for portion A and C assigned to Level $Z_1$ ($x_{A1}$ and $y_{A1}$ for A, $x_{C1}$ and $y_{C1}$ for C) and pixel coordinates for portion B and D assigned to Level $Z_2$ ($x_{B2}$ and $y_{B2}$ for B, $x_{D2}$ and $y_{D2}$ for D). It is well possible to linearly interpolate for instance $x_{A2}$ (which has not been acquired) from $y_{B2}$ and $y_{D2}$. In the same manner $y_{B1}$ could be interpolated from $y_{A1}$ and $y_{C1}$. Another way to receive calibration values that have not been acquired directly would be to draw the acquired pixel coordinates for a certain Z-level onto a sheet of paper and then to construct a best-fit line (either straight or curved) through those points. If the mathematical function of this best-fit line is stored, the pixel coordinates can be calculated using that function instead of storing them separately. The operation of determining a best-fit line can of course also be done directly in the computer. The best fit line concept is illustrated in FIG. 9C.

This procedure would work as well for part 2 of the calibration procedure where pixel coordinates are being acquired for specific features assigned to X-, Y- and Z-values. Again only a subset of features has to be captured at each Z-level, and the remaining values can be interpolated in the way described above. It would therefore also be possible to use just one calibration device that provides surfaces at least two Z-levels to perform part 1 of the calibration and comprises features at those surfaces that allow for part 2. The density of portions of the pattern, i.e., features to be captured, depends on the optical quality of the components of the scanner. We should capture at least four portions of the pattern, preferably close to the corners of the CCD imaging device 56 to provide a reliable interpolation.

The advantage of this calibration process is that it requires absolutely no pre-knowledge of the mechanical and optical characteristics of the scanner and automatically compensates for irregularities of the optical components, this including the CCD chip and the pattern. It is therefore useful to calibrate scanners that are made from cheap parts, and in can be used on scanners that have no known relationship between the imaging and the projection device.

With the foregoing discussion of the principles of the invention in mind, a representative embodiment of a scanner calibration device and method will be described with particularity with reference to FIG. 8. The presently preferred scanner calibration system includes mount or holder 122 for holding the scanner fixed in position during calibration. The holder is affixed to the top of a table 124. A calibration apparatus is positioned directly in front of the scanner 14. The calibration apparatus consists of a Z-direction carrier 126 having one portion 128 fixedly mounted to the table and a second portion 130 which can move back and forth in the Z direction between two different positions Z1 and Z2. An X-direction carrier 131 is mounted to the moveable portion 130 of the Z-direction carrier. The X-direction carrier consists a first portion 132 which is mounted to the moveable portion 130, and a second portion 134 which is moveable in the X direction relative to the first portion 132, as indicated.

The X-direction carrier 131 has mounted to its upper surface 136 two calibration devices: (1) a smooth, planar calibration surface 138 used for calibration of the scanner in the Z-direction, and (2) an X-Y calibration surface 140 used for calibration of the scanner in the X and Y direction. The X-direction carrier also contains a light 142 for providing back illumination of the X-Y calibration surface 140.

To calibrate the scanner 14, carriers 126 and 131 are moved such that the Z-direction calibration surface 138 is positioned in front of the scanner 14. An image is taken of the projection pattern reflecting off the surface with the surface 138 at some arbitrary distance Z1 from the scanner. Then the carrier 130 is moved a distance away (ΔZ) to a new position Z2, and a second image is taken. Pixel addresses where the specific locations of the pattern are imaged in the electronic imaging device are determined and stored in a calibration table in a memory. The distance ΔZ is also known precisely and stored in the scanner memory or in the computer that performs the scanner calibration.

Then, the carriers 126 and 131 are moved such that the X-Y calibration grid 140 is placed at the distance Z1 and an image is taken. The image is generated by activating the source 142, with light from the source 142 passing through numerous tiny apertures 143 in the calibration surface 140 and impinging on the electronic imaging device 56. (The pattern illumination source is not used in this part of the calibration). The carrier portion 130 is moved to the position Z2, and another image is generated. Using the known separation distance between points in the X-Y calibration grid 140, X and Y distance information for points in the pattern imaged in the first part of the calibration procedure is computed. The results are stored in the calibration table. This process is described in further detail below. When the scanner calibration is finished, the scanner serial number and scanner calibration table (or other representation of the calibration relationship, such as a set of mathematical equations) are stored in memory in the scanner or in a computer associated with the scanner that processes the scanned images.

Figure 8A:
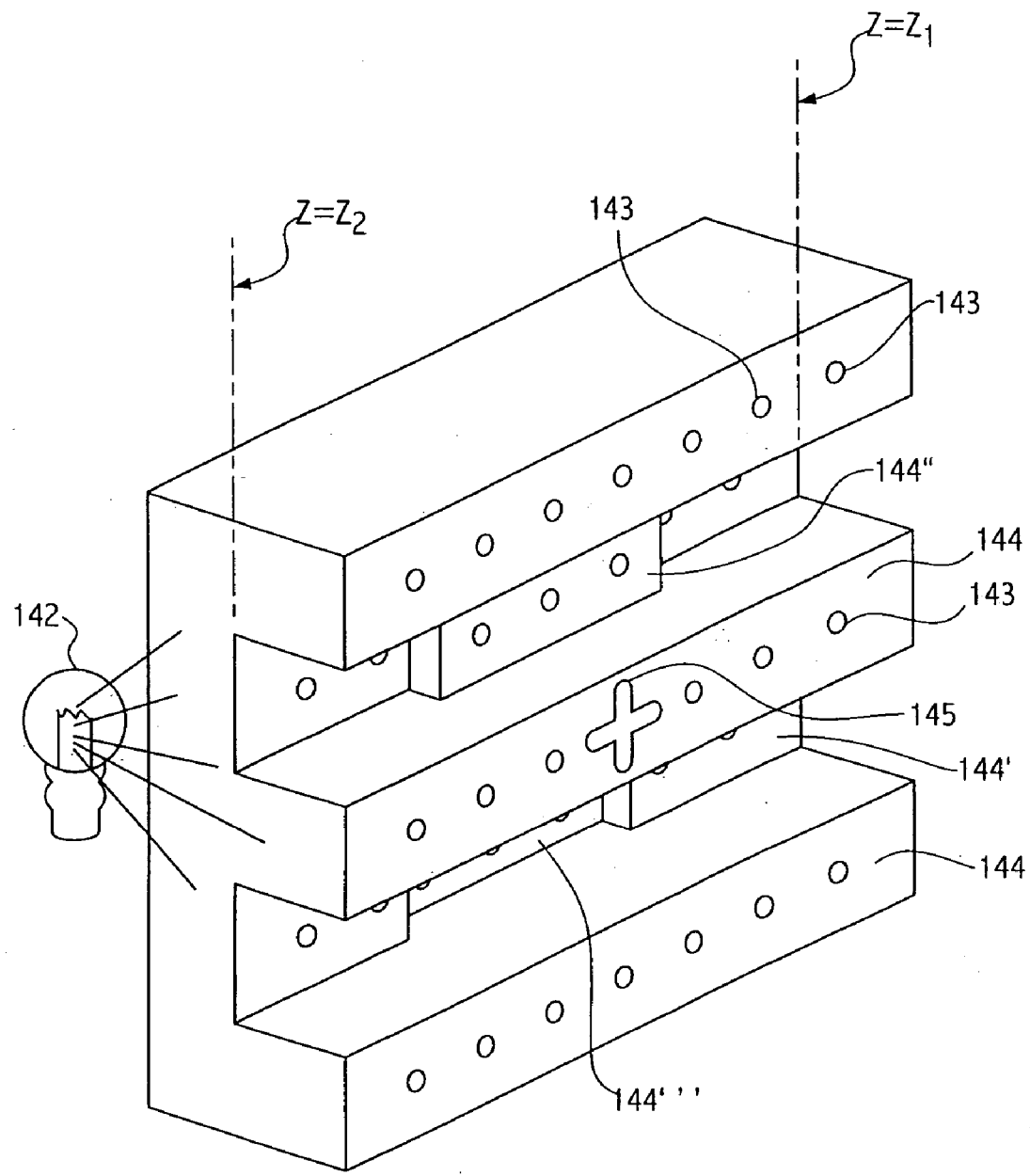
FIG. 8A is a perspective view of an alternative embodiment of a calibration device for the scanner in which the Z direction and X-Y calibration surfaces of FIG. 8 are combined into a single surface.

An alternative configuration of the calibration surfaces is shown in FIG. 8A. The calibration device consists of a set of reflective, planar, parallel planes 144, 144', 144" and 144''', of known distance from each other and from the scanner, with apertures 143 spaced at known distances along the surfaces of the planes and at known distances from adjacent planar surfaces. A cross feature 145 at the center forms the origin of the calibration surface, and is used as explained below. Two of the surfaces 144, 144', 144" and 144''' are used for the Z calibration surface. For X and Y calibration, the backlighting illumination source 142 is activated and light passes through the apertures 143 onto the electronic imaging device. The entire two-dimensional focal plane of the electronic imaging device is calibrated from an interpolation of known points in the surfaces 144, 144', 144" and 144''', in accordance with teachings described in detail herein. The embodiment of FIG. 8A is considered more cumbersome than the embodiment of FIG. 8, but is offered to illustrate that other configurations for a calibration surface are possible. In fact, curved surfaces or sloping surfaces could even be used, but the simplest surface is a planar surface oriented directly at the electronic imaging device.

Thus, in one possible alternative embodiment of the invention a calibration device is provided for a scanner projecting a pattern onto an object and receiving a reflection of the pattern off the object. The calibration devices comprise a calibration surface 144 receiving said projected pattern comprising two or more parallel surfaces (e.g., 144 and 144") of known separation distance and spatial extent and a plurality of point sources of light 143 provided in the two or more parallel surfaces. As described herein the point sources of light are apertures which allow light to pass through the surfaces 144 from the light source 142, but other configurations are possible. For example, the point sources of light could be light emitting diodes arranged in an array in the surface 144. The apertures 143 are formed in a precise and known spatial relationship relative to each other, such as by forming the holes with a precision high powered laser on a sheet of metal. Alternatively, instead of apertures 143, black dots could be formed on paper using a highly accurate printing process, and the black dots imaged by the CCD 56.

The calibration procedure described herein represents an alternative, and more preferred way of computing three-dimensional information for images as compared to prior art methods. FIG. 9 is an illustration of the relevant parameters that can be used to calculate surface configuration of the object in accordance with a known fashion. The method of FIG. 9 requires knowledge of the separation distance D or baseline between the detector and the light source, the angle between the axes 48 and 58, and the angles α and β shown in the Figure. The present calibration method and method of calculation of three-dimensional information does not require any of this information. The calibration procedure compensates for imperfections in the optics in the optical paths, and therefore eliminates the need for high precision optics. Further, there is no need for precise knowledge of the placement of the scanner relative to the calibration planes. There is no need to know the angle between the axes 48 and 58, the separation distance between the scanner and the object being scanned, or any absolute value of the location of the object in any global coordinate system. The scanner allows for truly reference independent scanning, yet it gives very precise description of the three-dimensional surface.

The calibration will typically be performed once during manufacturing, which should be enough to last the life of the scanner. However the scanner can simply and quickly re-calibrated if the need arises.

Figure 10:
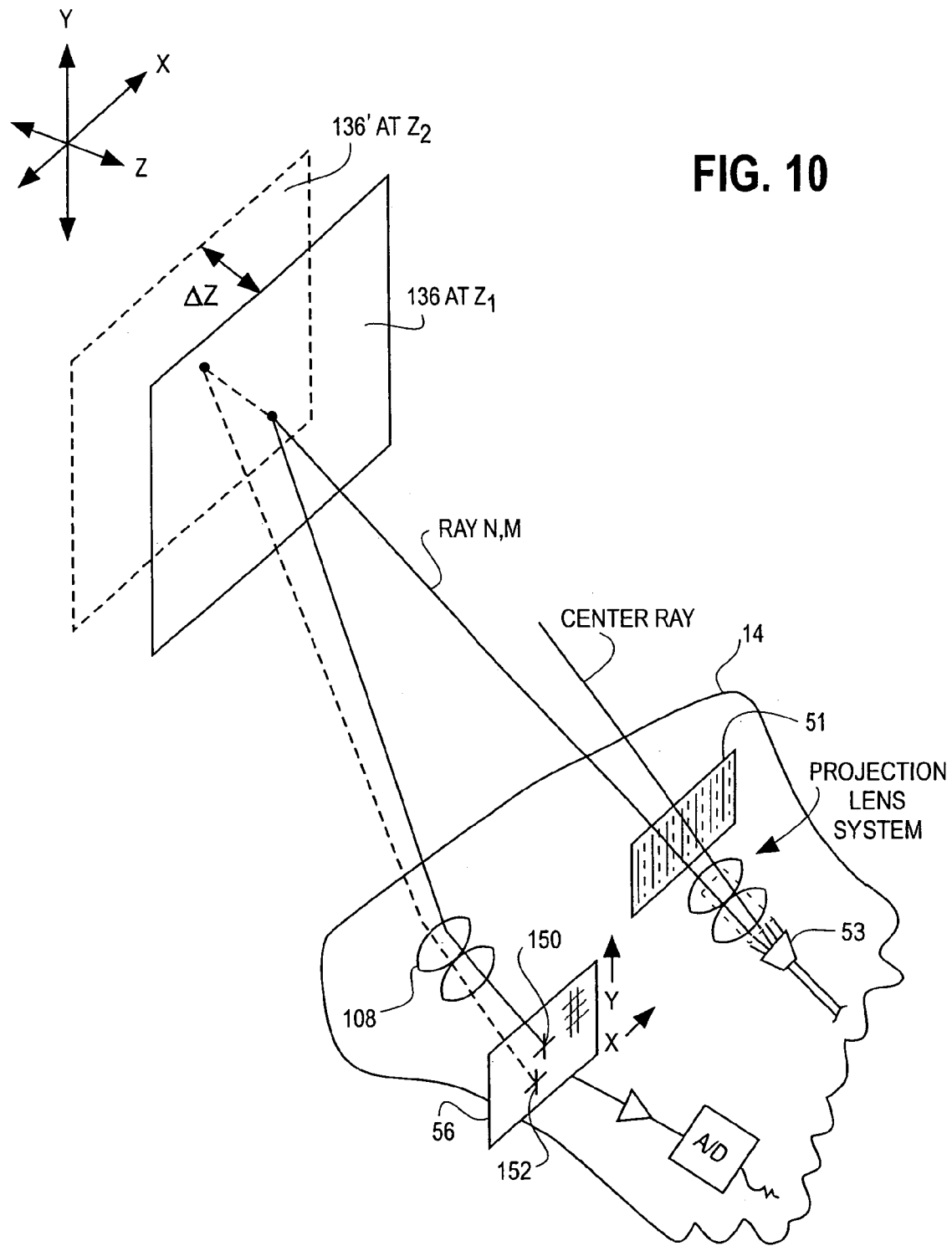
FIG. 10 is a illustration of an arbitrary ray $R_{n,m}$ which is projected from the projection system onto a calibration surface and captured by the electronic imaging device, with the calibration surface positioned at two different distances from the scanner, Z1 and Z2 and separated by a distance ΔZ.

A representative example of the calibration of the scanner will be better understood from FIG. 10 and the following discussion. FIG. 10 is a illustration of an arbitrary, unique ray $R_{n,m}$ which is projected from the projection system of the scanner onto the smooth, planar calibration surface 138 of FIG. 8 during the first part of the calibration procedure. The ray $R_{n,m}$ is captured by the electronic imaging device 56, with the calibration plane positioned at two different distances from the scanner, Z1 and Z2. The distance between the two locations is ΔZ. Distance Z1 need not be known, however the separation distance ΔZ is known. The separation distance ΔZ will vary depending on the depth of focus of the imaging optics 108 in the scanner 14.

FIG. 10 illustrates a fundamental principle of the technique that is used for calibration of the scanner and generation of three-dimensional information of an object, which is considered to be an improvement over the calculations required by the method of FIG. 9. FIG. 10 illustrates that when the plane 136 is at a distance Z1, the ray $R_{n,m}$ impinges on the imaging device at the location 150. When the calibration surface 136 is moved to position Z2, the ray $R_{n,m}$ impinges on the detector at point 152. The pixel coordinates for ray $R_{n,m}$ at both positions is stored in a calibration table. In actuality, the pixel coordinates for a large number of rays from the projection pattern are stored for Z1 and Z2. These pixel coordinates, along with X and Y dimension measurements from a second part of the calibration procedure, give all the information needed to create a calibration table necessary to compute three-dimensional coordinates for an object that has been scanned with the projection pattern.

Ray $R_{n,m}$ corresponds to a single point in the projection pattern. Knowledge of where in the projection pattern ray $R_{n,m}$ originated from is required. Hence, some pattern recognition and decoding of the detected pattern is needed to identify the specific portions of the pattern that are being imaged by the various portions of the CCD electronic imaging device. To understand the pattern recognition process, the reader is directed to FIGS. 11, 12, 17, 18 and 19 and the following discussion.

Pattern Recognition

Figure 11:
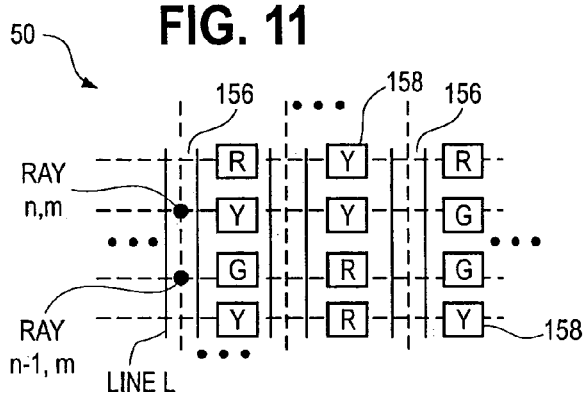
FIG. 11 is an illustration of a portion of a pattern that is projected from the scanner of FIG. 3 onto an object, the projection pattern comprising an array of parallel lines separated from each other by colored dots, it being understood that other types of projection patterns are possible.
Figure 12:
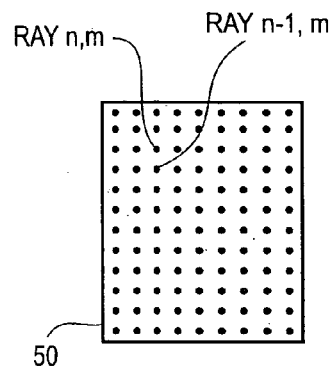
FIG. 12 is an illustration showing that the various rays of the projection system through the pattern of FIG. 11 can be represented by an array of N×M points.

FIG. 11 is an illustration of a portion of a pattern that is projected from the scanner of FIG. 3 onto an object (including the calibration surface 138). The projection pattern comprises an array of parallel lines 156 separated from each other by red, green and yellow colored dots 158, it being understood that other types of projection patterns are possible. The sequence of the colored dots 158 vary along the length of the lines 156, and in the direction perpendicular to the lines. This technique is used such that using pattern recognition and decoding processes, described herein, every region in the projection pattern can be decoded from the pixel data from the imaging device. FIG. 11 illustrates that $Ray_{n,m}$ can be taken to have originated at the intersection on one particular line and one particular colored dot, and this location can be determined precisely form the pattern recognition and decoding process. Similarly, the ray along the line L one row below ray $R_{n,m}$ can also be identified. In the present example, the pattern is constructed such that there are N columns or lines, and M rows of colored dots. FIG. 12 illustrates showing that the various rays of light passing through the pattern of FIG. 11 can be represented by an array of N×M points.

Figure 14:
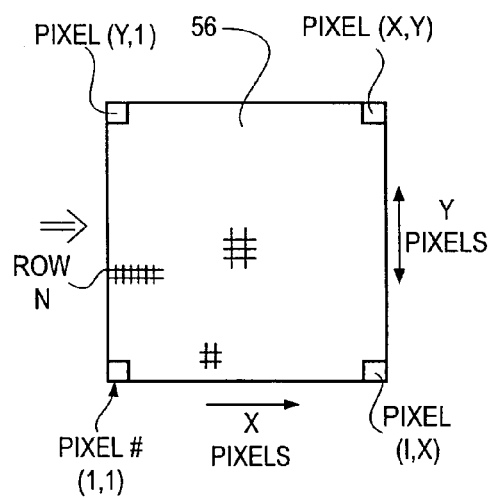
FIG. 14 is an illustration of the electronic imaging device, comprising an array of pixels arranged in X columns and Y rows.

This array of points representing the projection pattern of FIG. 11 is imaged by an electronic imaging device or CCD 56 arranged in an array of row and columns, as shown in FIG. 14. There are X columns of pixels in the X direction and Y rows of pixels in the Y direction. In the illustrated embodiment there are 1,028 pixels in each direction.

Figure 17:
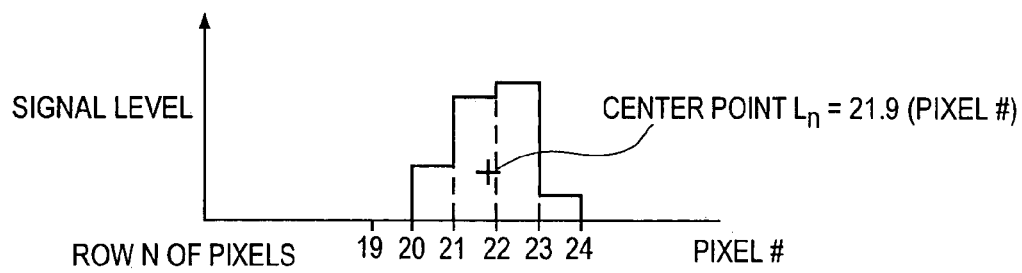
FIGS. 17, 18 and 19 illustrate the pattern recognition process for captured two dimensional images, as a first step in deriving three-dimensional information as to the object.
Figure 18:
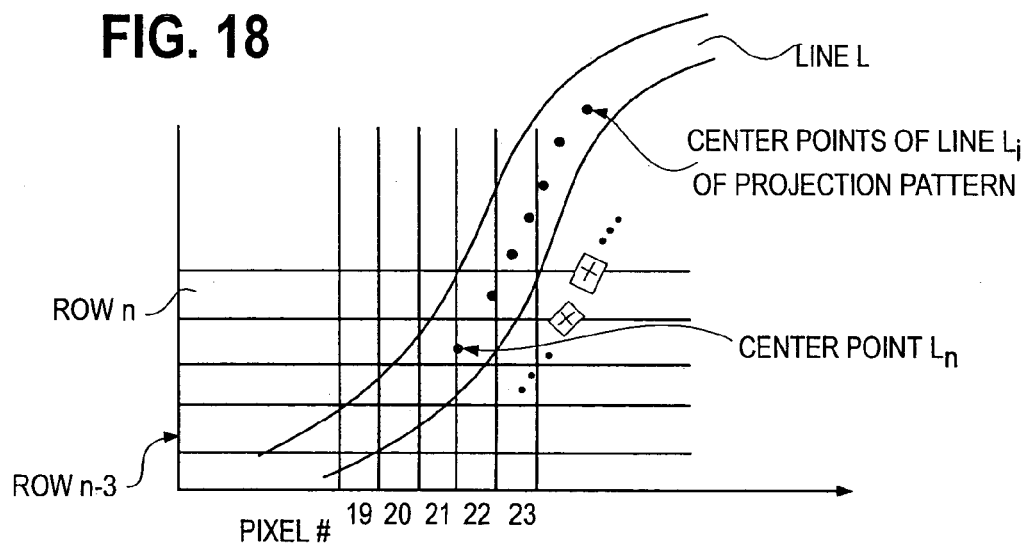
Figure 19:
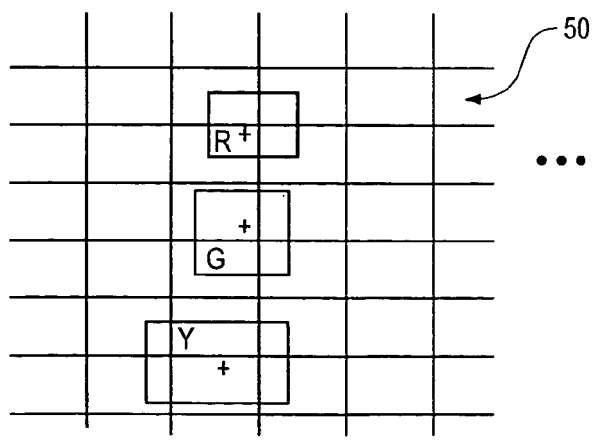

FIGS. 17, 18 and 19 illustrate the pattern recognition process for captured two-dimensional images. FIG. 17 shows the signal level from one row of pixels in the electronic imaging device. The signal indicates that line L of the projection pattern is imaged at pixels 20–23 of a particular row of the pixels. Averaging of the pixel values over the four pixels allows the center point of the line relative to pixel 21 to be calculated, with sub-pixel resolution. FIG. 18 shows how the line L and adjacent colored dots are imaged on the surface of the imaging device in this example. Note that the line is not necessarily centered over any column of pixels and hence the averaging must be performed to determine the center point in the line. A similar pattern recognition process is performed for the colored dots, as indicated in FIG. 19. The center of each colored dot is located, as is the center points of the lines for every line and colored dot imaged by the imaging device.

The pattern recognition process thus takes the output signals of the imaging device (in the form of a colored bitmap image) and returns a set of pixel locations for centers of lines and centers of particular colored dots. The next step in the process is correlating these pixel locations for lines and colored dots to particular lines and colored dots in the projection pattern. This process is referred to as decoding (process 82 in FIG. 6), and is described in detail below. Decoding is not normally needed during the calibration procedure described in conjunction with FIG. 8, since the Z calibration surface is planar and the arrangement of the projection pattern on the CCD 56 is preserved. Decoding is used however during use of the scanner to scan an object of unknown surface configuration.

Decoding

The decoding process is the process of converting a set of pixel addresses for lines imaged by the imaging device, and a set of pixel addresses for particular colored dots imaged by the imaging device, to particular lines and colored dots in the projection pattern. Decoding is not absolutely required during calibration (particularly where the Z calibration surface is a planar surface). It is used, however, during processing of images on an object having undercuts, shadow features, or other irregularities. It may be possible to decode only a portion of the received pattern, since ordering of lines in the projection pattern is preserved. For example, if lines 13 and 16 are decoded, lines 14 and 15 are also decoded since their spatial relationship relative to lines 13 and 16 are preserved.

The imaging analysis process needs to know that a particular pixel is imaging a particular line or a particular colored dot. The projection pattern or screen 50 (FIG. 2) varies continuously in both directions, due to the unique and continually varying sequence of the colored dots. The decoding process simply examines where the red, yellow and green dots are being imaged in the imaging device, and compares these results with the known sequence of red, yellow and green dots in the projection pattern, and thereby locates or identifies each ray with reference to the projection pattern. For example, the process knows that, for example, pixel 21 in row N of the imaging device is imaging the center of line 13, row 55, in the projection pattern.

Referring again to the calibration set-up of FIGS. 8 and 10, the scanner takes two images of the Z-calibration surface 138, one at distance Z1 and the other at distance Z2. The pixel addresses where each ray $R_{n,m}$ in the projection pattern is imaged by the array is stored in a calibration table referred to herein as calibration table #1, shown in FIG. 24. At this point, we know how the imaging of the projection pattern varies as the calibration surface is moved in the Z direction relative to some imaginary plane Z1 in front of the scanner. However, the X and Y relationship is not yet known. Therefore, the scanner must be calibrated in the X and Y direction using a pattern of known geometry. This is explained in conjunction with FIGS. 8 and 13–16.

Figure 13:
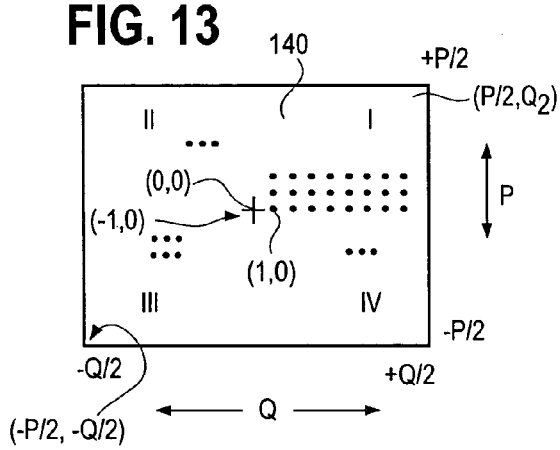
FIG. 13 is a illustration of the X-Y calibration surface of FIG. 8, showing the array of Q×P points in the calibration surface being organized into a coordinate system having an origin at the center of the surface and breaking the surface up into four quadrants I–IV.
Figure 23:
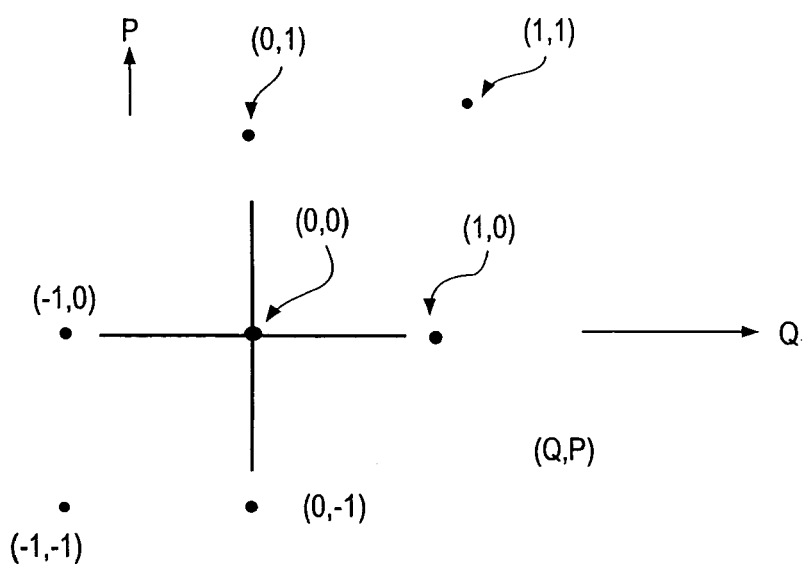
FIG. 23 is an illustration showing the coordinate system that used for the X-Y calibration surface in generating the entries for the calibration tables for the scanner.

FIG. 13 is a illustration of the X-Y calibration surface 140 of FIG. 8, showing the array of Q×P points (tiny apertures 143) in the calibration surface 140 being organized into a coordinate system having an origin at the center of the surface 140, in the shape of a cross 145. The calibration surface 140 is conceptualized as consisting of four quadrants I–IV. FIG. 23 shows one possible numbering convention of the points in the surface at the origin. In the illustrated embodiment, the points of the X-Y calibration surface 140 are actually tiny apertures spaced from each other a known distance (e.g., 1 mm). The apertures act as a plurality of point sources of light when the light source 142 positioned behind the surface 140 is activated. These points of light are imaged by the electronic imaging device 56 during the second part of the calibration step. By counting pixel signals (indicating the imaging of a point source in the surface 140) over from the origin in the X and Y directions, it is possible to determine which point in the surface 140 is being imaged by which pixel, again with subpixel resolution. Since we know the address of the pixels which illuminate the specific portions of the projection pattern, and we can know the distance from the origin of the surface 140 that this pixel is imaging, it is therefore possible to calibrate the pixels in the X and Y directions. A second calibration table, shown in FIG. 25, is used as an interim step to generate the distance values in the X and Y directions for the principal calibration table #1 in FIG. 24.

Figure 15:
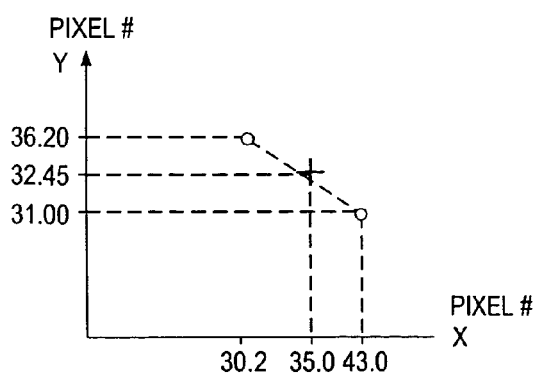
FIG. 15 is an illustration showing the interpolation of pixel addresses in X and Y directions for given ray $R_{2,3}$ from a scanned object from two points of the X-Y calibration plane previously imaged by the electronic imaging device during calibration.
Figure 21:
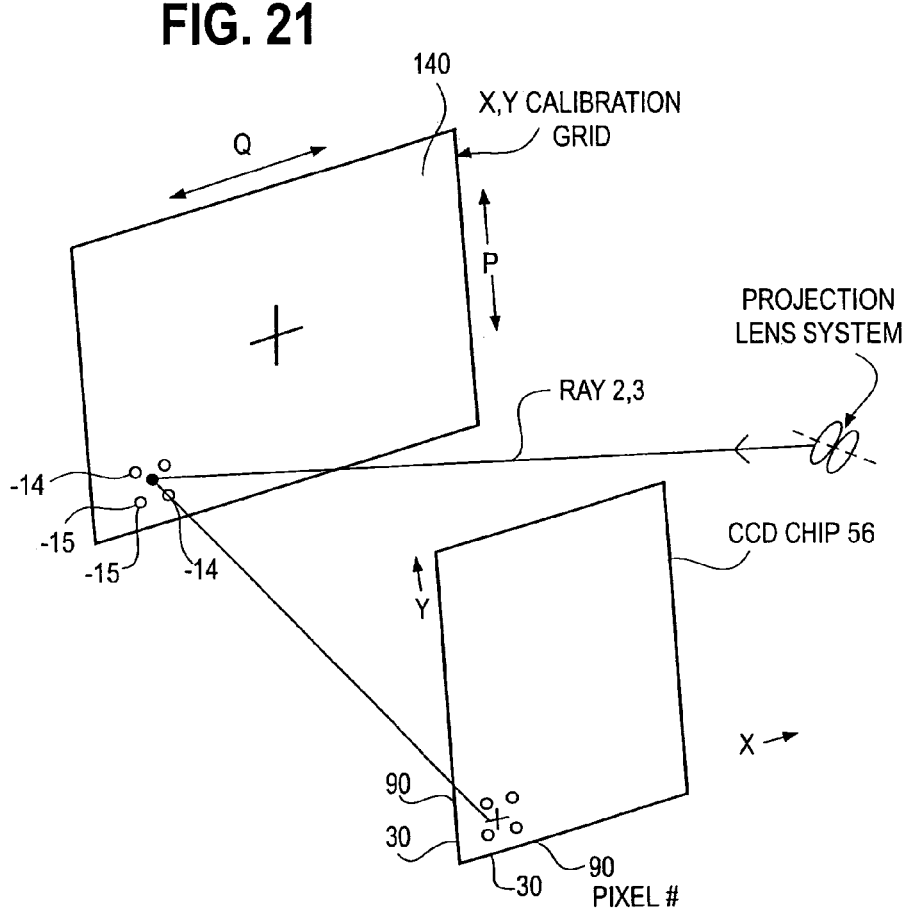
FIG. 21 illustrates the relationship between the projection of ray R 23 from the projection system and the X-Y calibration surface of the calibration station.

This process will be explained by example. FIG. 15 is an illustration showing the interpolation of pixel addresses in X and Y directions for a given ray $R_{2,3}$ from a scanned object from two points of the X-Y calibration plane previously imaged by the electronic imaging device during calibration. FIG. 15 indicates that a given point in the projection pattern, ray $R_{2,3}$, is imaged by some pixel that is located between the pixels that imaged points in surface 140 that are in quadrant III, between 14 and 15 points to the left of the origin and between 14 and 15 points below the origin. This is suggested by FIG. 21, which shows where ray $R_{2,3}$ is imaged on the CCD chip. FIG. 21 also indicates where the corresponding points on the X-Y calibration surface 140 are imaged by the pixels in the electronic imaging device. As is shown in FIG. 21, in the present example the pixel values are between 30 and 90 in the X and Y directions.

FIG. 25 shows the X-Y calibration table #2 that is used for generating distance entries in X and Y directions in the calibration table No. 1 shown in FIG. 24. FIG. 25 illustrates that for each point in the X-Y calibration surface 140, corresponding pixel addresses for pixels imaging those points are identified and stored in the table. This is done for all points in the four quadrants of the X-Y calibration surface 140. These values are obtained when the X-Y calibration surface is positioned at both distances Z1 and Z2, and an image is generated at both positions. The entries in the table are pixel addresses in X and Y directions, expressed in sub-pixel resolution. Representative entries for Quadrant I are shown, it being understood that entries are made for all the points in the X-Y calibration surface.

Now, if we know that ray $R_{2,3}$ of the projection pattern from the Z-calibration procedure (using the calibration surface 138) is being imaged at a particular location, we can use the calibration table #2 of FIG. 25 to compute an entry in mm for table #1. Again, using the present example, assume ray $R_{2,3}$ (corresponding to line 2, row 3 in the projection pattern) is imaged by pixel having an address of 30.2 in the X direction and 36.2 in the Y direction, at Z=Z1. The distance in mm can be calculated from an interpolation of the entries in calibration table 2 of FIG. 25. This is indicated for the entries in line 2, row 3. At the Z=Z1 distance, this point is imaged at pixels 30.2 in the X direction and 36.2 in the Y direction, which corresponds to a distance of −14.6 mm in the X direction from the origin and −14.4 mm in the Y direction. Similarly, at Z=Z2, this point is imaged by pixels 43.0 in the X direction and 31 in the Y direction, which corresponds to a distance of −14.8 mm in the X direction and −15.8 mm in the Y direction. This information is entered into table #1, as shown in FIG. 26.

Figure 22:
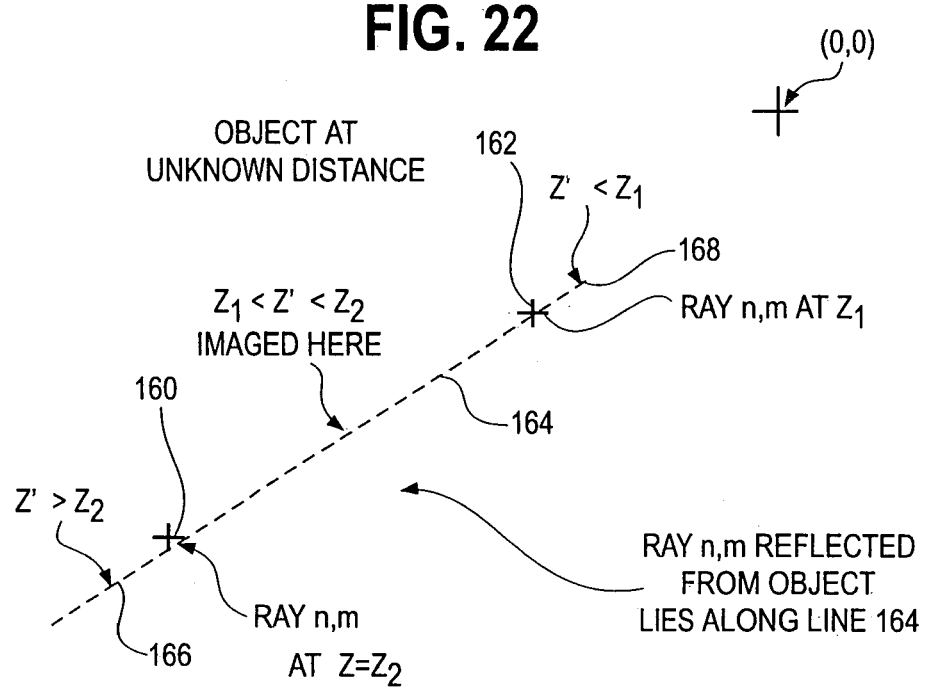
FIG. 22 is an illustration showing the relationship between the unknown distance Z' of the object from the scanning device and the locations where ray $R_{n,m}$ is imaged by the electronic imaging device at distances $Z_1$ and $Z_2$.

This interpolation takes advantage of a linear relationship that exists between pixel address and distance for objects at an unknown distance Z' from the scanner. This can be best appreciated from FIG. 22. Since we know that ray $R_{n,m}$ is imaged at one point 160 in the imaging device at Z=Z1, and that it is imaged at another point 162 at distance Z=Z2, the ray must fall along the dotted line 164 where Z' is between Z1 and Z2. Similarly, if Z'>Z2 it lies along the line indicated at 166. If Z'<Z1, it lies along line 168. This linear relationship between distance and pixel address is the key to obtaining Z information as to ray $R_{n,m}$ and X and Y distance in mm. Furthermore, since ΔZ is known exactly during the calibration (e.g., 7 mm in the illustrated embodiment), and a linear relationship exists between pixel address and distance, the location of exactly where ray $R_{n,m}$ lies along the line 164, 166 or 168 tells us with precision the position of the unknown object in the Z direction, relative to virtual plane Z1. This location of where ray $R_{n,m}$ is being imaged by the electronic imaging device is arrived at by the pattern recognition and decoding processes described herein.

Figure 16:
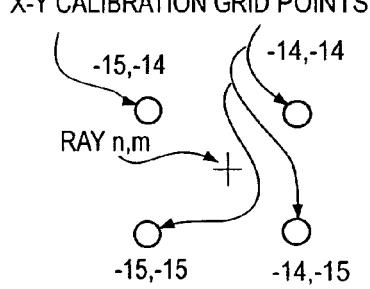
FIG. 16 is a more detailed illustration of the location of the ray $R_{2,3}$ from the scanned object relative to the points of the X-Y calibration plane.

Referring again to the example of FIGS. 16 and 17, we know ray $R_{n,m}$ is imaged at some region of the CCD, and this is stored in table 1 (FIG. 25). From calibration table 2 (FIG. 26) we know the X and Y coordinates of neighboring points in the X-Y calibration grid in the region of ray $R_{n,m}$. By interpolation of the X and Y coordinates, we can calculate the distance in mm from the origin since the points in the X-Y calibration grid are separated from each other a known distance. This is done for all N×M portions of the projection pattern.

For example, calibration table 1 of FIG. 24 tells us that ray $R_{2,3}$ is imaged at pixel addresses X=30.3 and Y=36.2 for Z=Z1, and at pixel address X=43 and Y=31 at Z=Z2. We then look to the table 2 entries (FIG. 25) to find the closest X and Y points in the X-Y calibration grid by looking at the pixel addresses in table 2. This is shown in FIG. 16. An interpolation of the pixel addresses in table 2 to the known pixel address from table 1 results in an X, Y address in mm. In the present example, X in mm=−14.6, Y in mm=−14.4. The results are now added to table 1, see FIG. 26. The same is done for the distance Z=Z2. The same is of course performed for all the N×M rays in the projection pattern, resulting in a completely filled calibration table 1. Table #1 in FIG. 26 only shows the entries for ray $R_{2,3}$, but the process is done for all rays for Z=Z1 and Z=Z2.

Figure 20:
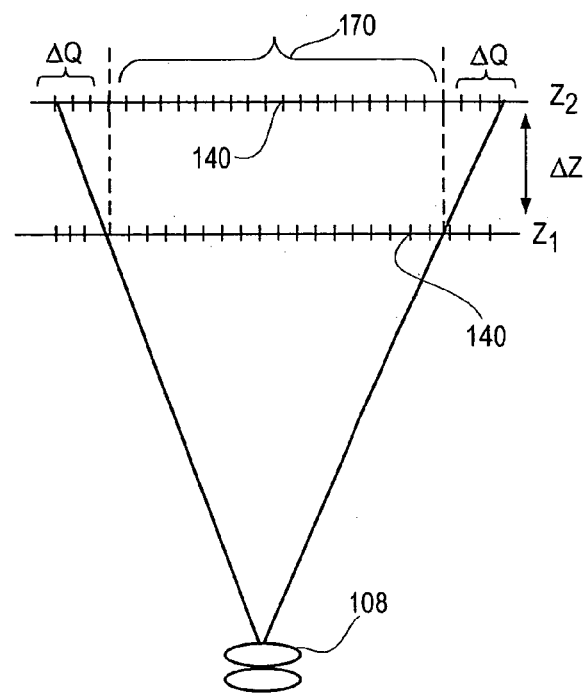
FIG. 20 illustrates the points of the X-Y calibration plane from the calibration station of FIG. 7 at two positions relative to the optical elements of the electronic imaging device.

FIG. 20 illustrates the points of the X-Y calibration plane from the calibration station of FIG. 7 at two positions Z1 ands Z2, relative to the optical elements of the electronic imaging device. It will be apparent that when the Z=Z1, some points in the X-Y calibration plane will not be imaged, but will be when Z=Z2. These points, indicated by ΔQ in the Q direction, exist also in the P direction. The calibration table 2 takes these into account. Some points in all four quadrants may not be imaged at Z=Z1, but will be imaged at Z=Z2 during X-Y calibration. Points indicated at 170 are imaged at both values of Z.

From the above, in one aspect of the present invention, a machine-readable memory is provided for a scanner used to calculate three dimensional information of an object scanned by the scanner. The memory may be in the scanning unit itself, in a separate work station for the scanner, or in any computing device such as a remote computer that processes acquired image data and generates a three-dimensional model of the object. The memory comprises an array of data storage locations containing a calibration relationship for the scanner, such as a table. The calibration relationship identifies pixel coordinates for numerous portions of a pattern projected onto a calibration surface located at two different distances from the scanner, and distance information in X and Y directions for the portions of the pattern for the two different distances. The calibration entries stored in memory allow the scanning system to compute three-dimensional coordinates for points on an object reflecting the projection pattern onto the electronic imaging device.

Now that the scanner has been completely calibrated, it is ready to scan objects at some unknown distance and having some unknown surface configuration. The derivation of X, Y and Z coordinates for the surface will be explained in the next section.

Derivation of 3-D Point Cloud per Image (step 84. FIG. 6)

With reference to FIGS. 6 and 26, we now explain the derivation of spatial coordinates in three dimensions for a single captured image. With the entries in Table 1 completely filled out during calibration, the scanner is now able to derive X, Y and Z coordinates for any object at an unknown distance. The scanner has the most accuracy when the distance is between the values Z1 and Z2, such that the captured images are in focus, but distances outside of this range may still be able to be imaged and decoded.

First, the electronic imaging device 56 captures an image and the image is subject to the pattern recognition and decoding, steps 80 and 82 in FIG. 6, described in detail above. This process results in a set of pixel coordinates stored in memory for all the lines and colored dots of the pattern that are projected onto the object and imaged by the pixels of the CCD. Comparison of the pixel addresses of the captured image with the entries in Table 1 in FIG. 26 (when completely filled out during calibration) yields the coordinates of every point in the captured imaged, in three dimensions.

The process is as follows:

First, compute the Z value of every portion in the projection pattern found in the captured image using table 1, given the known line and row number of the portion of the pattern, and the associated pixel number. The unknown distance, Z', for any point, measured from the virtual plane Z1 is as follows $$Z' \text{ (in mm)} = \Delta Z \times \frac{\text{measured pixel \#} - \text{pixel \# for line and row of pattern at } Z1}{\text{pixel \# for line and row of pattern at } Z2 - \text{pixel \# for line and row of pattern at } Z1}$$

where ΔZ is the distance from Z1 to Z2 in the calibration set up described above.

Using ray $R_{2,3}$ as an example, if this ray is imaged at pixel #35 in the X direction, from table 1 the calculation is as follows $$Z' \text{ (in mm)} = 7.0 \text{ mm} \times \frac{35 - 30.2}{43 - 30.2} \quad \text{where } \Delta Z \text{ is 7 mm}$$

$$= \Delta Z \times \sigma \qquad \text{Here, } \sigma = 0.375, \text{ a linear scaling factor.}$$

Therefore Z'=0.375×7 mm or 2.625 mm. The point on the object reflecting ray $R_{2,3}$ is 2.625 mm from the virtual plane Z1. The Z value for all other points in the object are also measured relative to a virtual plane Z1.

Now, Table 1 (FIG. 26) is referred to determine the mm values in the X and Y direction for this point in space and another interpolation is performed to the mm entries in table 1. The calculation is as follows:

Since we know we have line 2, row 3 in the pattern (from the pattern recognition and decoding process), we need to interpolate the mm entries in table 1.

X value is between −14.6 and −14.8 ΔX=0.2 mm

Y value is between −14.4 and −15.8 ΔY=1.4 mm

The true value of $X = X_{at\ Z1} - (\sigma \times \Delta X)$, similarly the true value of $Y = Y_{at\ Z1} - (\sigma \times \Delta Y)$.

Therefore:

The true value of X for ray $R_{2,3}$=−14.6−(0.375×0.2)=−14.675 mm

The true value of Y for ray $R_{2,3}$=−14.4−(0.375×1.4)=−14.925 mm

Summarizing, the X, Y and Z coordinates for the point in the object reflecting ray $R_{2,3}$ is X=−14.675 mm Y=−14.925 mm Z=−2.625 mm These points are stored in memory 42 of the scanning work station 16, step 86 of FIG. 6. This process is performed for every ray $R_{n,m}$ in the projection pattern that is recorded in the captured image. The result is a set of three-dimensional coordinates in space, referred to herein as a "frame", for each captured image. This set of points can be calculated in a small fraction of a second with a general-purpose computer.

The pattern recognition, decoding and 3-C coordinate calculation process will now be explained with reference to two-dimensional bitmap images of teeth. The process described below is the same for any object being scanned.

Part 3. Generation of Digital Impression

A complete three-dimensional model of the patient's dentition can be generated from the scanning system of the present invention. The process requires an operator moving the scanner 14 (FIG. 3) over the dentition, preferably in-vivo, and generating a series of frames of images. The frames are obtained at a rate of at least one frame per second as the scanner is moved over the teeth. The scanning of an entire jaw may require three separate scanning operations or "segments" due to maneuverability constraints and a break in the capturing of images. While the scanning is occurring, the four steps of FIG. 6 are performed for the stream of captured images. The end result is the storage of a set of frames in the main memory of the scanning work station 16. The frames can be registered to each other using one or more of a using a variety of frame registration techniques described in detail below. Once all the frames have been registered to each other, a complete three-dimensional virtual model of the patient's dentition is displayed for the orthodontist. This computer model provides a base of information for diagnosis and planning treatment. An introduction to the treatment planning aspects of the overall orthodontic care system is set forth in Part 4.

Figure 27:
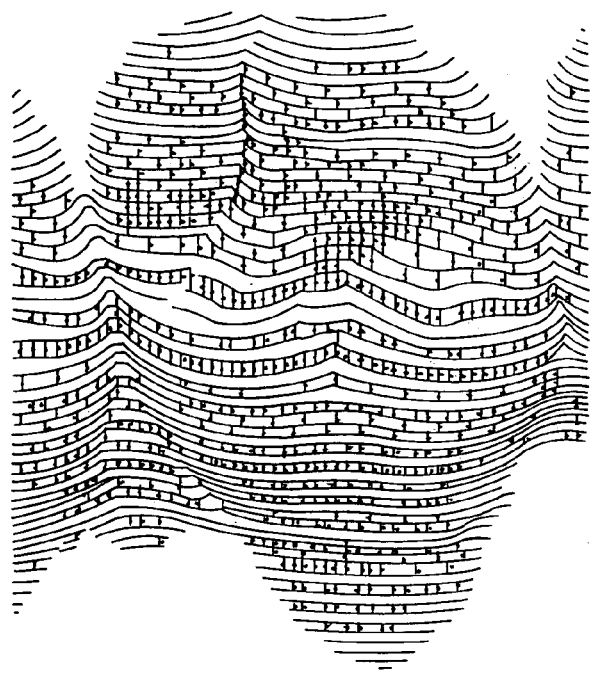
FIG. 27 is an illustration of a two-dimensional bitmap image of a tooth and associated anatomical structures captured by the electronic imaging device of the scanner of FIGS. 1, 2, 3 and 4, prior to any signal processing in the scanning node or workstation.

FIG. 27 is an illustration of a two-dimensional bitmap image of a tooth and associated anatomical structures captured by the electronic imaging device 56 of the scanner of FIGS. 1, 2, 3 and 4, prior to any signal processing in the scanning work station 16. An inspection of FIG. 27 indicates that the image includes various lines and colored dots of the projection pattern, as it is reflected off of the tooth and associated anatomical structures. The location of where these lines and colored dots are imaged on the imaging device 56 contains information as to the three-dimensional shape of the tooth and associated anatomical structure.

Figure 28:
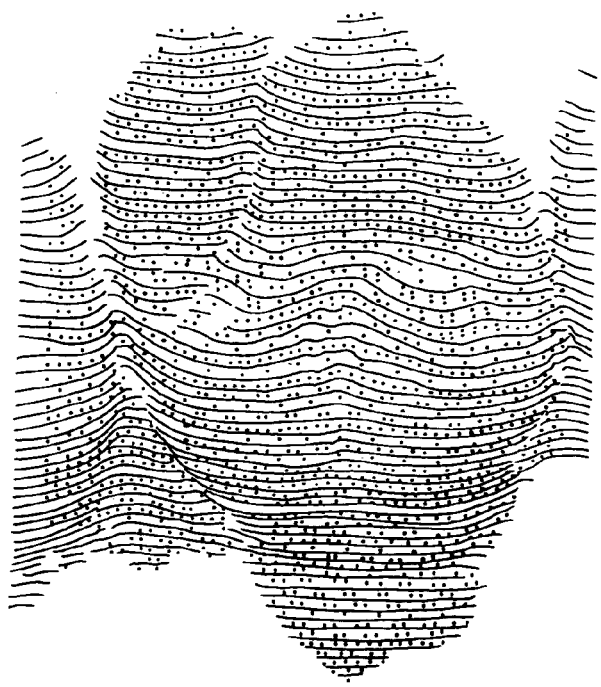
FIG. 28 is an illustration of the image of FIG. 27 after pattern recognition and filtering operations have been performed.

Referring back to FIG. 6, the first step is a pattern recognition process on the captured image. FIG. 28 is an illustration of the image of FIG. 27 after pattern recognition and filtering operations have been performed. The filtering operation basically returns a zero pixel value for those pixels where the pattern recognition process cannot detect the lines and the colored dots, for example due to the surface being out of focus (i.e., out of range of the scanner optics).

After the decoding operation is done on the image of FIG. 28, the result is a set of pixel locations where the decoded rays $R_{n,m}$ of the projection pattern were imaged in the imaging device 56. Step 84 is performed for all such rays, using calibration table #1 of FIG. 26 stored in memory for the scanner. The result, step 86 of FIG. 6, is a set of three dimensional coordinates for all the points in the image, a point cloud comprising a "frame." FIG. 29 is an illustration of a single "frame" of data, that is, a three-dimensional point cloud of a scanned object which has been calculated from a single two dimensional image by the pattern recognition, decoding, and 3-D calculations described herein.

Figure 29:
FIG. 29 is an illustration of a single "frame" of data, that is, a three-dimensional point cloud of a scanned object which has been calculated from a single two dimensional image by the pattern recognition, decoding, and 3-D calculations described herein.
Figure 30:
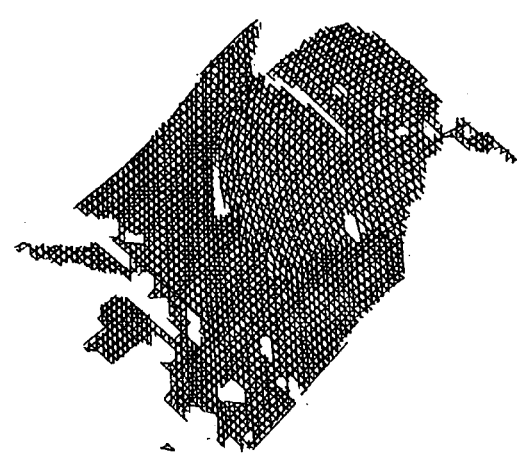
FIG. 30 is an illustration of the points of the cloud of FIG. 29 in which three adjacent points of the cloud are joined together to form triangle surfaces.
Figure 31:
FIG. 31 is a view of the three-dimensional surface formed from the triangle surfaces shown in FIG. 30.
Figure 32:
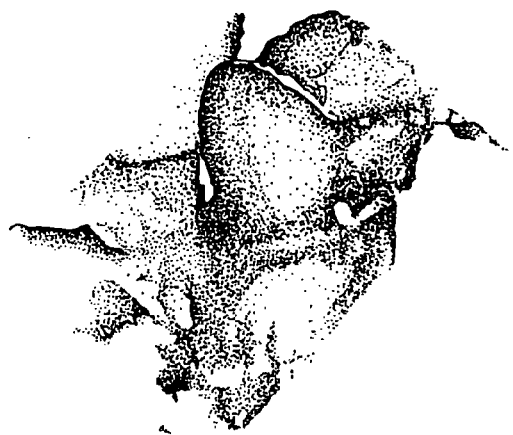
FIG. 32 is a view of the surface of FIG. 31, smoothed by a smoothing algorithm to give a smoother representation of the surface of the object.

FIG. 30 is an illustration of the points of the cloud of FIG. 29, in which three adjacent points of the cloud are joined together to form triangle surfaces. The usage of the triangle surfaces in a registration process is described below. FIG. 31 is another view of the three-dimensional surface formed from the triangle surfaces shown in FIG. 30. FIG. 32 is a view of the surface of FIG. 31, smoothed by a smoothing algorithm to give a smoother representation of the surface of the object. Commercially available off-the-shelf software exists for taking a set of three dimensional coordinates and displaying them on a computer monitor, and such software is used to display the three dimensional surfaces (if desired by the user).

Figure 33:
FIG. 33 is another example of a bitmap image obtained by the electronic imaging device of the scanner.
Figure 34:
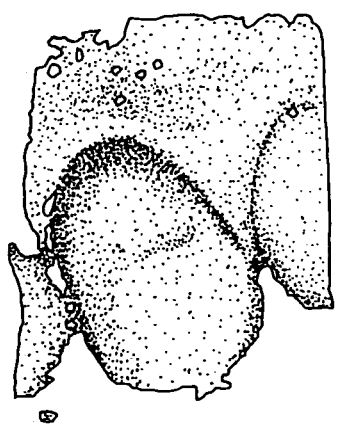
FIG. 34 is a plan view of the three-dimensional surface obtained from the two-dimensional bitmap image of FIG. 33.
Figure 35:
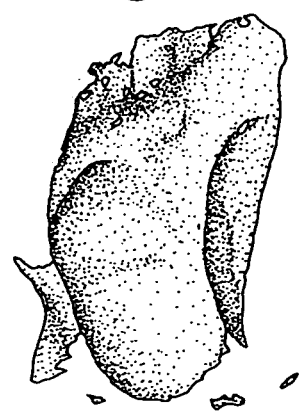
FIG. 35 is a perspective view of the three-dimensional surface shown in FIG. 34.

FIG. 33 is another example of a bitmap image obtained by the electronic imaging device of the scanner. FIG. 34 is a plan view of the three-dimensional surface obtained from the two-dimensional bitmap image of FIG. 33, after the steps of FIG. 6 have been performed. FIG. 35 is a perspective view of the three-dimensional surface shown in FIG. 34. The software programs enable the surface to be rotated in any degree of freedom, allowing for complete inspection and visual analysis of the surface.

Since the scanner and scanned object move relative to each other during capture of the scanned images, the three dimensional coordinates for a large number of frames will not agree with each other. In other words, the X, Y and Z coordinates for a given point on the object will change from frame to frame since the point was imaged from a different spatial orientation for each image. Hence, the frames have to be registered to each other to generate a complete overall digital model of the object. The present invention provides for various registration procedures to be performed on the frames, to find a best-fit solution for coordinates of the object in one frame vis-à-vis coordinates of the object in other frames. These registration procedures are described in the following section.

Figure 36:
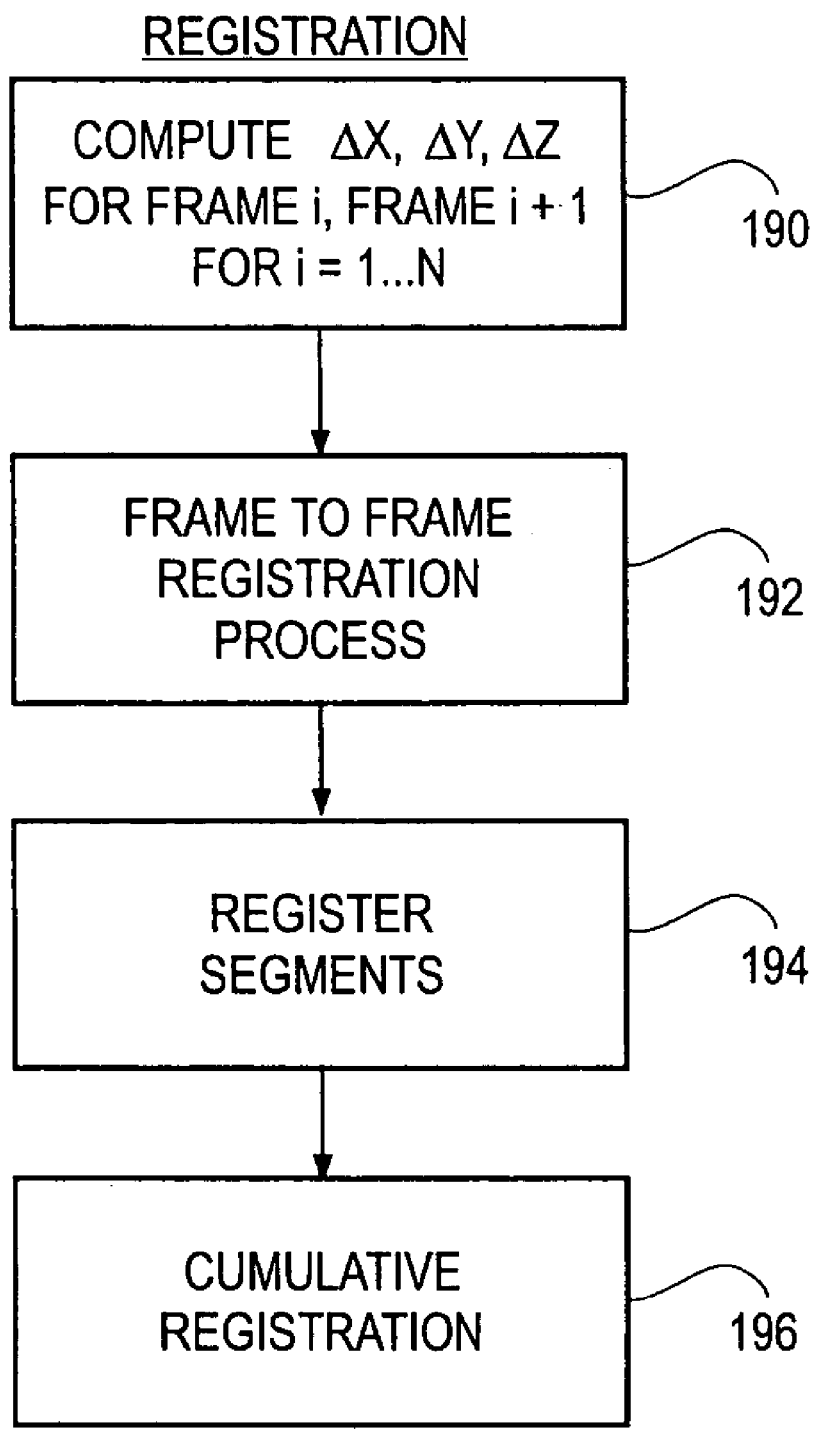
FIG. 36 is a flow chart shown illustrating the steps performed to generate a complete three-dimensional model of the dentition of a patient from a series of scans of the upper and lower jaws.

FIG. 36 is a flow chart illustrating the steps performed to generate a complete three-dimensional model of the dentition of a patient from a series of scans of the upper and lower jaws. The steps include an initial step 190 of determining an entry point into a registration process, a frame to frame registration process 192 of registering one frame to another, a segment registration process 194 to register segments (i.e., portions of a scan where the scan was interrupted for some reason) to one another, and finally a cumulative registration procedure 196 in which the frames are registered to all other frames to obtain a slightly more accurate model of the object than that obtained by frame to frame registration. It will be understood that depending on the application, the step 194 may not be required, a frame to frame registration may only be needed, or the user may only desire a cumulative registration and steps 192 or 194 are not performed at all.

Figure 37A:
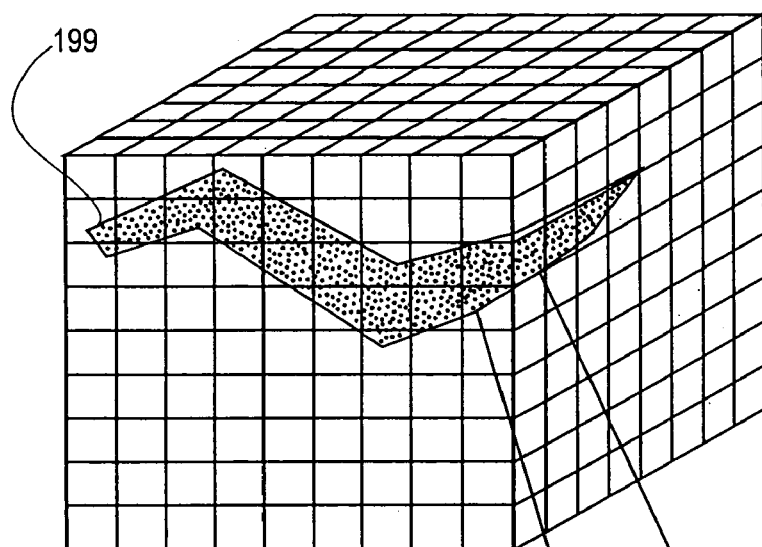
FIG. 37A is an illustration of a mathematical model of a surface of an object after generation of several frames of data and registration of such frames relative to each other to generate a complete model of the surface of the object.
Figure 37B:
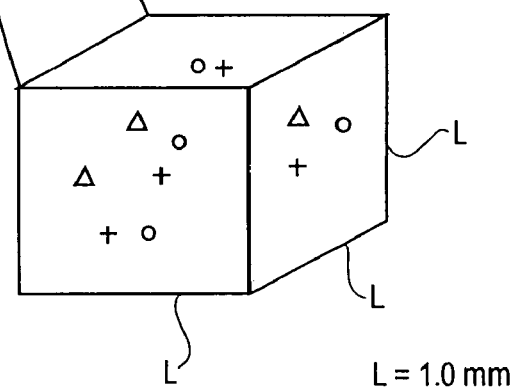
FIG. 37B is a illustration of one small three-dimensional section of the model of FIG. 38A, showing points from three different frames that are located in approximately the same position in three dimensional space after the registration of these frames has been completed.

The result of registration is a three-dimensional model containing all the points from the frames captured by the scanner. An example of such a model is shown in FIG. 37A, where surface 199 indicates the sum total of points of all the frames in three-dimensional space. FIG. 37B illustrates one small section of the surface, showing for example the points in three-dimensional space from three frames.

Figure 37C:
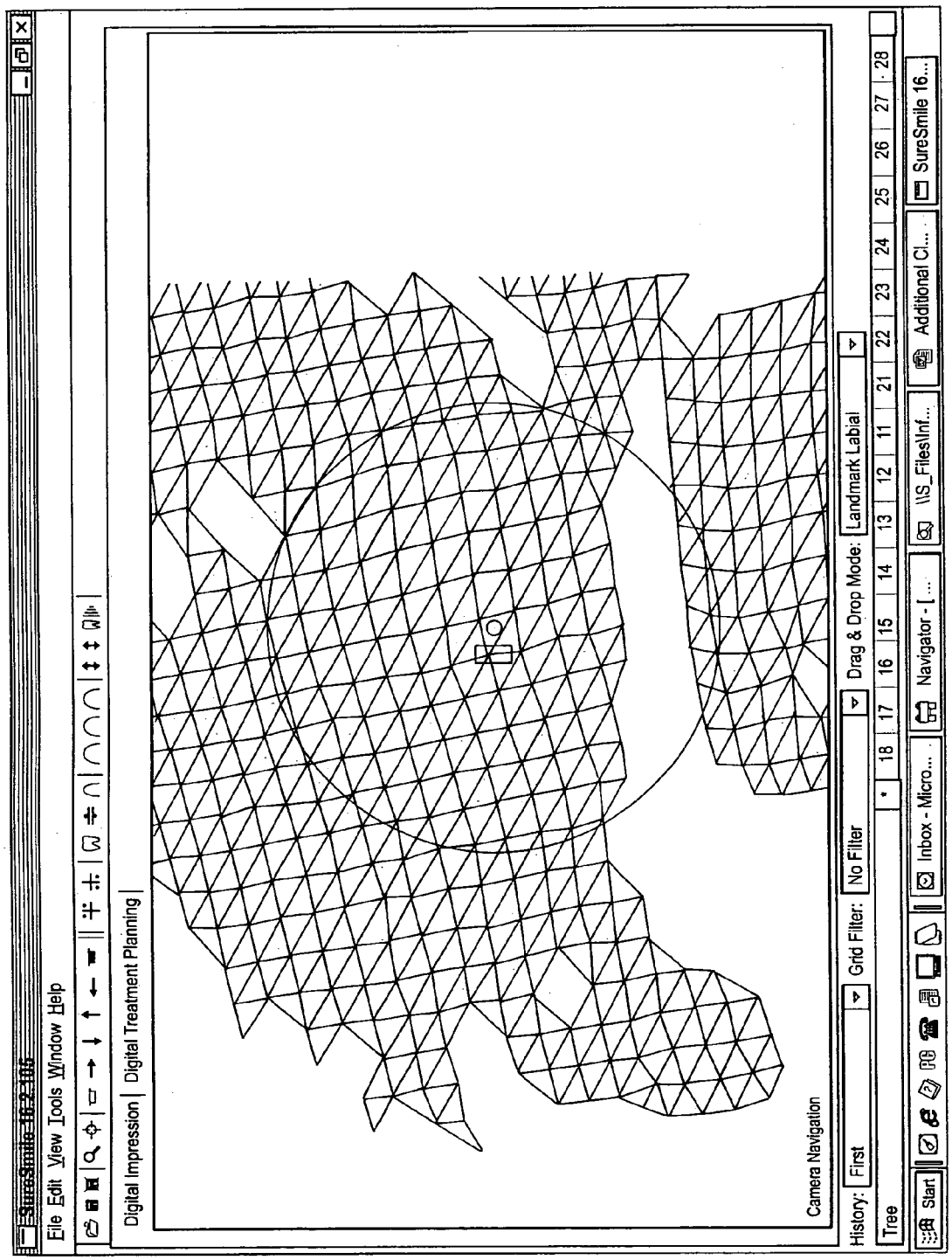
FIG. 37C is a screen shot on the user interface of a back office work station of FIG. 1, showing triangle surfaces for points comprising one frame obtained from scanning a tooth.
Figure 37D:
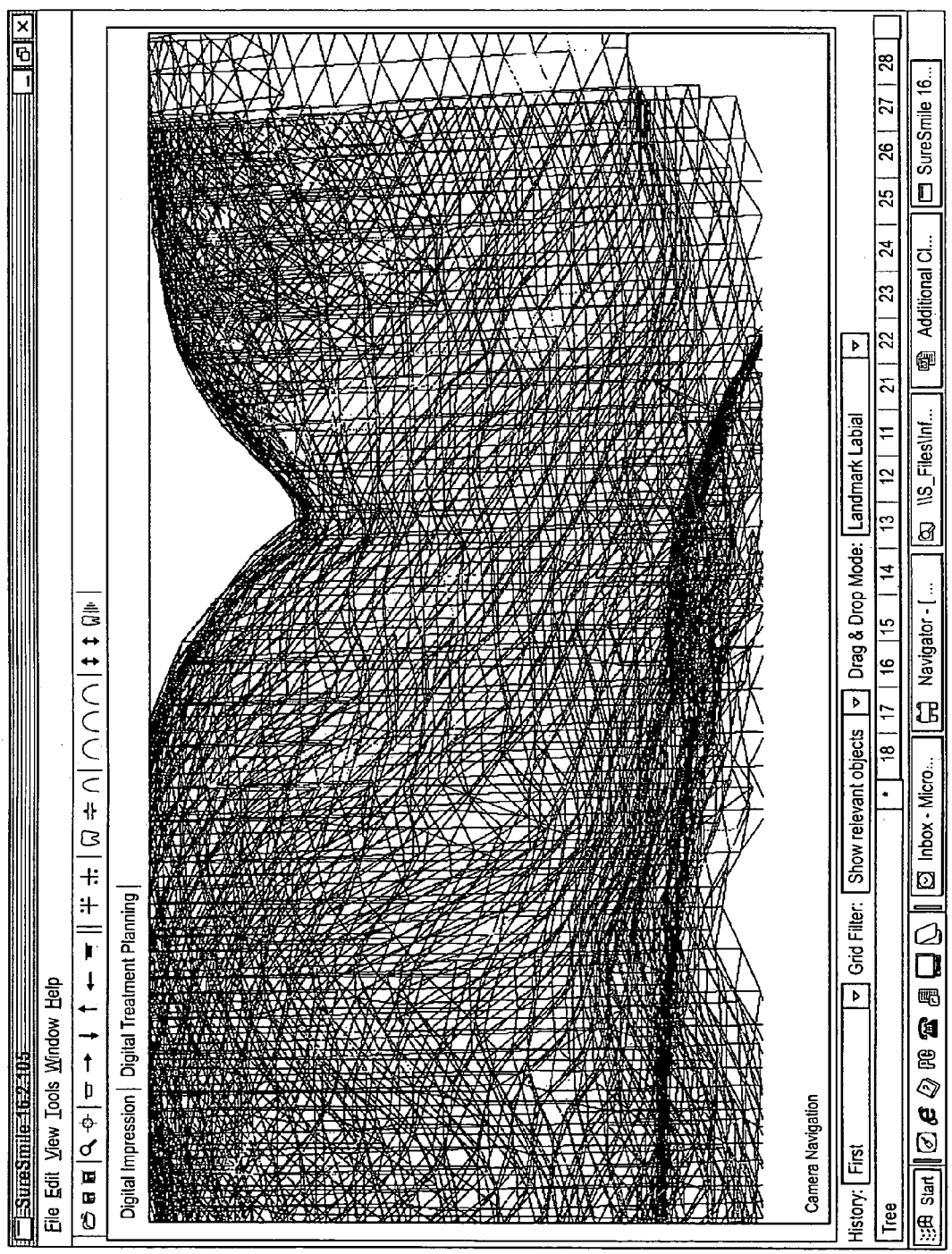
FIG. 37D is a screen shot showing a registration of a large number of overlapping frames on the tooth, of which the frame of FIG. 37C is one frame.

A preferred registration technique involves registering a set of points (three-dimensional coordinates) comprising a frame to a surface formed by a previous frame (or group of frames), rather than registration of one set of points to another set of points. This is due to a relatively coarse projection pattern used in the illustrated embodiment; the points can be low in density as compared to the curvature of the object. FIG. 37C shows one frame from a scan of a tooth, with the points in the frame connected by lines to form a set of triangle surfaces. The coarseness of the projection pattern (and widely spaced points in the point cloud) is compensated by the fact that a given portion of the surface is captured by overlapping frames, and the registration occurs from the points in one frame to the surface in the previous frame or a surface defined by more than one previously registered frames. The registration process described herein ultimately permits a fine resolution in the three-dimensional model. This is indicated by FIG. 37D, showing all the frames for the tooth scan registered to each other to create a very fine and high resolution virtual model of the tooth.

A. Entry Point into Registration (step 190, FIG. 36)

Registration processes require a starting point for fitting one frame, frame i to another frame, frame i+1. The starting point, in the illustrated embodiment, is rough calculation of the offset between overlapping points in the frames in X, Y and Z directions. Whereas prior art systems have good pre-knowledge of the spatial relationship due to the known physical arrangement of the scanner and the object, the present system does not. The starting point is the initial assumption of spatial relationship between one frame and the previous frame (and one frame and a set of previous frames).

Figure 38A:
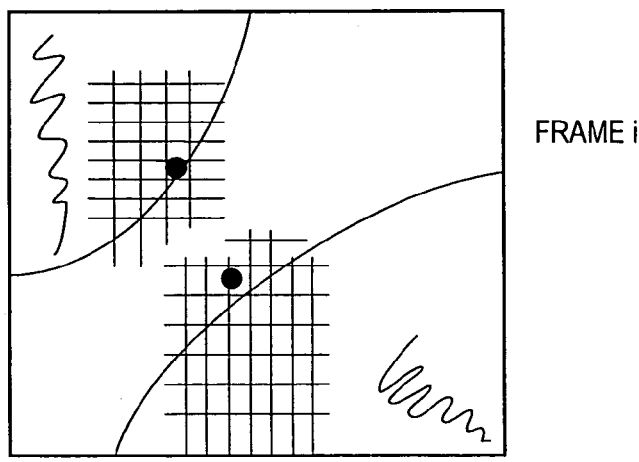
FIGS. 38A–38C are an illustration of a two-dimensional cross-correlation procedure in the X and Y directions. The procedure, along with the procedure in FIGS. 37A and 37B, is used to find an initial entry point into a registration algorithm between successive frames of data.
Figure 38B:
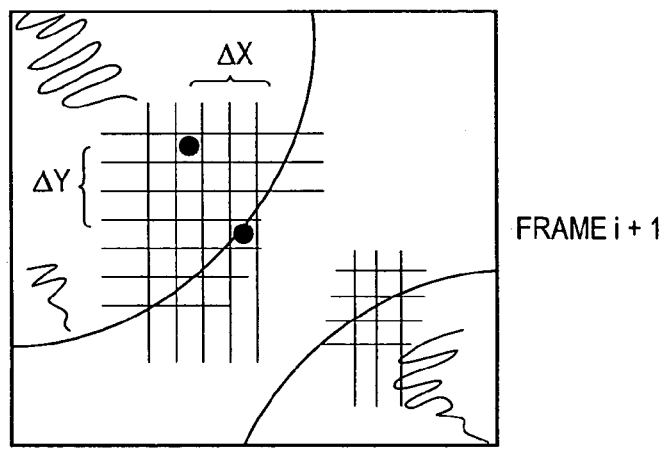
Figure 38C:
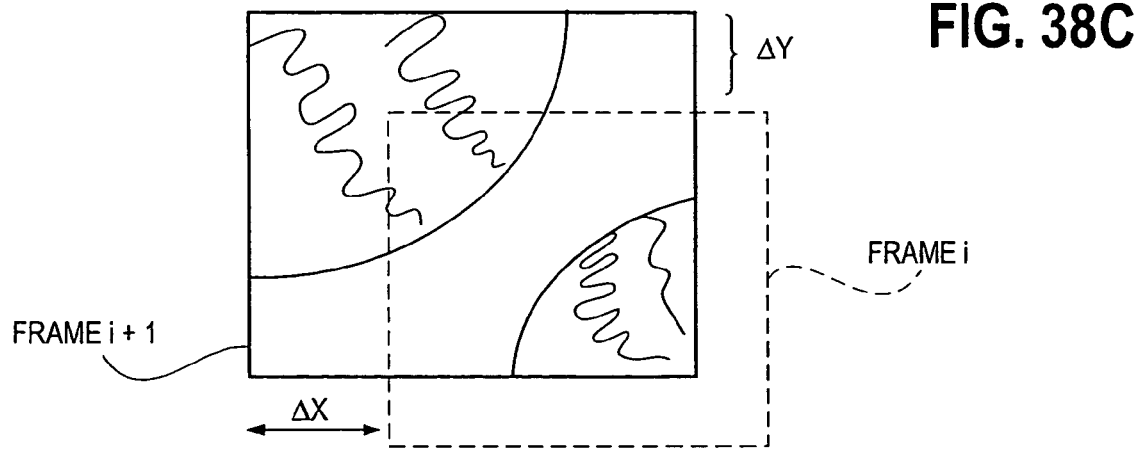
Figure 39A:
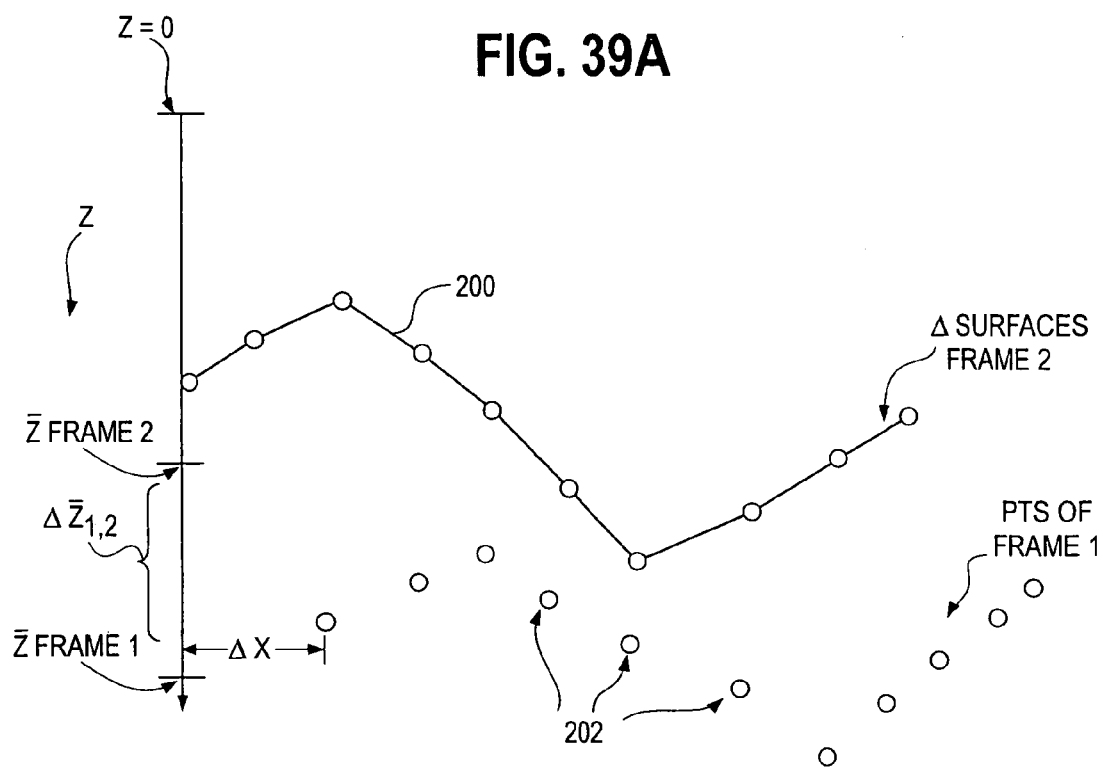
FIGS. 39A and 39B are an illustration of a one-dimensional correlation procedure in the Z direction for two successive frames.
Figure 39B:
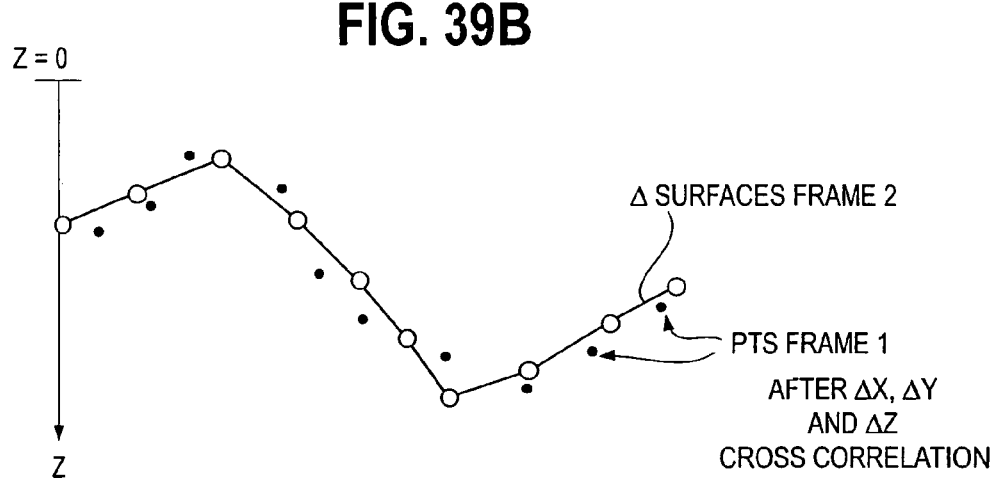

The method of calculation of the offset in X and Y directions is illustrated in FIG. 38A–C. FIGS. 38A–38C are an illustration of a two-dimensional cross-correlation procedure in the X and Y directions. The procedure, along with the procedure in FIGS. 39A and 39B, is used to find an initial entry point into a registration algorithm between successive frames of data.

It can be seen from FIGS. 38A and 38B that frame i+1 is moved in the X and Y directions from frame i. To obtain the amount of movement, $\Delta X$ and $\Delta Y$, the images are projected to both X and Y axes by adding all pixel values of every row, acquiring a one dimensional Y-vector, and adding all the pixel values of every column, acquiring a one-dimensional X-vector. This is performed for both frames, resulting in $X_{Frame\ i}$ and $X_{frame\ i+1}$ and $Y_{frame\ i}$ and $Y_{frame\ i+1}$. The vectors are smoothed to suppress the influence of the projected pattern.

To compute $\Delta X$, the absolute value of the difference between each value of the X-vector of frame i (frame $i$-$X_{fame\ i}$) and the X vector of frame i+1 (frame i+1-$X_{frame+1}$) is calculated with a varying position shift within a range of $-xa<k<+xe$. The sum of these values represents the resemblance of $X_{frame\ i}$ and $X_{frame\ i+1}$ shifted by a certain amount k. The minimum value of k is determined. This result gives the shift or movement in the $\Delta X$ direction.

The same process is also performed the Y direction. As can be seen in FIG. 38C, if frame i is moved by an amount $\Delta X$ and $\Delta Y$, the overlapping points in both frames will have the same values and the sum of the difference in pixel value will be approximately zero.

FIGS. 39A and 39B are an illustration of a one-dimensional correlation procedure in the Z direction for two successive frames, in the present example frame 1 and frame 2. Line 200 represents a three-dimensional surface of the second frame, formed by connecting three adjacent points in the point cloud. The set of points 202 represents the points of the point cloud representing frame 1. To compute the Z offset, $\Delta Z$, the sum is taken of all the Z values of Frame 2, and the result divided by the number of points, resulting in an average Z value of Frame 2. The same is done for Frame 1. The difference between the average Z value of Frame 2 and the average Z value of Frame 1 is the Z offset, $\Delta Z$. FIG. 37B illustrates the result after translation of Frame 1 by the amount $\Delta X$, $\Delta Y$ and $\Delta Z$. The result is that the points of frame 1 are quite close to the triangle surfaces of Frame 2. The values of $\Delta X$, $\Delta Y$ and $\Delta Z$ are stored for Frame 1 and used as an entry point to a registration procedure.

B. Frame to Frame Registration

Frame to frame registration is a process for registering one frame with another frame, that is, finding a best-fit in terms of translation and rotation make overlapping points in the frames agree with each other. If the frames are generated in sequential order, frame to frame registration refers to registration of the second frame to the first frame, the third frame to the second frame, from the fourth frame to the third frame, etc. Frame to frame registration can be performed very quickly. It can be performed in a manner such that the operator of the scanning system sees the results of frame to frame registration on the monitor of the scanning work station while they are still scanning the patient. What they see is an accurate three-dimensional representation of the dentition on the monitor, for those portions of the dentition that have been scanned thus far. As additional frames are obtained, they are registered to the previous frame and added to the computer model. When scanning is complete, the computer model can be rotated around on the monitor and inspected to see that all relevant portions of the teeth and anatomical structures have been scanned. The user thus gets immediate feedback on the results of the scanning using frame to frame registration.

FIGS. 40A–40D is a flow chart of a frame to frame registration process for a set of frames, each frame consisting of a three-dimensional point cloud of a scanned object. Each frame is typically generated from a different spatial orientation of the scanner relative to the object due to movement of the scanner during image capture, hence the frames overlap to at least some extent. The registration process is used to find a best fit between the frames relative to each other, and thereby provide a complete three-dimensional virtual model of the surface of the object from all of the frames. The end result of the frame to frame registration is a substantially exact three dimensional model of the scanned object. This object is represented by a large set of point coordinates in computer memory. The result is also represented as a set of transformation matrices providing information as to how each frame of points should be translated and rotated in three dimensions in order to fit to the previous frame.

The frame to frame registration process is also an iterative process. At the end of each iteration, a comparison is made as to how "close" the two frames are to each other in three dimensions. If they are not close enough (with "closeness" determined in absolute terms by a quality index, say in microns), another iteration is done, using the results of the first iteration. The frame to frame process may continue for tens or even hundreds of iterations, depending on how fine or precise the user wants the registration to be. The process stops when a best fit between two frames has been reached or a maximum number of iterations has occurred.

Referring now to FIG. 40A–40D in conjunction with FIGS. 39 and 41–43, an initial step 209 is performed as an entry point into the registration procedure. In this step, the processes of FIG. 39A and described previously is performed to make a Z-coordinate transformation of frame i−1 and frame i. Basically, this transformation is performed by summing the Z coordinate values of both frames individually, finding a median Z value for each frame, finding the difference or ΔZ value from these median values, and shifting one frame (frame i) by this amount to bring the Z coordinates of all the points in that frame closer to the points of frame i−1. The rationale of step 209 is as follows. The Z axis measurements of a surface represent a degree of freedom of the scanner movement. Scanner movements in the Z direction do not provide significant new information on the object being scanned. However, because of the focus optics of the electronic imaging device (108 in FIG. 7), the visible surface of the object becomes slightly smaller or larger depending on how much the scanner is moved in the Z direction relative to the surface, while the center of the surface (or, loosely speaking, the "center of gravity") of the visible area basically remains nearly the same with Z direction movement. The Z coordinate transformation step 209 eliminates this effect by normalizing the Z surface coordinates. This process also makes possible the exclusion criteria of step 2 described below, by which non-overlapping points and stray data points are excluded from the registration process.

Figure 40A:
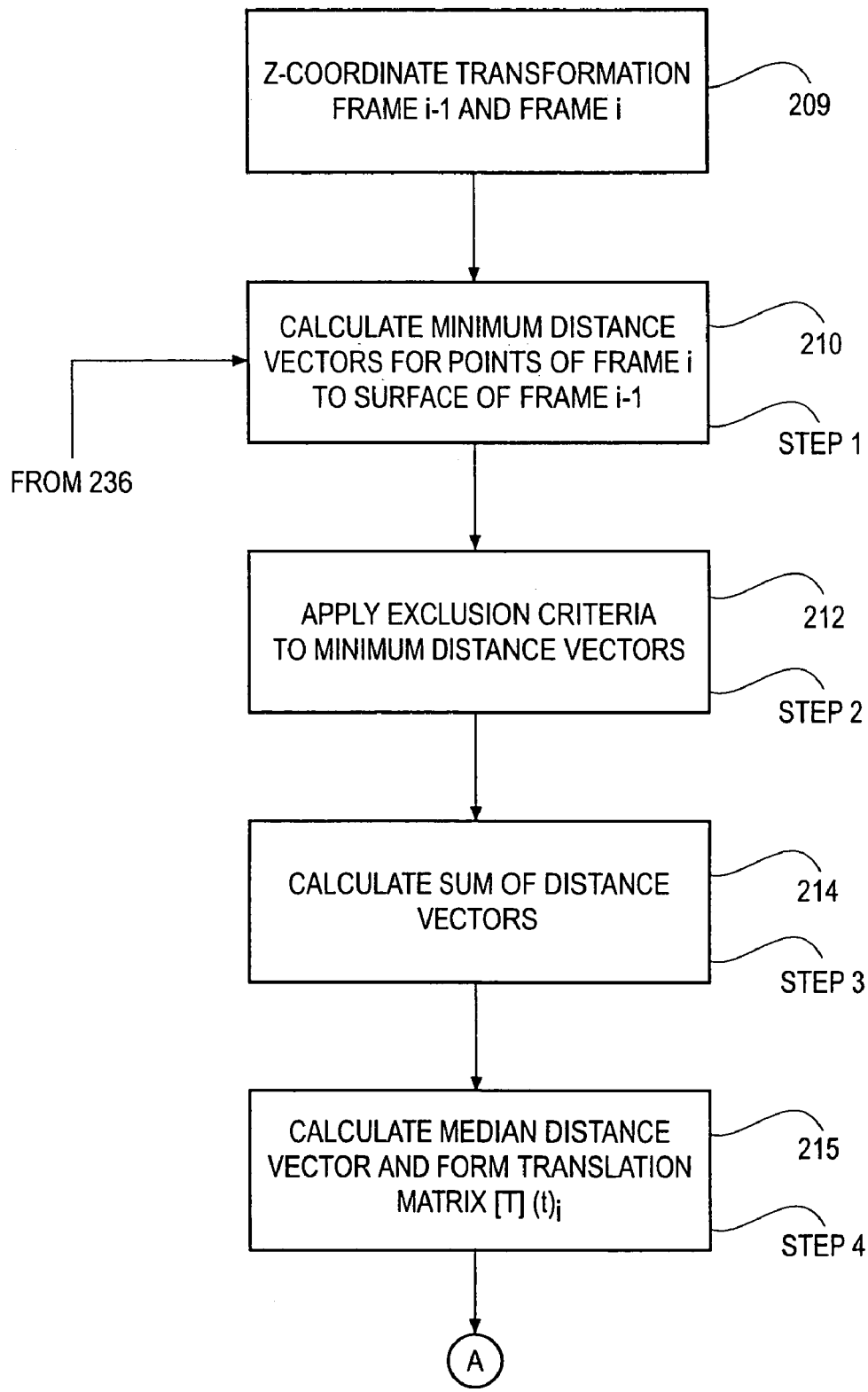
FIGS. 40A–40D are an illustration of a frame to frame registration process for a set of frames, each frame consisting of a three-dimensional point cloud of a scanned object. Each frame is typically generated from a different spatial orientation of the scanner relative to the object due to movement of the scanner during image capture, hence the frames overlap to at least some extent. The registration process is used to find a best fit between the frames relative to each other, and thereby provide a complete three-dimensional virtual model of the surface of the object from all of the frames.
Figure 41:
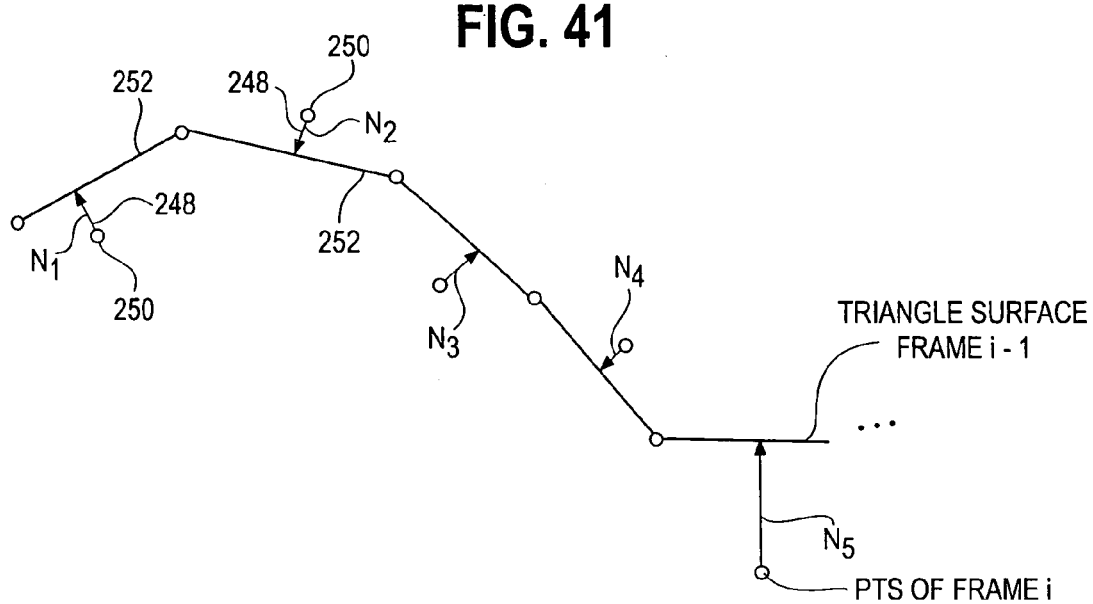
FIG. 41 illustrates the normal vectors used in the process of FIG. 40.

The registration procedure itself starts with step 1, 209 in FIG. 40A. At this step, minimum distance vectors 248 (N1, N2, . . . ) are calculated from every point in Frame i to the surface of frame i−1. The surface of a frame can be obtained easily by connecting neighborhood points to together with a triangle or other polygon. The minimum distance vector, for each point in Frame i, is defined as the distance vector having a magnitude which is the minimum of the following three vectors: 1) the shortest vector from the point intersecting a triangle surface in frame i−1 normal to the triangle surface; 2) the shortest vector from the point orthogonal to the edge of a triangle surface in frame i−1, and 3) the shortest vector from the point to the nearest point in frame i−1. Most often, but not always, this will be a normal vector, type 1) above. In the example of FIG. 41, minimum distance vectors 248 are computed from the points 250 in frame i to the triangle surfaces 252 of frame i−1, with the vectors 248 normal to the surfaces 252.

At step 2 (212 in FIG. 40A), three exclusion criteria are applied to the minimum distance vectors of step 1, in order to eliminate non-overlapping data points between the two frames and to eliminate stray data points. First, all minimum distance vectors that relate to a boundary element (edge or point) in frame 1 are excluded. Second, all remaining minimum distance vectors with an amount exceeding a certain predefined value R, likely indicating stray data points, are excluded. Thirdly, only triangle surfaces are taken into consideration which form the outside surface with respect to the scanner viewing direction. Every surface has by definition two sides. We regard the "outside" surface as the surface of the object that is oriented towards the scanner.

Figure 42:
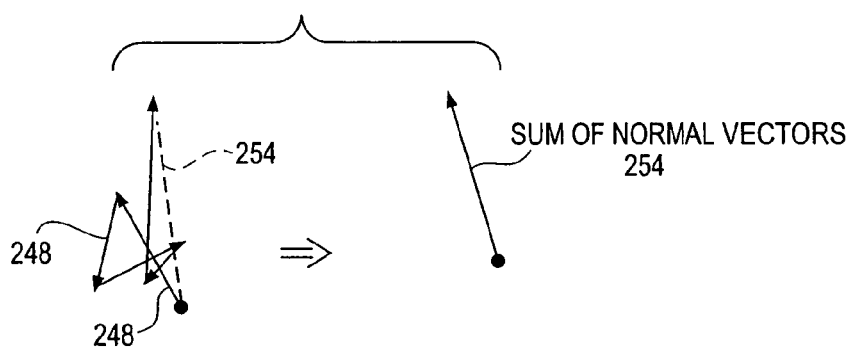
FIG. 42 illustrates the summation of the normal vectors from frame 1 to reach a net normal vector $N_{net}$.

At step 3 (214) the vector sum of all the minimum distance vectors $N_1 \ldots N_N$ is computed. This is shown in FIG. 42, with vector 254 representing the vector sum.

At step 4 (215), the median minimal distance vector (t) is computed by multiplying the vector sum 254 by the scalar 1/N. The median minimal distance vector basically constitutes a measure of how frame i should be translated in X Y and Z directions in order to better fit to frame i−1. Now, the registration process needs to compute a rotation factor, which is explained by steps 5–8, to indicate how frame i needs to be rotated in order to better fit frame i−1.

At step 5 (216), the X, Y and Z components of the median minimal distance vector is subtracted from every point in frame i. This is performed by making a copy of the frame i coordinates and operating on the copy as an interim step in the procedure, the underlying data from frame i is unchanged. At the same step the "center of mass" of the points of frame i which are not excluded by step 2 is calculated. The "center of mass" is defined as the vector sum of position vectors of all mentions points scaled by the inverse of the number of points.

Figure 43:
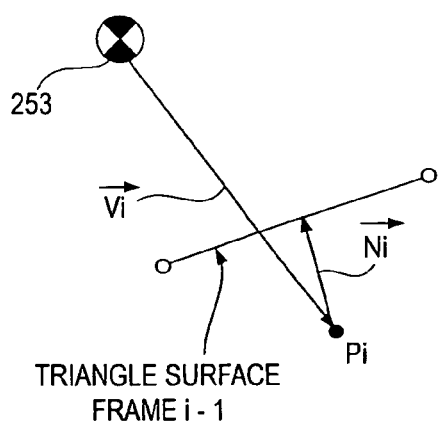
FIG. 43 illustrates the vectors Vi and Ni from the process of FIG. 40.
Figure 44:
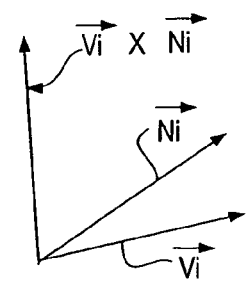
FIG. 44 illustrates the cross product of vectors Vi and Ni.

At step 6 (218) a calculation is made of the cross product of two vectors for every point in frame i. With reference to FIG. 43, the two vectors are as follows: 1) a position vector Vi extending from the origin 253 of the global coordinate system to the points in frame i, subtracted by the vector of the center of mass of the remaining points of frame i as calculated in step 5, and 2) the identified minimum distance vector Ni for that point.

At step 7 (220), a calculation is made of the vector sum of the cross vectors calculated in step 6, that is the net cross vector $$\sum_j (v_j \times n_j)$$

for all i points in the frame i, where x is the cross product operator.

At step 8 (222), the vector sum of step 7 is weighted against the inverse of the sum of all squares of the position vectors (Vi) of the points in frame i, to arrive at a rotation vector U. U is interpreted as follows: The direction of U gives us the rotation axis and the magnitude of U is the angle or amount of rotation. In particular, if we consider Vi to be the position vectors from the origin of the coordinate system to the vertex of every point, and Ni being the minimal distance vectors defined above, then the weighting is as follows:

$$U = \frac{\sum_j (v_j \times n_j)}{\sum_j v_j^2}$$

The reasoning behind this weighting is as follows. If you imagine the distance vectors as the realization of linear spring elements, the vector sum of the cross products represents the aggregate moment, or rotational discrepancy, generated between both frames. In the case of small deviations between the position of frame i and its final position, it can be assumed that the rotational moment also determined the direction of the necessary adjustment. The scaling with the help of the inverse of the sum of the squares of the position vectors considers the global extension of frame i. That is, the larger the distances of the points from the center, the larger is the ratio of rotational moment and angle between the present position and the target position. In a global sense, the mentioned factor (inverse of the sum of squares of position vectors) describes this ratio.

The derivation of the proper scaling factor is by no means an exact calculation. It has, however, turned out that using this factor in all empirical cases, the iteration of defining overlapping areas and execution of transformations converges.

At step 9, the result of step 8 is scaled with an empirical "acceleration factor" f. The factor f serves to possibly accelerate this convergence. A value of f of greater than 1 is appropriate for relatively large rotational displacements, but in any event has to be determined empirically.

At step 10 (226), the result of step 9 is interpreted as an axis of rotation, the magnitude of which indicates the amount by which frame i has to be rotated in order to make the local overlapping areas of both frames lie within each other. The magnitude of the rotation vector is interpreted as the angle around which frame i has to be rotated.

A rotation transformation matrix [T] (R) is calculated for frame i. This formula shows how to convert the rotation vector resulting from step 9, where β is the original length of the net cross vector which equals the angle of rotation that is required to fit the overlapping areas of frame i to frame i−1 and u is the unit vector of $U_r$, $$u = \frac{U}{|U|}$$

with components $u_x$, $u_y$, $u_z$.

$$[T](R) = \begin{pmatrix} (1-\cos\beta)u_x^2 + \cos\beta & (1-\cos\beta)u_x u_y - u_z \sin\beta & (1-\cos\beta)u_x u_z + u_y \sin\beta \\ (1-\cos\beta)u_y u_x + u_z \sin\beta & (1-\cos\beta)u_y^2 + \cos\beta & (1-\cos\beta)u_y u_z - u_x \sin\beta \\ (1-\cos\beta)u_z u_x - u_y \sin\beta & (1-\cos\beta)u_z u_y + u_x \sin\beta & (1-\cos\beta)u_z^2 + \cos\beta \end{pmatrix}$$

To obtain a unique transformation operator for calculating the translation and the rotation transformation in a closed manner a 4×4 matrix representation is used. The relation between the 4×4 representation and the three dimensional rotation represented by 3×3 Matrix [T](R) is as follows $$[T_4](R) = \begin{pmatrix} [T](R) & 0 \\ 0 & 1 \end{pmatrix}$$

and between the 4×4 representation and the three dimensional translation, represented by vector (t)

$$[T_4](t) = \begin{pmatrix} 1 & 0 & 0 & t_x \\ 0 & 1 & 0 & t_y \\ 0 & 0 & 1 & t_z \\ 0 & 0 & 0 & 1 \end{pmatrix}$$

To apply this 4×4 matrices on the three dimensional vectors the following convention is made: A three dimensional vector is transformed into the 4 dimensional vector space by identifying the first three components of the 4 vector with the components of the three dimensional vector but the fourth component is always unique. $(x,y,z)^T \rightarrow (x, y, z, 1)^T$ At step 11 (228 in FIG. 40C), a transformation matrix for frame i, [T4](i), is calculated by multiplying the rotation matrix [T4] (R) (from right) by the translation matrix [T4](t) from step 4 $[T_4](i)=[T_4](R) [T_4](t)$.

Alternatively, the point cloud of frame i can be separately and independently operated on by the rotation matrix and the translation vector.

At step 12 (230), a calculation is made of the square root of the sum of the squares of the minimum distance vectors calculated in step 1 (210) of FIG. 40A, which indicates the closeness factor quality of the registration in this iteration, value MA below. At step 12 (232) the closeness factor MA is compared to a quality index or threshold indicative of a successful registration (e.g., 50 microns). If the value MA is greater than the quality index, the registration process is repeated another iteration. All of the points in the ith frame are updated by operation of the transformation matrix [T4] i, as indicated at step 234. The process goes back to step 1 as indicated at 236, and another iteration is performed of steps 1–13.

Figure 40B:
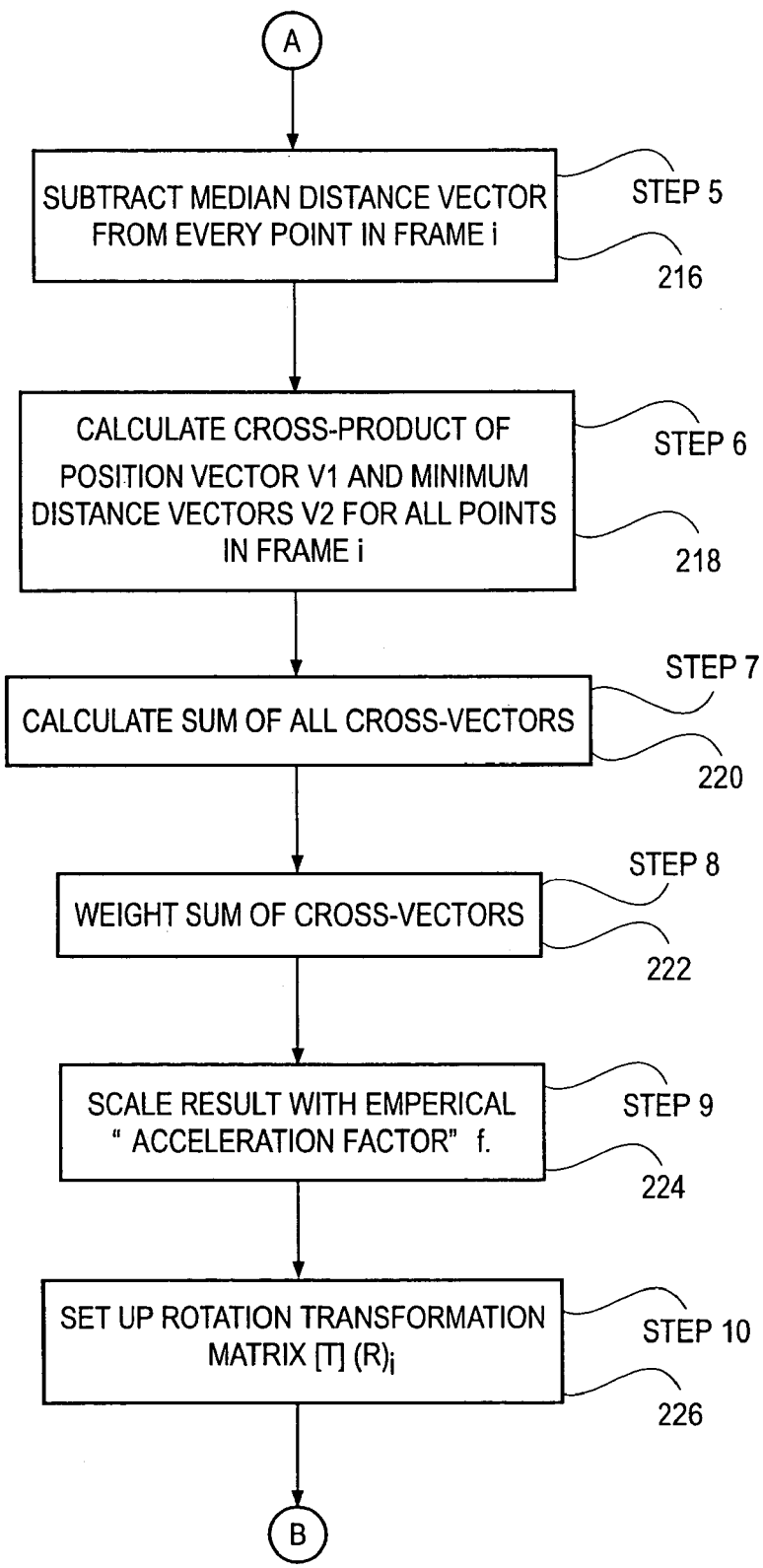
Figure 40C:
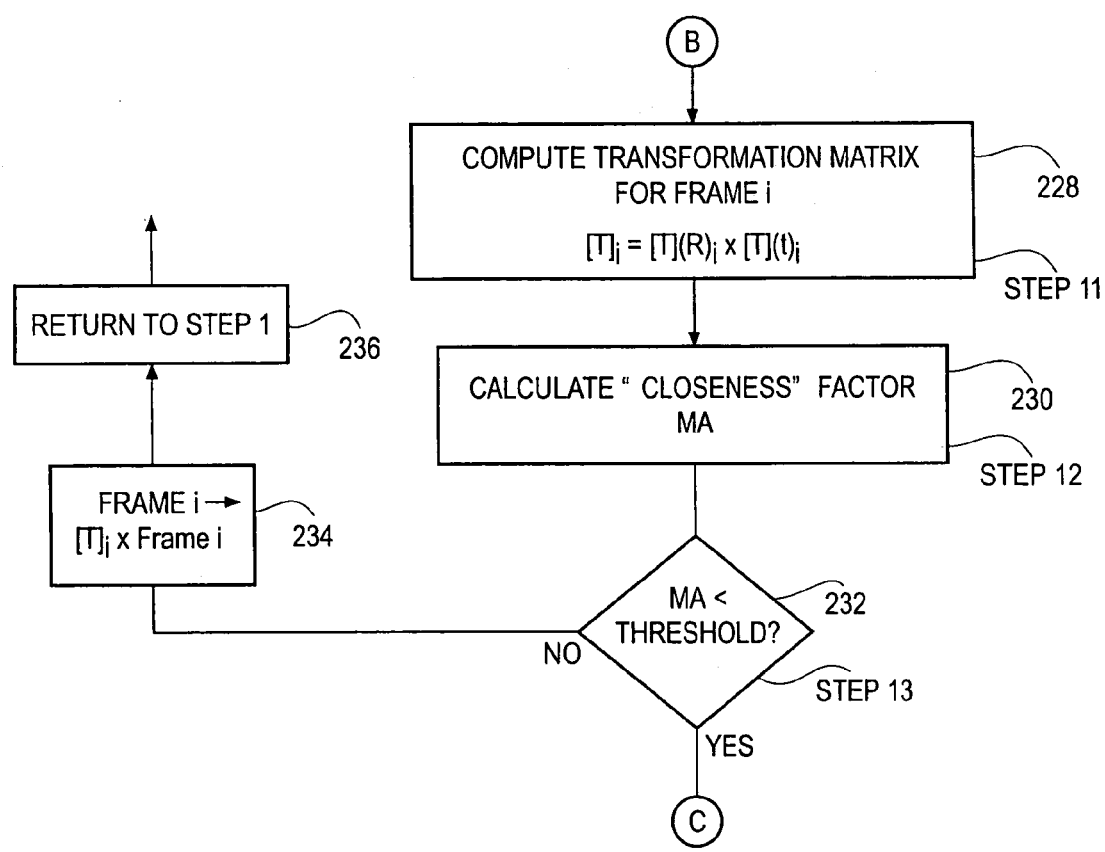
Figure 40D:
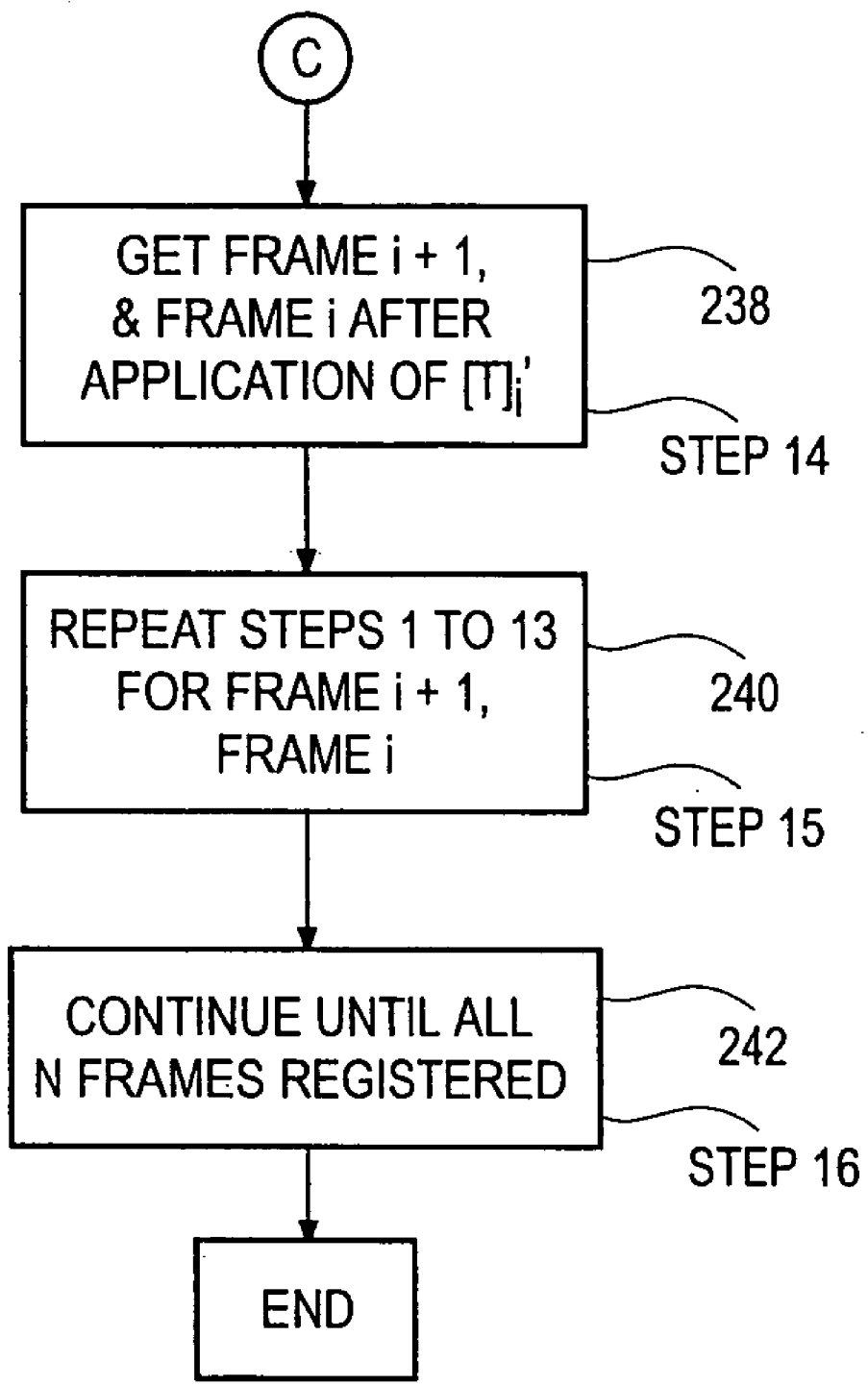

If the closeness factor MA is less than the quality index, the registration process proceeds for the next frame. As shown in FIG. 40D, at step 14 the process retrieves the next frame (frame i+1) and frame i after application of the transformation matrix [T4] i. At step 15 (240), the iterative process of steps 1–14 is repeated for frame i and frame i+1. This process continues until all the N frames have been registered, as indicated at step 16 (242). At the end of the process, the result is a set of points comprising the three-dimensional model, and a set of transformation matrices $[T4]_2$ to $[T4]_N$ for each of the frames (other than the first frame, frame 1), which are used to generate the three dimensional model. One frame, such as frame 1, the first one generated, is chosen as the starting frame for the registration and there is no transformation matrix for that frame.

Figure 45:
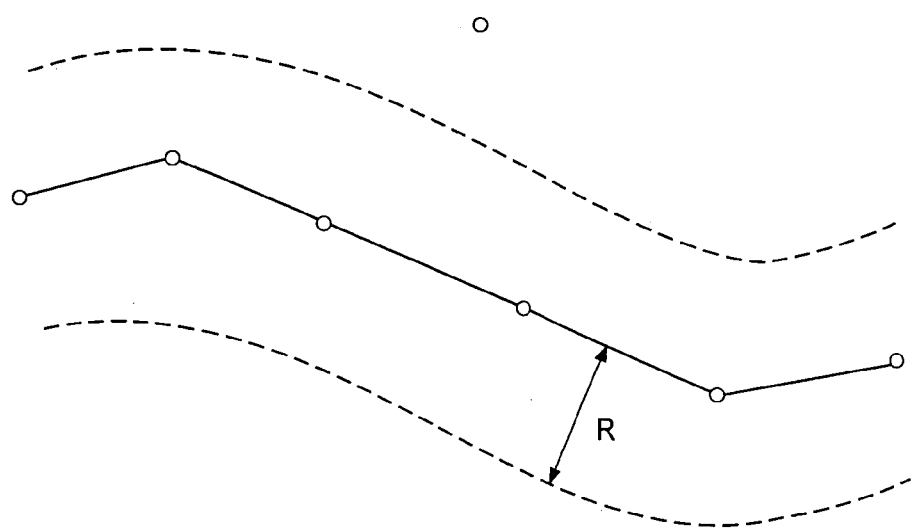
FIG. 45 illustrates the parameter R, which is used in the frame registration process to discard or filter out points which are greater than a distance R from the triangle surfaces.

FIG. 45 illustrates that a range variable R can be used to filter or limit the number of points in a frame that are used when calculating net normal vectors, triangle surface, cross vectors, etc. The purpose of the range variable R is to screen out stray data points far from the triangle surface of the previous frame. The stray data has the effect of skewing the entries of the transformation matrix and increasing the number of iterations until the quality index is met. R can be for example 1 mm, or much less such as 1/50 mm.

Figure 46:
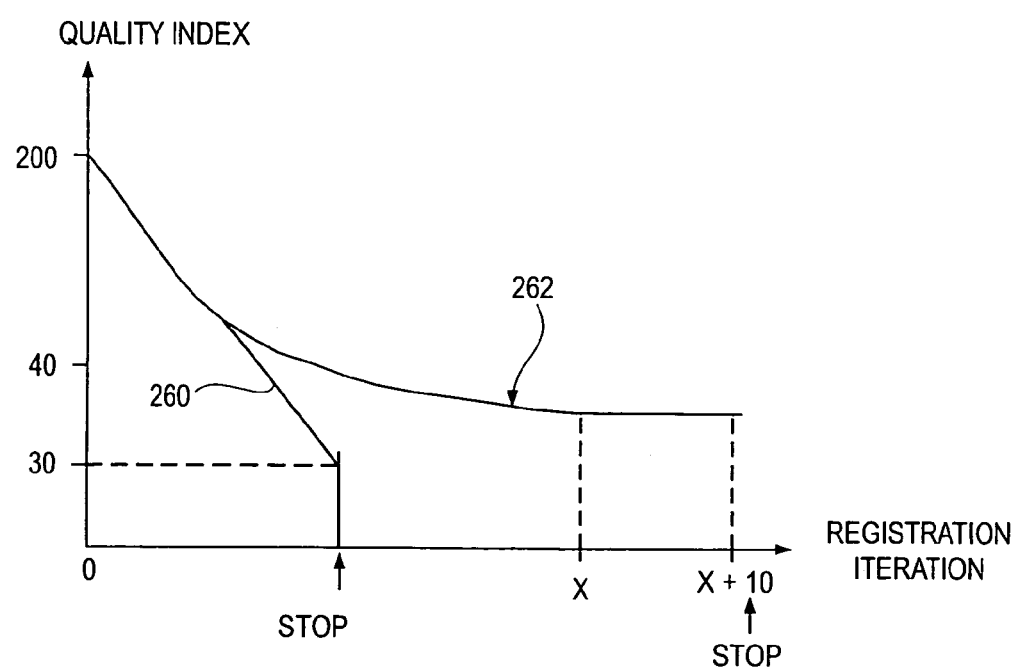
FIG. 46 is an illustration of the closeness factor or quality index, measured as the magnitude of the net normal vector $N_{net}$, as a function of iterations of the process of FIG. 40, showing how the quality index improves with successive iterations of the registration process.

FIG. 46 illustrates two ways in which the frame to frame registration process may terminate. As shown by line 260, the process may terminate when the closeness factor goes below the threshold, here 30 microns. Alternatively, the closeness factor may level off at some value above the quality index, despite further iterations of steps 1–13 of FIG. 40. This is indicated by line 262. When the closeness factor MA does not improve by at least some amount per iteration (say 1 percent) after 10 iterations, the process is deemed complete. Here, the designation x indicates the iteration in which the amount of improvement in the quality index from the previous iteration to that iteration was first less than a threshold, e.g., 1 percent.

C. Cumulative Registration of Entire Jaw

As noted above, cumulative registration is an alternative or improvement to a frame to frame registration. The difference between the two is that frame to frame registration only registers one frame to one other frame, whereas cumulative registration is a registration of a frame to more than one other frame, such as where one frame is registered to all previously registered frames. There are numerous types of cumulative registrations that can be performed, and a few examples will be given here. An advantage of cumulative registration is more accuracy in the resulting three-dimensional model. The disadvantage is that cumulative registration can be significantly more computationally intensive, and therefore require more time to be performed using currently available low cost microprocessors or computers.

Figure 47A:
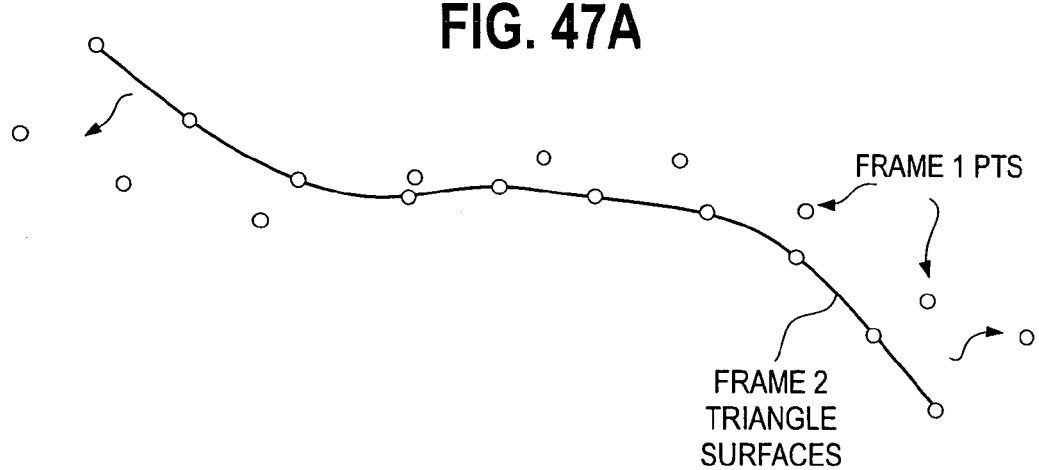
FIGS. 47A and 47B are an illustration of a cumulative registration procedure, which is an alternative to the frame to frame registration procedure of FIG. 40.
Figure 47B:
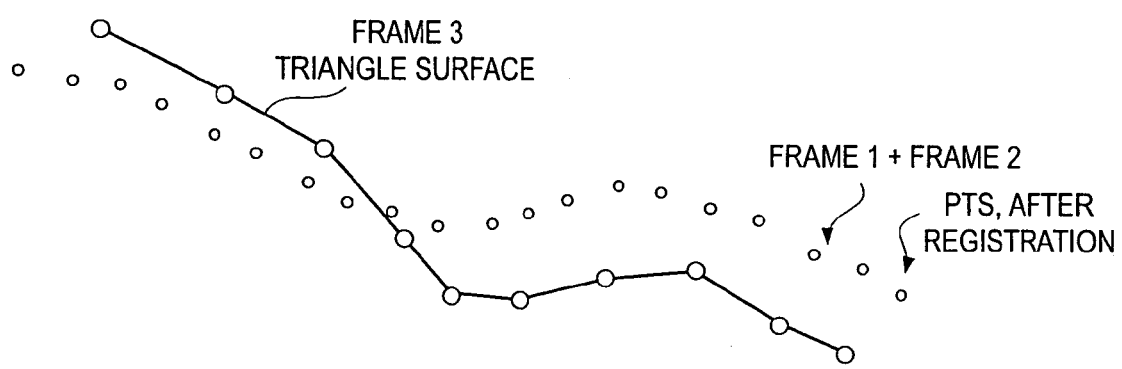

FIGS. 47A and 47B are a simplified illustration of one possible cumulative registration procedure. FIG. 47A shows triangle surfaces of frame 2 and points of frame 1. The points and surfaces represented in FIG. 47A actually are in three dimensions. After registration of frame 2 to frame 1, we are ready for frame 3. Unlike frame to frame registration, frame 3 is registered to both frame 1 and frame 2. In other words, triangle surfaces are formed on the points of frame 3 and minimal distance vectors are calculated for each of the points in frame 1 and frame 2 (after registration to frame 1), and the other steps of FIG. 40 are performed. As each new frame is retrieved, it is registered to the total sum of points from all the previous frames, after the previous registration.

Figure 48B:
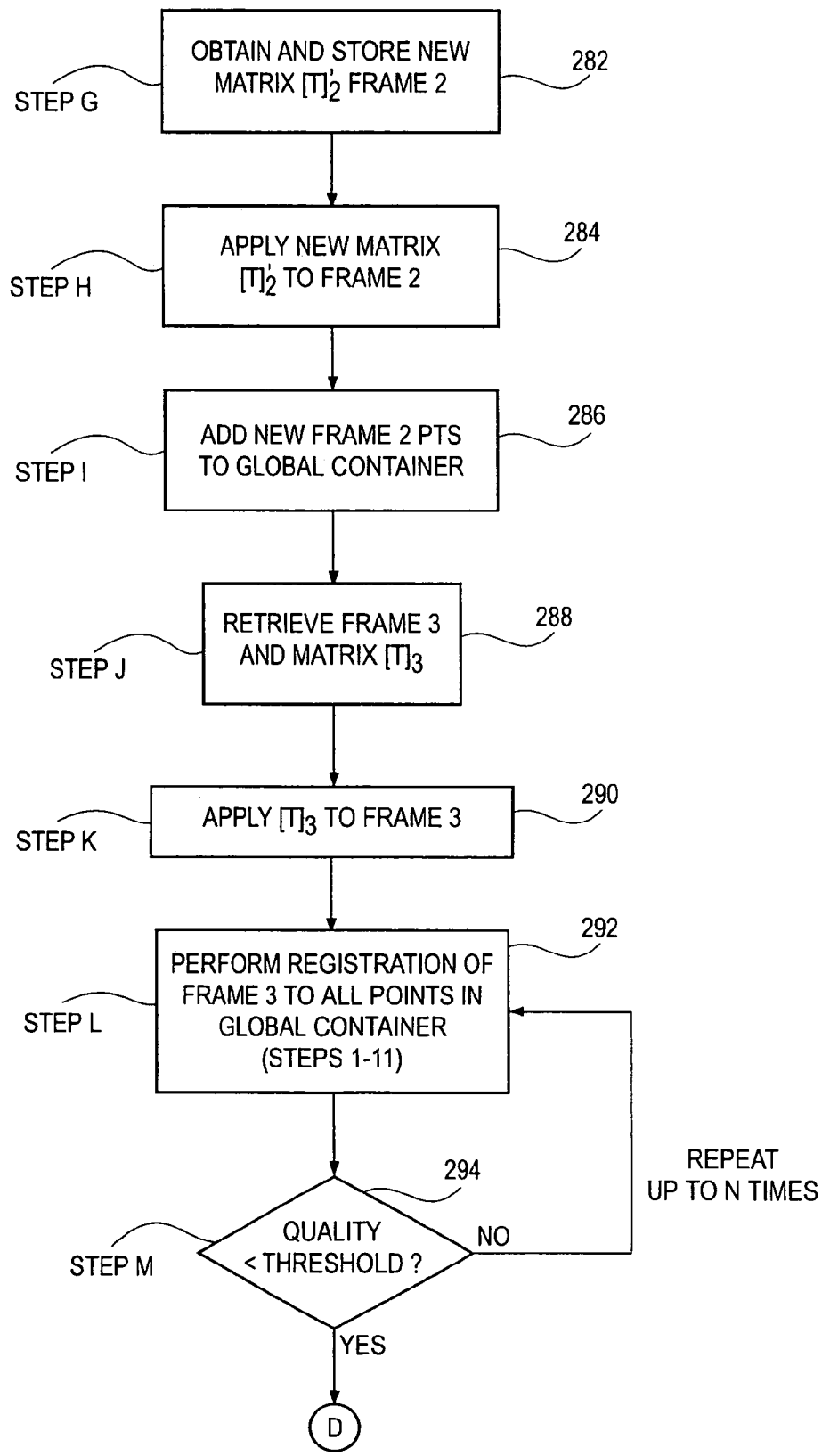
Figure 48C:
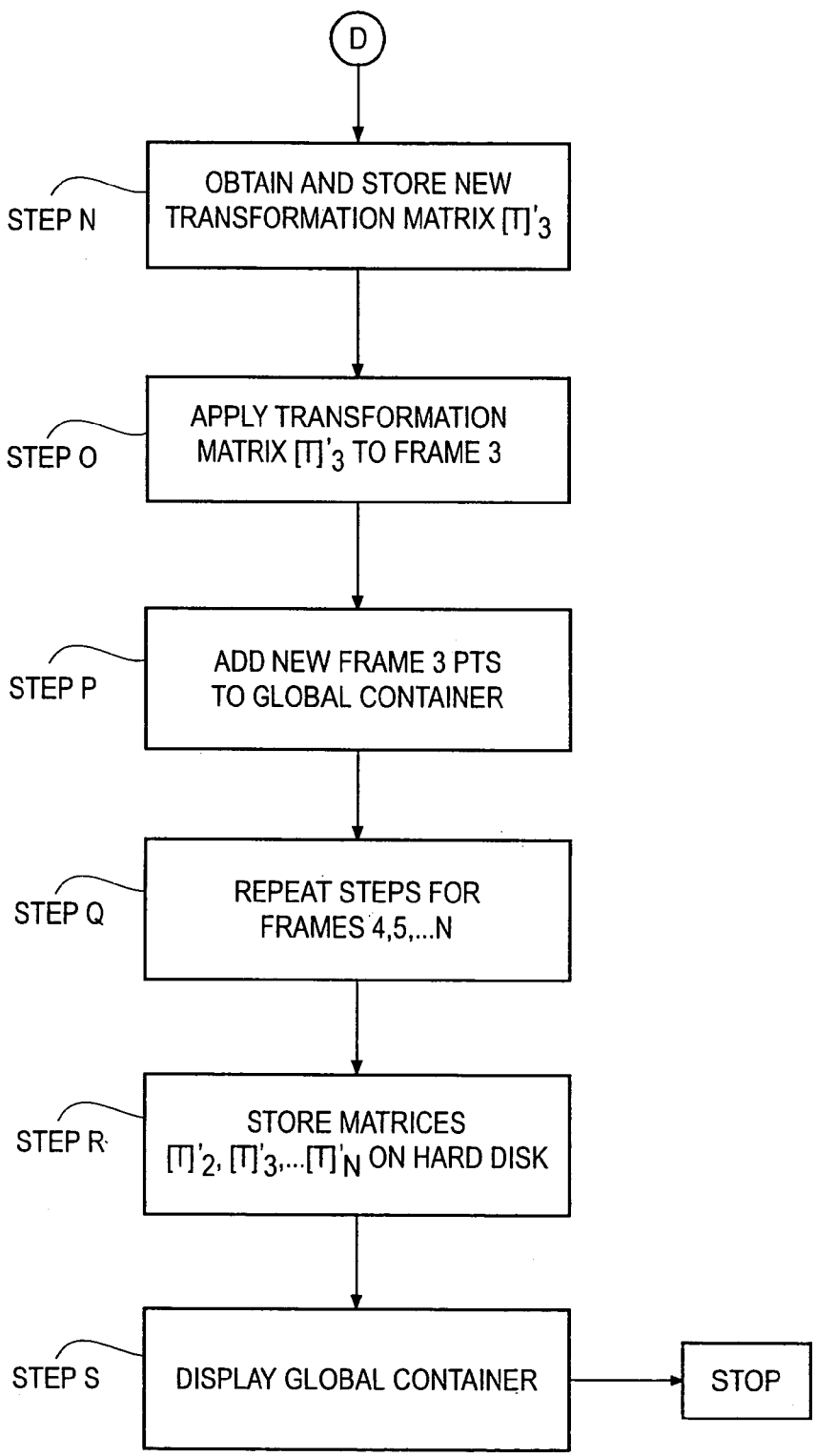

FIG. 48A–48C are a flow diagram of one possible cumulative registration process. At step A (270), the points of the first frame are retrieved from memory.

At step B (272), the points of the second frame are retrieved from memory.

At step C (274), the transformation matrix $[T]_2$ is retrieved for frame 2. This process assumes that the transformation matrix for each frame has already been generated, such as after a frame to frame registration process has been performed.

At step D (276), the transformation matrix $[T]_2$ is applied to frame 2.

At step E (278), a registration is performed of the points of frame 1 to the points of frame 2, after the transformation matrix $[T]_2$ has been applied to frame 2. Basically, the steps 1–11 of FIG. 40A–40B are performed.

At step F (280), a check is made as to whether the quality of the registration is less than a threshold. If not, the registration is performed again (with the points of frame 2 updated by a new transformation matrix). Steps 278 and 280 are performed over and over again until either the quality threshold is met or a maximum number of iterations has occurred.

If the index is met or the maximum number of iterations has been reached, the process proceeds to step G (282). The new transformation matrix for frame 2, designated $[T]_2'$ is obtained and stored.

At step H (284), the new transformation matrix $[T]_2'$ is applied to the points of frame 2.

At step I (286), the new transformed points of frame 2 are added to a "global container". The global container is merely memory locations containing the points from frame 1 and the points of frame 2 as transformed.

At step J (288), frame 3 and its transformation matrix $[T]_3$ is obtained from memory.

At step K (290), the transformation matrix $[T]_3$ is applied to the points of frame 3.

At step L (292), a registration is performed of frame 3, as transformed, to all the points in the global container. Steps 1–11 of FIG. 40 are performed.

At step M (294) a check is made to see if the quality index is below the threshold. If not, another iteration of the registration process is performed. This repeats until the quality index is below the threshold or a maximum number of iterations is reached.

If the threshold is met (or the maximum number of iterations is reached), the process proceeds to step N (296). The new transformation matrix $[T]_3'$ is obtained and stored in memory.

At step O, this new transformation matrix is applied to the points of frame 3.

At step P (300), the points in frame 3 after the transformation operation is performed are added to the global container.

At step Q (304), the process of steps A–P of FIG. 48 are performed for the rest of the N frames.

At step R, all the transformation matrices $[T]_2' \ldots [T]_N'$ are stored on the hard disk of the back office server. These transformation matrices are used whenever the finished global container (complete three-dimensional model) needs to be generated again at a later date (or on another workstation). The model is generated by simply applying $[T]_2' \ldots [T]_N'$ to the raw frame data comprising frames 2 . . . N.

At step S, the global container is displayed to the user. This can be on the monitor of the back office server 28 or on the monitor 20 of the scanning station 16 (FIG. 1). Since the global container is a digital representation of the object, it can be transported across a computer network and displayed and shared by another terminal. For example, where the back office server has a connection to the Internet, the model can be transported over the Internet to the precision appliance service center 26 and displayed there. It can also, for examples be shared among various orthodontic, periodontal or dental specialists so that they can collectively study the patient remotely and cooperatively plan care.

Figure 49:
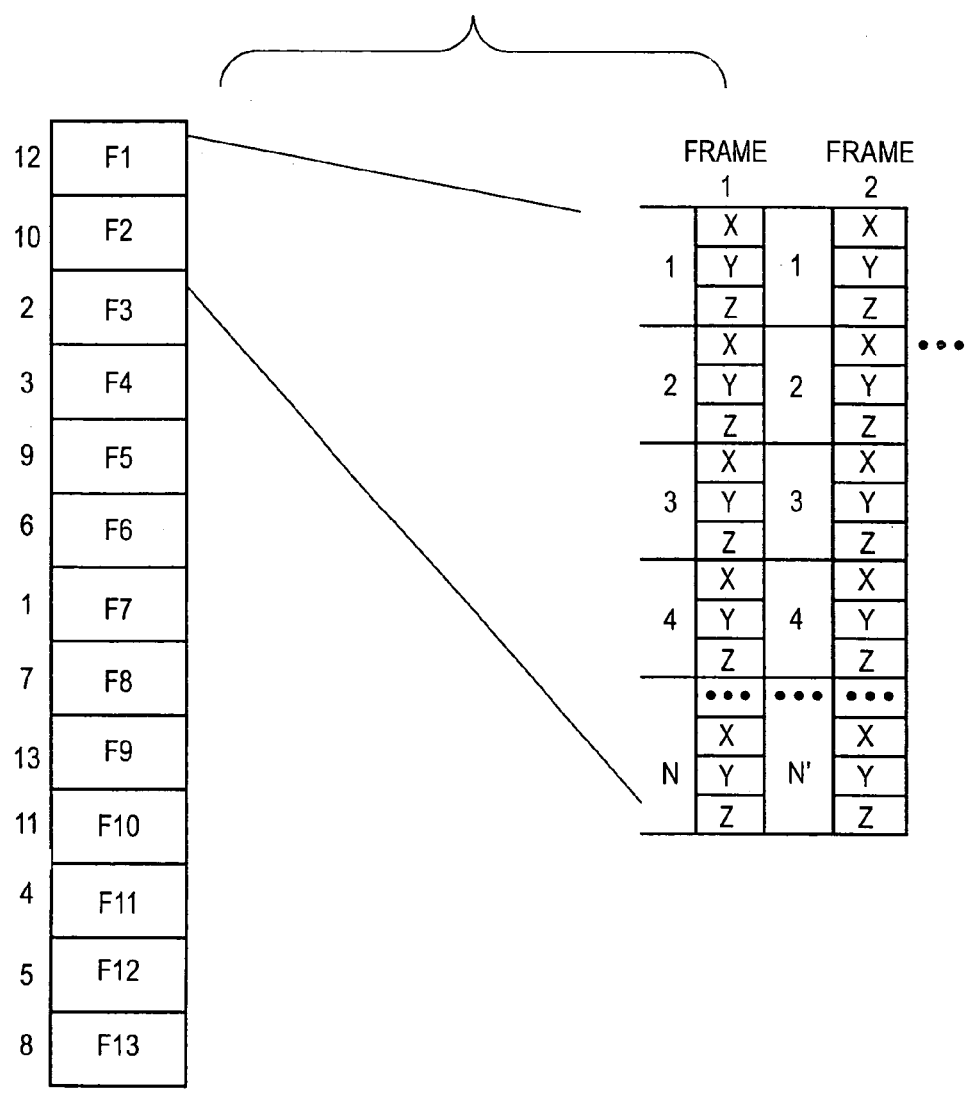
FIG. 49 is an illustration of a set of frames illustrating a different order for frame registration than frame to frame registration, with the order based on the location on the surface of the object for a given frame relative to the location on the surface for other frames.

FIG. 49 is an illustration of a set of frames, illustrating a variation from the cumulative registration set forth in FIG. 48. In FIG. 49, a different order of frame registration is performed from that of frame to frame registration. In particular, frame to frame registration and cumulative registration of FIG. 48 are performed in the order in which the frames are obtained. This need not be the case. In fact, a more accurate registration may be obtained by registration of frames in an order based on "neighborliness", that is, based on the concept that all frames imaging a particular portion of an object should be registered together (or in sequence such they are registered one after the other). The order of registration is indicated by the left hand column of numbers. The right hand side of FIG. 49 merely illustrates that each frame consists of X, Y and Z coordinates for a set of points. The frames need not and usually will not have the same number of points.

Figure 50:
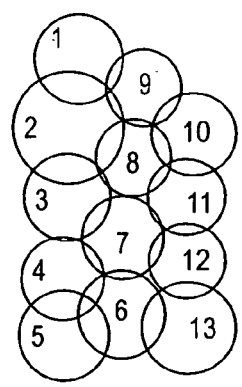
FIG. 50 is a simplified illustration of a set of frames, showing the order in which the frames were obtained, with the neighborliness of the frames relative to other frames being the basis for the registration order shown in FIG. 49.

In FIG. 49, the registration order is based on the location on the surface of the object for a given frame relative to the location on the surface for other frames. FIG. 50 is a simplified illustration of a set of frames, showing the order in which the frames were obtained, with the neighborliness of the frames relative to other frames being the basis for the registration order shown in FIG. 49. Frame 7 (F7) is the chosen starting frame. So, the frames surrounding frame F7 are registered next. This is shown by the order of registration being F7, F3, F4, F11, F12, F6, . . . as indicated.

Figure 51:
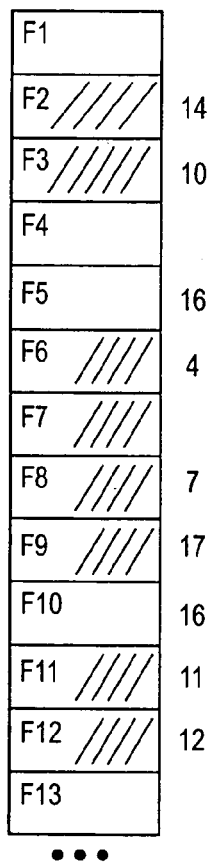
FIG. 51 is another illustration of a set of frames, with registration of frames performed in accordance with the method of FIG. 49, with the marking in frames 2, 3 6 and 7 etc. indicating that that frame has been registered. The marking is just a way of illustrating that the computer keeps track of which frames have not been registered, as a check to insure that no frames are omitted during the registration procedure of FIG. 49.

FIG. 51 is another illustration of a set of frames, with registration of frames performed in accordance with the method of FIG. 49. The order of registration is indicated by the column of numbers to the right of the frames. The marking in frames 2, 3, 6 and 7 etc. indicates that those frames have been registered. The marking is just a way of illustrating that the computer keeps track of which frames have been registered, as a check to insure that no frames are omitted during the registration procedure of FIGS. 49 and 50. The manner of selecting the other frames, e.g., frame 4 and 5, can be based on a number of criteria, such as the order of obtaining the frame, the neighborliness to other frames already registered, and so forth.

Figure 52:
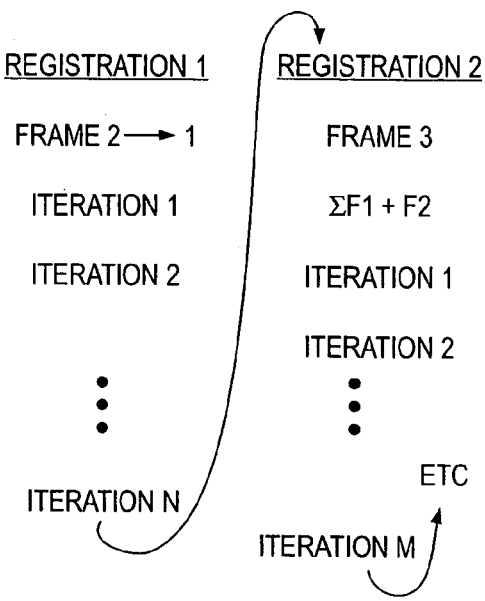
FIG. 52 is an illustration of cumulative registration based on the first captured frame (F1) as being the base line for all successive registrations.
Figure 53:
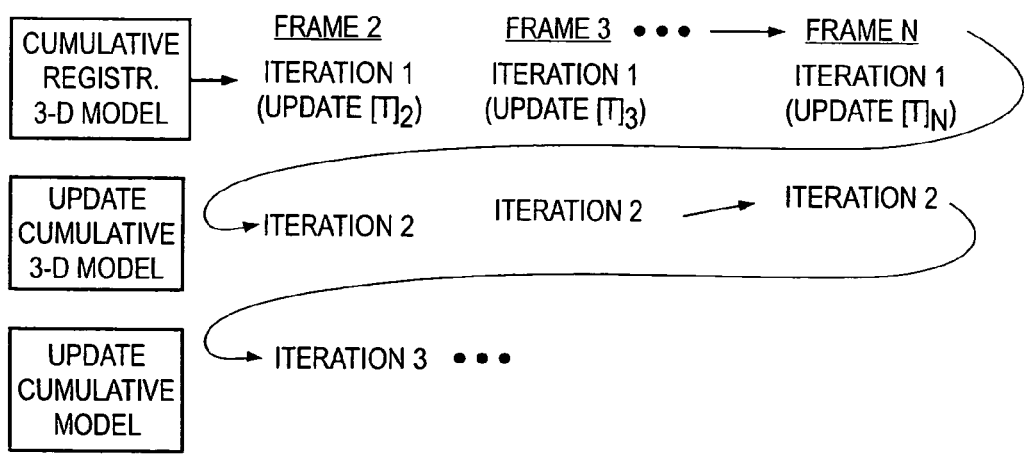
FIG. 53 illustrates an alternative registration procedure in which each frame in the set of frames is registered to a cumulative registration 3-dimensional model of the object, in sequential order, with one iteration of the frame registration process. This is followed by an updating of the cumulative 3-dimensional model and a repeat of the registration process with updated values for the transformation matrix [T] for each frame.

FIG. 52 is an illustration of cumulative registration based on the first captured frame (F1) as being the base line for all successive registrations. This is essentially the technique of FIG. 48. FIG. 53 illustrates an alternative registration procedure in which each frame in the set of frames is registered to a cumulative registration 3-dimensional model of the object, in sequential order, with one iteration of the frame registration process. This is followed by an updating of the cumulative 3-dimensional model and a repeat of the registration process with updated values for the transformation matrix [T] for each frame. The process continues until the quality values are within acceptable limits, or after a predetermined number of iterations have been performed. Still other possibilities for cumulative registration exist. The choice of which one to use will depend on the available computing resources, the amount of time required to perform the cumulative registration for the technique, and the desired accuracy.

FIG. 54 is a screen shot of a workstation computer (e.g., either a scanning station or back office server workstation), showing the available registration parameters and variables that can be changed to optimize the registration when performing either a frame to frame registration or a cumulative registration. The parameters may vary widely depending on the type of object being scanned, the amount of time needed to obtain a result from registration, the speed at which the scanner is moved relative to the object and the amount of overlap, etc. FIG. 54 illustrates that the user is able to select and modify the registration procedure parameters as they see fit. Two different types of registration are indicate here, a "raw" registration, in which the quality index ("distance limit") is 250 microns, and a fine registration, wherein the quality index is reduced to 50 microns. The distance limit is computed as the square root of the sum of the squares of the normal vectors divided by the number of points in the frame. The term "stationary count" indicates the number of iterations to continue of little or no improvement in the quality index is seen. The Radius value refers the filter R shown in FIG. 45. The convergence factor 0.10 refers to the minimum amount of improvement needed between successive frames before a stationary count commences. The convergence factor is computed by taking the difference of the squares in the quality index of the ith iteration and the i−1 th iteration and dividing by the square of the quality index of the ith iteration.

The number of points to register indicates the minimum amount of overlap in points (within boundary R) needed to attempt a registration. An "accelerate" factor is shown, with a value of 1.6. This means that the points are moved in the X, Y and Z directions in the transformation matrix by an amount of the net normal vector multiplied by the accelerate factor. The use of an accelerate factor has been found to reduce the number of iterations required to meet the quality index.

The maximum iteration count value is a stop value to keep the process from running into an endless loop. The overlap size value is a limit, in terms of $mm^2$, of the size where registration is performed. This serves to screen out stray points from the registration algorithm. The minimum quota of active points is a minimum amount of overlap between two frames before registration will be attempted, expressed as a fraction of 1. The maximum triangle size is a filter to filter out triangle sizes where the size of the triangle is too large, indicating a stray data point. The maximal edge length is simply the maximum permissible length of one side of one of the triangle surfaces. The Maximal count of unsuccessful files is the number of unsuccessful sequential registrations before a failure of the registration process will be declared.

Figure 55:
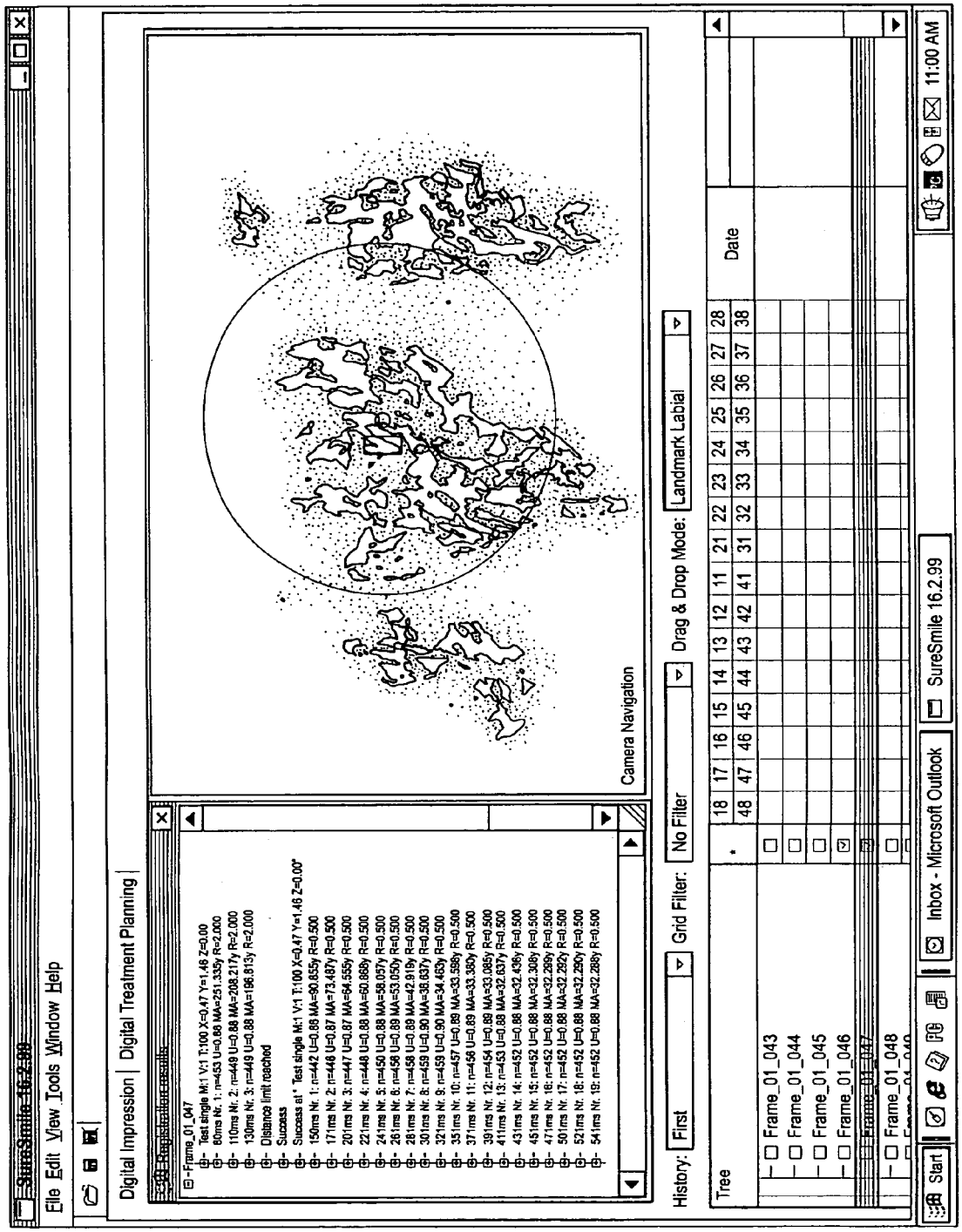
FIG. 55 is a screen shot from a workstation computer showing a frame to frame registration in accordance with FIG. 40 for two frames in a set of frames.

FIG. 55 is a screen shot from a workstation computer showing a frame to frame registration in accordance with FIG. 40 for two frames in a set of frames. The various parameters shown in FIG. 54 are selected and used in the frame to frame iteration. In this instance, frame 47 is being registered to frame 46. The surface of frame 46 is shown in white, frame 47 is shown in dark tones. The left hand side of FIG. 55 shows the results of each iteration, including the running time, the number of the iteration, the number of overlapping points, the overlap between frames (U), expressed as a fraction of 1, the quality index MA, and the value of the filter R. After 3 iterations, the quality index for coarse registration was met. The process continued with the fine registration. A series of fine registration iterations were performed. Note that the quality index MA improves with each registration iteration.

Figure 56:
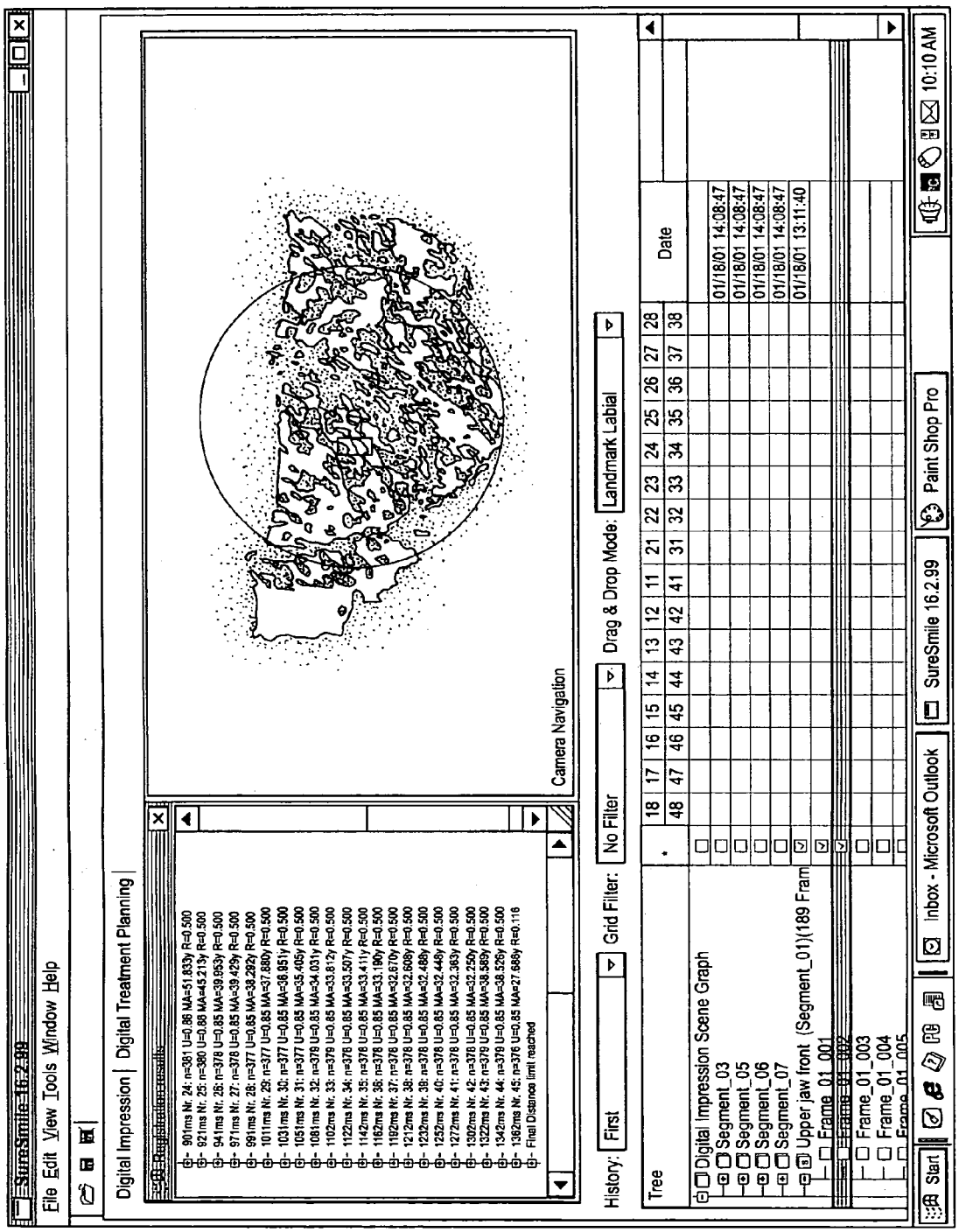
FIG. 56 is a screen shot showing the results after forty five iterations of the frame to frame registration process of FIG. 40, and with the right hand side of the screen shot showing the two frames superimposed on each other.

The data from the last twenty iterations, and the final result, of a registration of frame 2 to frame 1 in a typical scan of teeth are shown in FIG. 56. After 45 iterations, the distance limit of 30 microns was met (MA=27.686 microns). Note that the graphical representation of frame 1 (white) and frame 2 (darker tones) is such that there is essentially an equal amount of frame 1 and frame 2 in the picture. This indicates that a "best fit" between frames 1 and 2 has been achieved.

D. Segment Registration

When scanning any object, such as teeth, the situation may arise in which the operator of the scanning cannot capture all the surfaces of the object in one scanning pass. The interruption may be due to the need to physically move the scanner to a location that is impossible to reach from one location, the need for the patient to take a break from the scanning, or some other reason. When scanning teeth of a single jaw, the scanning is typically performed in two or three different segments. First, one side of the jaw is scanned, then the front of the jaw, and then the other side of the jaw. In this situation, there are three different segments of the object. All the frames of each segment are registered to each other, typically using a frame to frame registration. Then the segments are registered to each other. After this has been done, a cumulative registration is performed of the entire jaw.

To perform the segment registration, there must be some way of indicating where at least one point in one segment is common to another segment. Segment registration thus requires some overlap between segments. The scanning workstation provides a mechanism to indicate at least one point where two different segments overlap. In the case of the scanning of teeth, the operator of the scanner will typically include the canine teeth in scans of both sides of the jaw, and in the scan of the front of the teeth. The operator can also be instructed to scan these teeth in the side and front segments. Therefore, the segment registration proceeds by the user selecting or indicating a point on the canine teeth to use for performing segment registration. A procedure referred to herein as "landmarking" is used to select the point used to register segments. It will be understood that a similar process will be performed when scanning other types of objects where more than one segment was used to completely scan the object.

E. Landmarking

Figure 57:
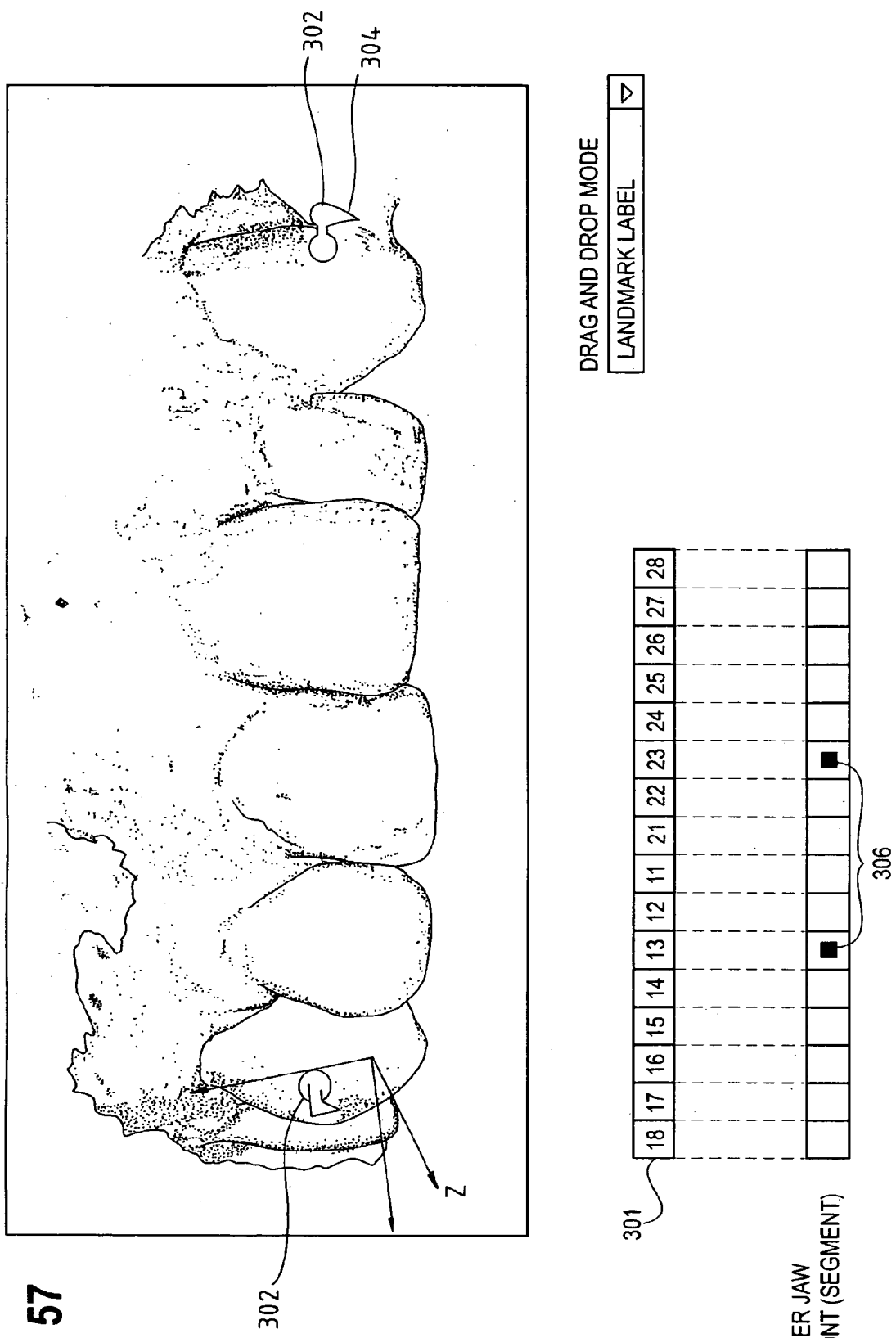
FIG. 57 is a screen shot showing a graphical representation of a three-dimensional model of a patient's upper front teeth after a frame to frame registration. The user is applying landmarks to the teeth as a preliminary step in treatment planning, and as a step in registering overlapping segments of a scanned upper jaw relative to each other to calculate a complete model of the upper jaw and associated dentition.

FIG. 57 is a screen shot showing a graphical representation of a three-dimensional model of a patient's upper front teeth (segment 1) after a frame to frame registration of this segment. The user is applying landmarks to the canine teeth as a preliminary step in treatment planning, and as a step in registering overlapping segments of a scanned upper jaw relative to each other to calculate a complete model of the upper jaw and associated dentition.

The purpose of the landmarking shown in FIG. 57 is to select a point on the canine teeth which is common to the front scan and the two side scans. The landmarking is also done at a point on the labial surface of the teeth that would be a suitable location for placement of an orthodontic bracket as part of an appliance to correct a malocclusion. The landmarks are characterized by both a point location and an orientation. To place the landmarks, the user clicks on a tooth number, indicated by the row of numbers 301, and drags the cursor with a mouse to the surface on the canine teeth where they wish to place the landmark. They then release the cursor, and the landmark 302 appears on the tooth. The landmark has an arrow 304 which must point to the incisal edge of the tooth. The user can rotate the landmark to place the arrow in the proper orientation by simply clicking on the landmark and turning the mouse one way or the other. As each landmark is placed, a box below the tooth number is highlighted as indicated at 306.

The tooth numbering convention shown in FIG. 57 is as follows: the first number indicates the quadrant of the patient's dentition, with 1 being upper right, 2 being upper left, 3 being lower left, 4 being lower right. The second number is the tooth number with 1 being the incisor. Thus, the landmarks are placed at teeth 13 and 23, the upper canines.

Since these canines overlap their respective side scan, and since the X, Y and Z coordinates of the point on the labial surface of the tooth where the landmark is placed is assigned in the computer, it is now possible to register the front segment shown in FIG. 57 to the two side segments. This segment registration is now performed. The overlapping frames between each segment can be registered to each other, or to the entire other segment.

After segment registration is performed, a cumulative registration of the entire jaw is performed in accordance with the procedure of FIG. 48. After the cumulative registration is performed, the virtual three-dimensional model of the entire jaw is presented to the orthodontist on the monitor in the back office server workstation 28.

Note that if the scanning is done in one pass, e.g., where it is performed on a plaster model, there is no need for segment registration. The landmarking step can be eliminated in that event, although it may nevertheless be performed as a step in placing virtual brackets on the teeth objects of the virtual model.

In planning treatment for the patient, the orthodontist conceptualizes teeth as individual teeth objects that can be moved independently of each other to correct the patient's malocclusion. Furthermore, orthodontists are trained to make physical models of the patient's dentition from an impression, cut the teeth from the model, and then individually move the teeth relative to each other to provide a target situation which corrects for the malocculsion. Therefore the back office server workstation 28 includes interactive treatment planning software which enables the orthodontist to do this with the virtual three-dimensional model of the patient's dentition. In order to do this treatment planning, it is highly desirable therefore to process the three dimensional model resulting from a cumulative registration by separating the teeth from the gums and other anatomical structure, and presenting the just crowns of the teeth to the orthodontist. This allows virtual individual teeth objects to be moved independently in three dimensions on the computer. This process of separation of the teeth from the cumulative registration into individual teeth objects will be described next.

The separation process described below has one further advantage, namely requiring less memory to represent an individual tooth. Cumulative registration may result in an extremely large number of points from a large number of frames to represent any given tooth. The separation process, as described below, reduces this data set to a single set of points that describe a single surface representing the surface of the tooth. Much less memory is required. Consequently, the treatment planning software can process treatment planning steps for the teeth more quickly.

E. Separation of Teeth into Individual Tooth Objects (Tooth Modeling)

FIG. 58A–58F are a series of illustrations showing the generation of an individual tooth model from a scanned tooth. The process will now be explained in detail.

Figure 58A:
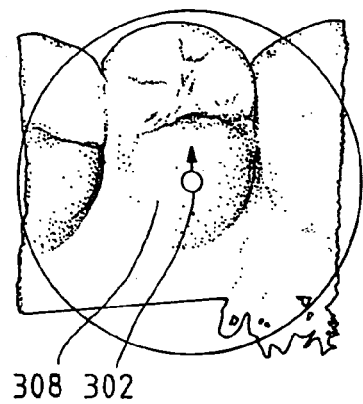
FIG. 58A–58F are a series of illustrations showing the generation of an individual tooth model from a scanned tooth, shown in FIG. 58A, and a template tooth, shown in FIG. 58B. A library of template teeth similar to FIG. 58A are stored as three-dimensional computer models in computer memory. The individual tooth model is a three-dimensional tooth object having a single set of points defining the boundaries of the tooth. The individual tooth model reduces the amount of data required to represent the tooth, as compared to the data representing the tooth after a cumulative registration of a large number of frames. Individual tooth models are also invaluable in interactive orthodontic treatment planning since they can be independently moved relative to each other in simulation of treatment scenarios.
Figure 58B:
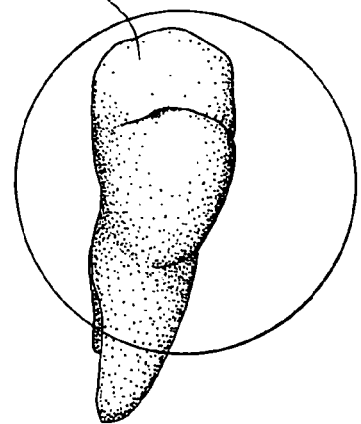
Figure 58C:
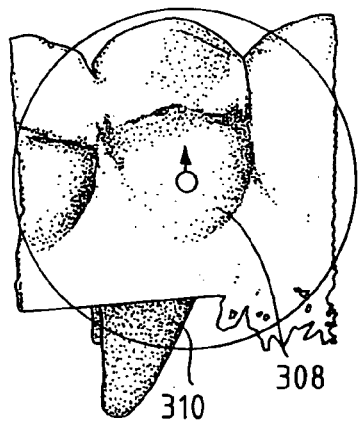

FIG. 58A shows the scanned dentition and associated anatomical structure surrounding the tooth 308. This tooth is tooth number 14 in the numbering convention shown in FIG. 57. The back office server workstation stores a three-dimensional virtual template tooth object for each tooth in the maxilla and the mandible. The template tooth 310 for tooth number 14 is shown in FIG. 58B. The template tooth object 310 is a three-dimensional tooth object having a single set of points defining the boundaries of the tooth. As shown in FIG. 58C, the template tooth 310 is positioned approximately in the same location in space as the tooth 308. The landmark 302 assists in providing the proper axial rotation of the template tooth to have it fit properly with respect to the tooth 308. The template tooth is placed at the point cloud of the dentition according to the labial landmark 302. The template tooth can be scaled larger or smaller or positioned arbitrarily by the user, in order to get a close a position as possible to the point cloud of the dentition.

Figure 58D:
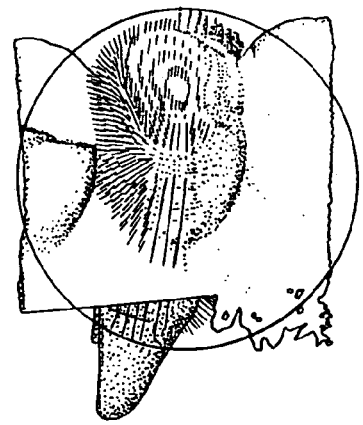
Figure 58E:
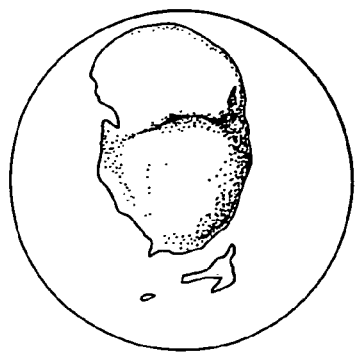
Figure 58F:
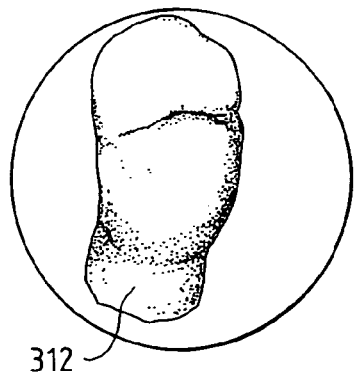

As shown in FIG. 58D, vectors are drawn from the points on the template tooth to the scanned point cloud of the tooth 308. Every ray intersects several surfaces, depending on how often the respective part of the surface has been covered during scanning. For each vector, a surface is selected. Preferably, the smallest triangle surface is selected, since this surface corresponds to an image taken by the scanner when the scanner was positioned in a more perpendicular orientation to the dentition surface, resulting in more accuracy in the determination of the coordinates of that portion of the surface. As another possibility, the outermost surface is selected, using a filter to insure that no extraneous surfaces are used. These points of the surfaces intersected by all the vectors are combined as newly generated triangle surfaces and therefore form one consistent surface shown in FIG. 58E. Then, finally, missing parts of the tooth are completed from the template tooth. The result is shown in FIG. 58F. In a second pass, this generated object is then used as a template tooth, and the steps indicated by FIG. 58C–58F are repeated in an iterative fashion. This is done to make sure that the algorithm works even if there are significant differences between the original template tooth and the scanned point cloud, e.g, a gap in scan data, different geometry in the tooth. The goal is to provide an algorithm that does not required a closely fitting template tooth object.

Figure 59:
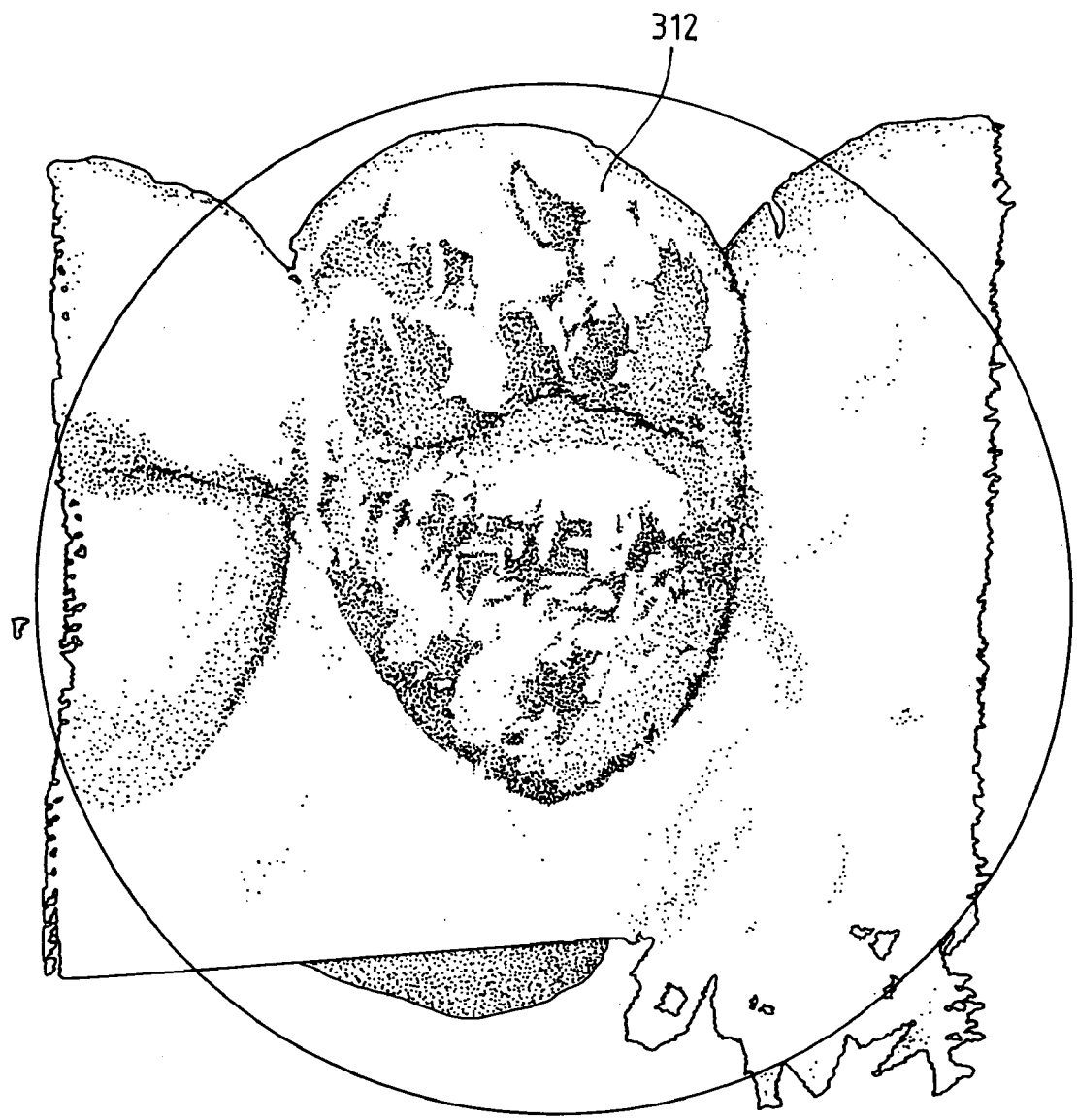
FIG. 59 is an illustration of the tooth model of FIG. 58D positioned in the computer model of the patient's dentition, surrounded by other anatomical structures.

The final result, an individual three-dimensional virtual tooth object 312, is then displayed to the user, as shown in FIG. 59. The result may be displayed on the workstation user interface as a three-dimensional superposition of the original data (white) and the separated model of the tooth (darker tones or contrasting color). These tones allow the user to ascertain whether there is an even distribution of white and dark tones, indicating good fit between the scanned tooth 308 and the individual tooth object 312. This step may be automated by an algorithm detecting the difference (or the sum of the differences), and repeating the process if the difference is too great.

This process is of course performed for all the teeth. The result is a set of individual tooth objects for all the teeth in the patient's dentition. The teeth can be displayed either alone, or in conjunction with the surrounding anatomical structures such as shown in FIG. 59.

Some human interaction is used in the embodiment described above in context of FIG. 58. While the process could be performed for all the teeth in both arches on the workstation at the orthodontic clinic, that is not necessary. In particular, since the virtual model of the dentition and the template teeth exist as digital data in memory, they can be transported to a remote location and the task of separation of the dentition into virtual teeth objects could be performed at another location. This has the advantage of not tying up the back office workstation or server 28 in the clinic unduly, and requiring less labor at the clinic. We therefore contemplate that the function could be performed as a service of the precision appliance service center 26 of FIG. 1, or perhaps even by some other entity or service provider equipped with the necessary computer hardware and software. Once the virtual tooth objects are obtained for all the teeth in the dentition, the set of virtual tooth objects could be sent over the Internet back to the clinic for treatment planning and other purposes. It would also be possible for the entity performing the separation of tooth objects to also present an initial proposed treatment to the orthodontist (such as a target situation, location of brackets, and design of orthodontic archwire), and let the orthodontist take the process from there or simply indicate her approval.

Separation of teeth from the virtual model of the dentition could also be performed automatically using algorithms to detect incisal edges of the teeth, grooves between teeth, and grooves indicating the intersection of the gums and the teeth.

Two types of errors can occur when separation of teeth objects from other structure (e.g., other teeth and gums): 1) the data is selected for a tooth that does not in actuality belong to the tooth, such as gums and adjacent teeth, and 2) data that does belong to the tooth is ignored.

We address the first problem by providing an erase mode on the workstation software that is performing the modeling process. In this mode, the user is provided with a tool that erases triangle surfaces from the 3-D data, e.g., by highlighting unwanted areas with a mouse and clicking an erase icon or other similar technique. As each tooth is modeled individually, parts of the data that represent the unwanted data, e.g., data belonging to other teeth or gingival tissue, are eliminated from the tooth. This is only a temporary process; it is used only to model that tooth and underlying scanned data is preserved. When modeling the adjacent tooth, that data is used again. The erasing process can be performed directly on the original scan data. However, this can be inconvenient since the original scan data can consist of a huge overlay of data.

As an alternative, and more preferred approach, the user works on a tooth model that has already been created and consists of one shell of triangles. Thus, the erasing mode would be used for example after one iteration of the process of FIG. 58A–F. The selection and erasing process is much faster. The modeling algorithm calculates the surfaces to be deleted from the model in a single pass. The remainder of the iterations of the process of FIG. 58 can typically be performed without any further erasing.

Figure 64A:
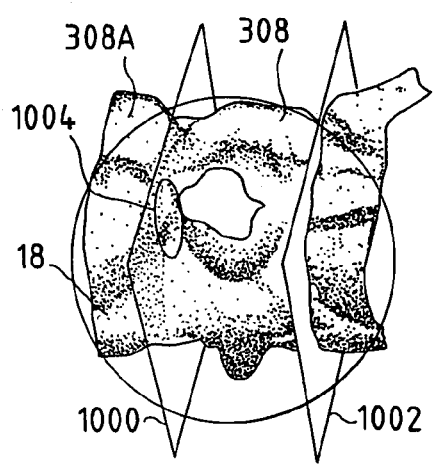
FIGS. 64A–64D are four views of a virtual model of a portion of the dentition generated by the scanning system of FIG. 1, illustrating alternative methods for separating teeth from associated anatomical structure, e.g., other teeth and gingival tissue, as a part of the process described in conjunction with FIG. 58A–58F.

As another alternative for elimination of unwanted data, cutter plane tools can be provided on the workstation software to assist the user in selection of correct tooth scan data. The activation of this feature is shown in FIG. 64A. In this technique, two planes 1000 and 1002 are superimposed on the scanned virtual model 18 of the dentition. The user is able to translate or rotate the planes 1000 and 1002 in any orientation in space using suitable navigation tools on the workstation 28 user interface. The planes may be in different colors. The planes serve as boundaries for the selection of tooth scan data as an individual virtual tooth object, or as part of the iterative procedure of FIG. 58. All 3-D data that is outside of the planes 1000 and 1002 is ignored. The intention of the planes of FIG. 64A is to simulate the physical process of cutting a physical model of teeth into discrete tooth objects.

FIG. 64A indicates that the two planes may not work perfectly since teeth are curved or crooked at the contact area between adjacent teeth, and the plane 1000 may in fact intersect two different teeth. In FIG. 64A, the area in region 1004 indicates where some triangle surfaces from the adjacent tooth 308A are included in the region between the two planes 1000 and 1002. These parts of tooth 308A can be manually erased by the erase mode feature described above.

Figure 64B:
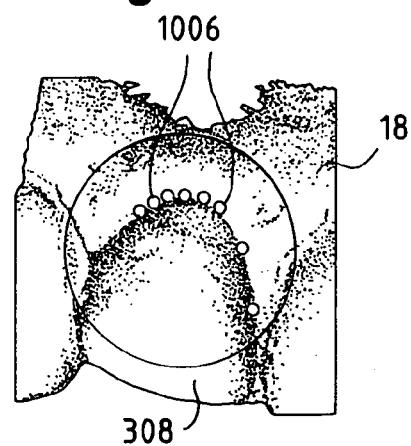
Figure 64C:
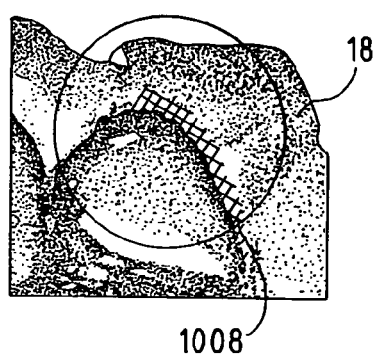
Figure 64D:
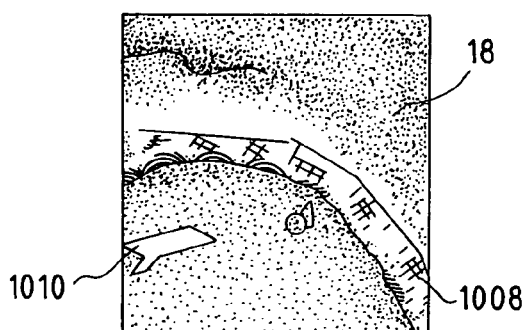

Another possible method for separation of the teeth, without including extraneous anatomical structures, involves allowing the user to click with a mouse multiple points on the surface of the tooth where the tooth intersects adjacent anatomical structures. In FIG. 64B, the user has highlighted areas 1006 on the tooth 308 where the tooth intersects gingival tissue. As each area is highlighted and selected (e.g., by a click of the mouse), the software records the coordinates of points associated with these areas 1006. Then, a series of planes are constructed which connect these points (or surfaces) together. These planes 1008 are indicated by the hatched area of FIGS. 64C and 64D. The planes 1008 serve the same functions as the cutter planes 1000 and 1002 of FIG. 64A; i.e., they define a boundary separating the tooth from associated non-tooth anatomical structures, such as gums and other teeth. Depending on the anatomy of the patient, it may be necessary to highlight closely-spaced areas, as shown in FIG. 64B, so that the planes 1008 match the contours of the gum and tooth.

Referring now to the second problem, the tooth separation process of FIG. 58A–F can be forced to use proper data that would otherwise be ignored. Specifically, the user clicks certain areas where original scan data has been wrongfully ignored. Clicking on the area forces the modeling algorithm to pick original data points from the scan including the selected areas. For example, region 1010 in FIG. 64D has scan data associated with it, but such data was ignored in a frame to frame registration process. The user highlights this area and points for those areas are filled in from the original scan data for pertinent frames covering this area.

To allow for a safe operation of this user interaction, the modeling algorithm will internally mark or classify each generated point in the virtual tooth model as being based on scan data (true points), or if it has been constructed by the algorithm due to the lack of data (artificial points, supplied by the template tooth 310 in FIG. 58B). A lack of data will always occur in the spaces between teeth since the scanner cannot usually capture images of the gaps between teeth effectively. A lack of data can also occur due to improper scanning. The lack of data can be cured to a certain extent by the modeling algorithm of FIG. 58, with the lack of data supplied by the template tooth, e.g., in the gaps between teeth, and adapting this template tooth to the scanned dentition as described above. Artificial points can be marked as such and displayed in a different color or using lighter or darker tones. The manipulations of the user described above for wrongfully ignored data will have effect only on the artificial surfaces.

Figure 65:
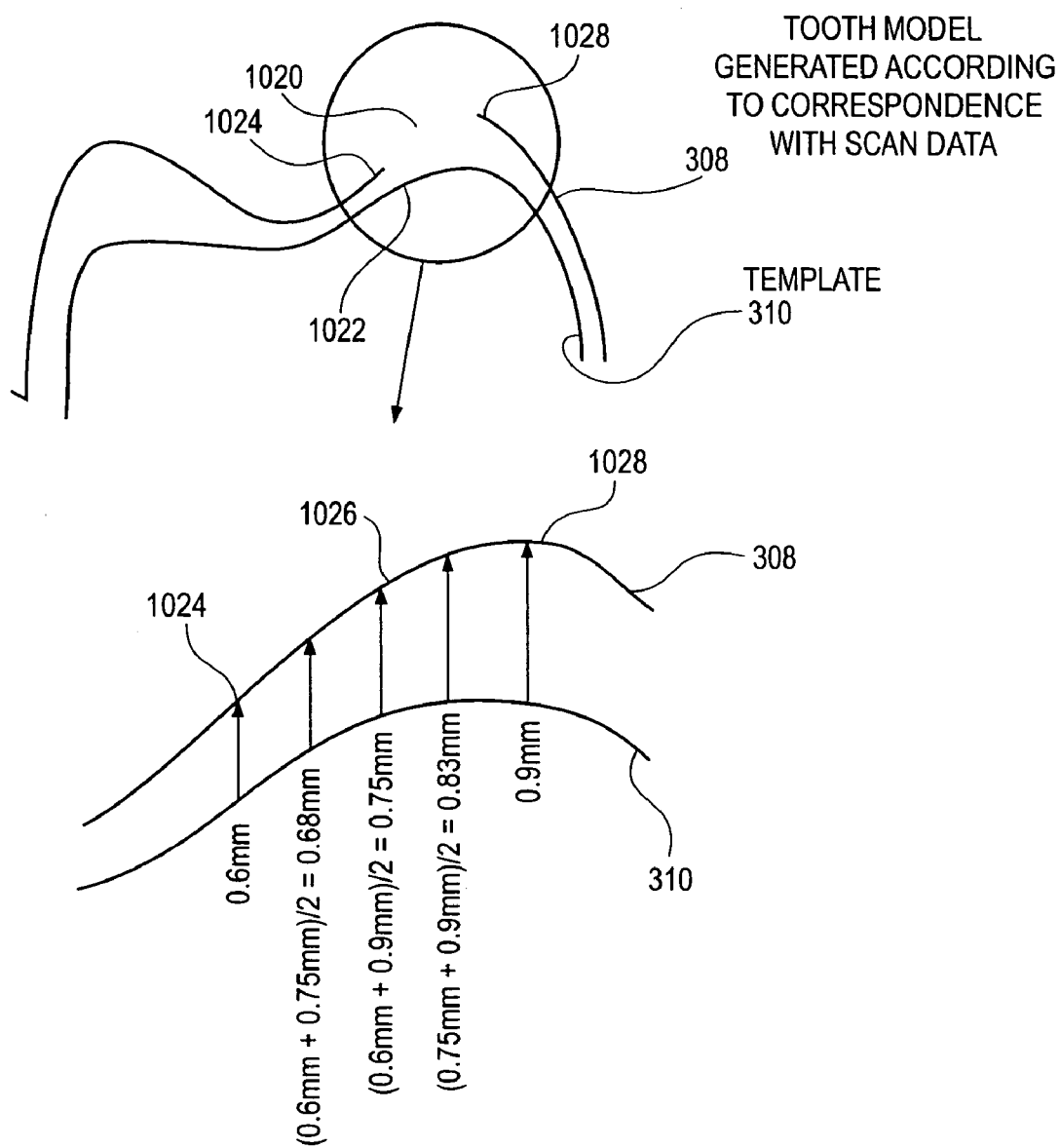
FIG. 65 is an illustration of an interpolation procedure that can be used in the process described in conjunction with FIGS. 58A–58F to fill in holes in scan data from a template object.

Missing data or gaps from the tooth scan can also be filled from the template tooth using a simple interpolation procedure, such as shown in FIG. 65. The example of FIG. 65 will be given in one dimension (Z); a similar process occurs in the other dimensions X and Y. As shown, the scan data for the tooth 308 includes a gap indicated at 1020. The template tooth includes a surface 1022 that corresponds to this gap. To fill in the surface, the distance in mm is determined between the point at the left hand edge of the gap 1024 and the template surface 310 in the Z direction (0.6 mm). The same is done for the right hand edge 1028 (0.9 mm). A mid point is chosen 1026 and the values are averaged to arrive at the distance for point 1026 (0.75 mm) This process is repeated for intermediate points as indicated. After a suitable number of interpolations, the points in the template tooth 310 are moved in the Z direction by the measured or calculated amounts, here 0.6 mm, 0.68 mm. 0.75 mm. 0.83 mm. 0.9 mm. These points are now connected by lines to form triangle surfaces to complete the surface of the tooth 308.

The tooth model, once created, can be modified to simulate various treatments that may be made on the tooth, such as interproximal reduction, or grinding portions of the tooth away, by using the erase mode, clipping planes similar to the planes 1000 and 1002 of FIG. 64A, or some other convenient means.

The library of standardized template teeth described above is based on standard tooth models for each teeth in one possible embodiment. The library described above could be augmented to include a library of teeth based on the ethnicity, sex, age, or other factors. For example, the library could consist of one library of template teeth for Hispanics, another library of template teeth for Orientals, a third library of template teeth for Caucasians, etc. These libraries could be supplied with the treatment planning software, obtained from a third party, or even created from patient scans. For example, after each scan using the present system, the software cuts the teeth into individual tooth objects using the process described above and stores the teeth in memory, along with identifying indicia such as the race, sex and age of the patient.

Over time, a large collection of virtual tooth objects for various types of patients will be obtained. These virtual teeth can be registered to each other for a given ethnic type, on a tooth by tooth basis, to result in a new library of template teeth for a given ethic group, which are stored in memory. The user can thereafter identify for the software which library of template teeth to use for a new patient based on the relevant criteria such as ethnicity.

Alternatively, in some situations it may be desirable to use a contralateral tooth as the template tooth, and not a template tooth from the library of template teeth. In this situation, a tooth object of one of the contralateral teeth is obtained from a template tooth in a library and the cumulative registration scan. Then, the tooth object of the contralateral tooth is obtained by using the contralateral tooth as the template tooth and the cumulative registration scan as explained above.

In some situations, the template tooth may need to be modified. A few example of such situations are a partially erupted molar, a tooth that has been chipped, or a tooth that has been the subject of extensive previous dental work. Since the template tooth exists as a mathematical model, it can be displayed on the user interface and modified. The modification can be made using suitable navigation software and a clipping or erasing feature to delete part of the model. One way is providing a clipping plane feature, by which a plane intersects the template tooth in a orientation and location defined by the user using suitable navigation tools. The portion of the template tooth on one side of the plane is deleted. The user positions the plane at the desired location on the template tooth to roughly match the anatomical structure of the tooth in question. This process will result in a smooth execution of the tooth separation algorithm and result in a virtual tooth model that substantially exactly matches the structure of the patient's tooth.

The virtual tooth model may be extended beyond merely the crowns of the teeth. For example, a library of standardized virtual root templates for each of the teeth may be stored in the memory of the workstation. As individual virtual models of each tooth are created, the standardized root for that tooth are matched up with the virtual tooth model to thereby created an individual virtual tooth model of the entire tooth.

This process can be extended to templates of virtual gum tissue. On one hand, after separation of the individual virtual tooth models from the gum tissue the remaining portion of the scan data depicts the gum tissue (or at least a portion of the gum tissue, depending on the tissue scanned). This gum tissue may be substantially incomplete. The incomplete portions can be supplied by a template of virtual gum tissue, e.g., gums for an entire arch. The template of virtual gum tissue can be scaled up or down or modified as may be necessary to fit the anatomical structure of the patient. A registration of the template gum to the scanned gingival tissue enables a complete three-dimensional virtual model of the gums to be created.

This process can be extended to template bones, both mandible and maxilla. The goal here is to create a three-dimensional virtual model of the patient's mandible or maxilla. A virtual three-dimensional model of the mandible and maxilla can be obtained from a variety of sources, including CAT scan data, or skeletal specimens. The models are stored in the memory of the workstation. The virtual template mandible and maxilla are then expanded, contracted, or otherwise modified to fix to the patient's anatomy. X-rays of the patient may assist in the process. When the modified virtual template mandible and maxilla are created, the virtual teeth, gums and or roots can be displayed together with the maxilla or mandible, either alone or together with the orthodontic appliance.

The concept of template virtual objects can be extended to virtual template crowns, and the scanning features and user interface on the workstation extended to simulation of virtual crowns and adaptation of virtual crowns to virtual prepared teeth. For example, a prepared tooth is scanned as described herein and represented as a virtual three-dimensional model. A template virtual three-dimensional crown for the tooth (and typically for all 32 teeth) is stored in memory on the workstation or accessed from a database. The shape of the virtual template crown is reduced or adapted to form fit the prepared tooth where crown and prepared tooth surfaces meet. The shape of the cusps of the crown can be obtained from the surface configuration of the opposing tooth and adjacent teeth, or from the surface configuration of a contralateral tooth that is also scanned and represented a virtual tooth object.

Once the crown shape has been arrived at on the workstation, it can be exported as a 3-D crown object file to a remote location such as a lab for manufacture of the crown. For example, the 3-D crown object file is fed to a stereolithography machine and a physical model of the crown is made. A mold is made from the physical model. The crown is formed in the mold from gold or porcelain made using the lost wax technique. Alternatively, the 3D crown object file can be supplied to a CNC milling machine for machining a crown. Such crowns could be made from any suitable ceramic or metallic material, including stainless steel. This process represents a substantial savings of time and labor in manufacturing crowns. The typical crown preparation process is a manual process.

The concept of virtual template tooth objects and user manipulation of tooth objects on a computer can also be used in the field of dentures. Traditionally, an impression is taken of the gums and associated bony alveolar structures and these anatomical structures are cast in plastic or wax. Pre-formed teeth are set into the wax in a desired occlusion. The dentures are cast in acrylic using the lost wax technique. This process can be automated using the scanning methods described herein and using virtual three-dimensional template teeth. First, the gums and associated anatomical structures are scanned and represented as a three-dimensional virtual model on the workstation. Then, virtual template teeth are retrieved from memory. The template teeth are sized up or down as necessary to conform to the archform represented by the virtual model of the gums. The virtual template teeth are then placed on the archform. At this point, a three-dimensional virtual model of the teeth, gums and associated anatomical structures is represented in the workstation memory as a three-dimensional virtual object. This digital object can be exported anywhere, such as to a remote location where dentures are manufactured. From this object, a denture can be manufactured from a variety of techniques, including milling and casting. For example, a stereolithographic physical model of the dentition and/or gums can be made and a denture cast in a mold obtained from the physical model using the lost wax technique.

The virtual template teeth can also be used in forensic dentistry, i.e., reconstruction of the identity of a victim from teeth. As an example, a jaw containing some teeth can be scanned as described above and represented as a three-dimensional virtual object. Missing teeth can be reconstructed by importing virtual template teeth and placing them on the virtual object. The virtual template teeth may be based on age or ethnicity if such information is known. Contra-lateral teeth can be constructed by using existing scanned teeth as the template tooth and placing the scanned tooth in the contralateral position. Eventually, a complete virtual representation of the dentition can be obtained and viewed on the workstation. The shape of the face of the victim can be reconstructed by adding template virtual objects comprising soft tissue, gums, lips, cheeks, skin, hair, etc., and modifying the template objects using navigational tools based on the three-dimensional object or other information known about the victim.

Another example of using template teeth is for purposes of diagnosis and detection of tooth wearing, e.g., due to bruxism. In this example, the original scan taken of the patient is converted into a three-dimensional virtual model. The individual teeth are optically separated into virtual three-dimensional tooth objects as described above. Either this original virtual model of the entire dentition or the set of virtual three-dimensional tooth objects can be considered as a template. Over the course of time, the dentition is scanned again periodically and converted into a three-dimensional virtual model as described above. The individual teeth (or the dentition as a whole) is compared to the template to identify differences due to wearing of teeth. This can be performed by overlaying the two models, each in a different color or tones, and visually detecting where tooth surfaces were present initially but are not present in the current virtual model. Alternatively, measuring tools can be provided on the user interface to measure the height of the tooth or other distances that may be indicative of wear, and numerical values immediately presented to the user on the user interface. These measurements can be compared with measurements made of the template. Now, tooth wear can be quantified precisely.

As yet another possibility, individual tooth objects are obtained from the original scan of the patient. These tooth objects are stored in the memory. In the case of a loss of the patient's tooth due to an accident or due to an extraction, the virtual tooth objects provide a precise template for manufacture of a replacement tooth. The replacement tooth could be manufactured for example using the stereolithograpy and lost wax techniques referred to above.

The creation of virtual tooth models allows virtual brackets to be virtually bonded to individual virtual teeth. The virtual brackets are obtained from a 3D CAD model of the bracket obtained from the manufacturer of the bracket. Alternatively, the brackets could be scanned and virtual bracket models obtained from registration of the scan frames into a virtual three dimensional model of the bracket. In either event, the virtual brackets are stored in memory and later accessed from the user interface of the orthodontic workstation. For example, the virtual brackets are placed on the teeth at the location of the landmarks and then moved by the user accessing suitable navigational tools provided by the user interface.

The virtual bonding of the brackets is merely a superposition of the virtual bracket onto the virtual surface of the tooth. Since both the bracket and the tooth are separate and independent virtual objects, they can be moved freely relative to each other, for example to optimize the position of the bracket. Preferably, the treatment planning software allows the user to interactively position the brackets along any combination of X, Y and Z directions, as wells as rotation about three orthogonal rotational axes. In one possible embodiment, the bracket placement correction is made by the user performing the following steps:

1) navigating through the treatment planning software until the virtual model of the dentition and the virtual brackets are displayed (this can be either the target situation or the malocclusion);
2) selecting a bracket for movement by either clicking on the bracket or selecting a bracket number from a drop-down menu;
3) accessing navigational controls for the bracket, such as by clicking on an icon that displays navigational controls for moving virtual objects such as brackets;
4) allowing the user to select either move the teeth with the bracket or move the bracket freely in three dimensions; and
5) using the navigational controls to move the brackets in three dimensions as desired.

If the bracket is moved independent of the tooth model, when the user is finished with the movement of the bracket the virtual tooth is moved to the location of the bracket. Bonding corrections for bonding the bracket to the tooth are updated. The bracket is then virtually bonded to the tooth. This process can be performed for each tooth. The result is that the orthodontist customized the placement of virtual brackets to the teeth. The archwire, which passes through the bracket slots, will have the required bends to move the teeth to the desired target situation regardless of the positioning of the brackets on the teeth.

The combination of the displayed set of virtual orthodontic brackets, together with the virtual orthodontic archwire, thus presents to the user a customized virtual orthodontic appliance. The virtue of the customized virtual orthodontic appliance is that it can be studied, modified, shared between two computers, and transported electronically over a communications medium for fabrication of the orthodontic appliance. The treatment planning software is essentially a specialized CAD/CAM system that allows the design of virtually any configuration of tooth objects, bracket objects, wire objects and other appliances and objects. Because these objects exist as independent mathematical objects, they can be selectively displayed together or alone. For example, the treatment planning software displays an icon or button on the user interface that allows the user to select or deselect the teeth, wires, brackets or virtual objects or appliances, as desired. For example, the teeth and archwire can be displayed together with the brackets deleted from the user interface. The orthodontist can then select an individual tooth object, move it in three dimensions, and the movement of the tooth carried over to a repositioning of the bracket in three dimensions and a changing of the shape of the archwire.

Furthermore, while the above process of creation of tooth models has been described in conjunction with the scan data from the hand-held scanner, this is not required. The separation of tooth objects can be performed with any three-dimensional model of the teeth, regardless of how the three-dimensional model is obtained. The three-dimensional model could be acquired from a CT scan, a laser scan from a plaster impression, or otherwise.

Part 4. Introduction to Treatment Planning

The virtual model of the patient's dentition, and the individual tooth objects created as explained above, provide a base for diagnostic analysis of the dentition and treatment planning. Treatment planning is not particularly relevant to the scanning and calibration inventions provided herein, and so only an introduction will be given here. For further details, refer to the application of Rüdger Rubbert et al. filed contemporaneously, Ser. No. 11/285,629, entitled INTERACTIVE AND ARCHWIRE-BASED ORTHODONTIC CARE SYSTEM BASED ON INTRA-ORAL SCANNING OF TEETH, Ser. No. 11/285,629.

A bite registration scan is obtained from the patient to spatially correlate the scans of the upper and lower jaws when the dentition is clenched. This scan is used to provide a registration of the upper and lower jaw to determine the correct relative position. This bite registration scan is usually needed at the beginning of treatment to set the relation between the upper and lower jaws.

Landmarks such as shown in FIG. 57 are then placed on the labial surfaces of all the teeth. The illustrated embodiment places landmarks manually, but this process could be automated. The landmarks are placed initially on the molars and the front teeth, and an estimated position for the landmarks on the other teeth can be made, such as in the same plane, based on the relative position of the landmark with respect to the gingival tissue and incisal edge of the tooth, or other factors.

The landmarks are placed at the location where the orthodontist expects to place an orthodontic bracket to correct the malocclusion. The bracket shape is shown on the monitor 30 (FIG. 1). Three-dimensional templates for a variety of commercially available brackets are stored in memory and the software asks the orthodontist to select a particular manufacturer and style of bracket to use with the patient. Thus, as the landmarks are placed, virtual brackets appear in the computer model on the labial surfaces of the teeth where the orthodontist desires to place the brackets. The orthodontist can move the bracket position depending on the type of forces the orthodontist wishes to create on teeth to correct the malocclusion.

Figure 60:
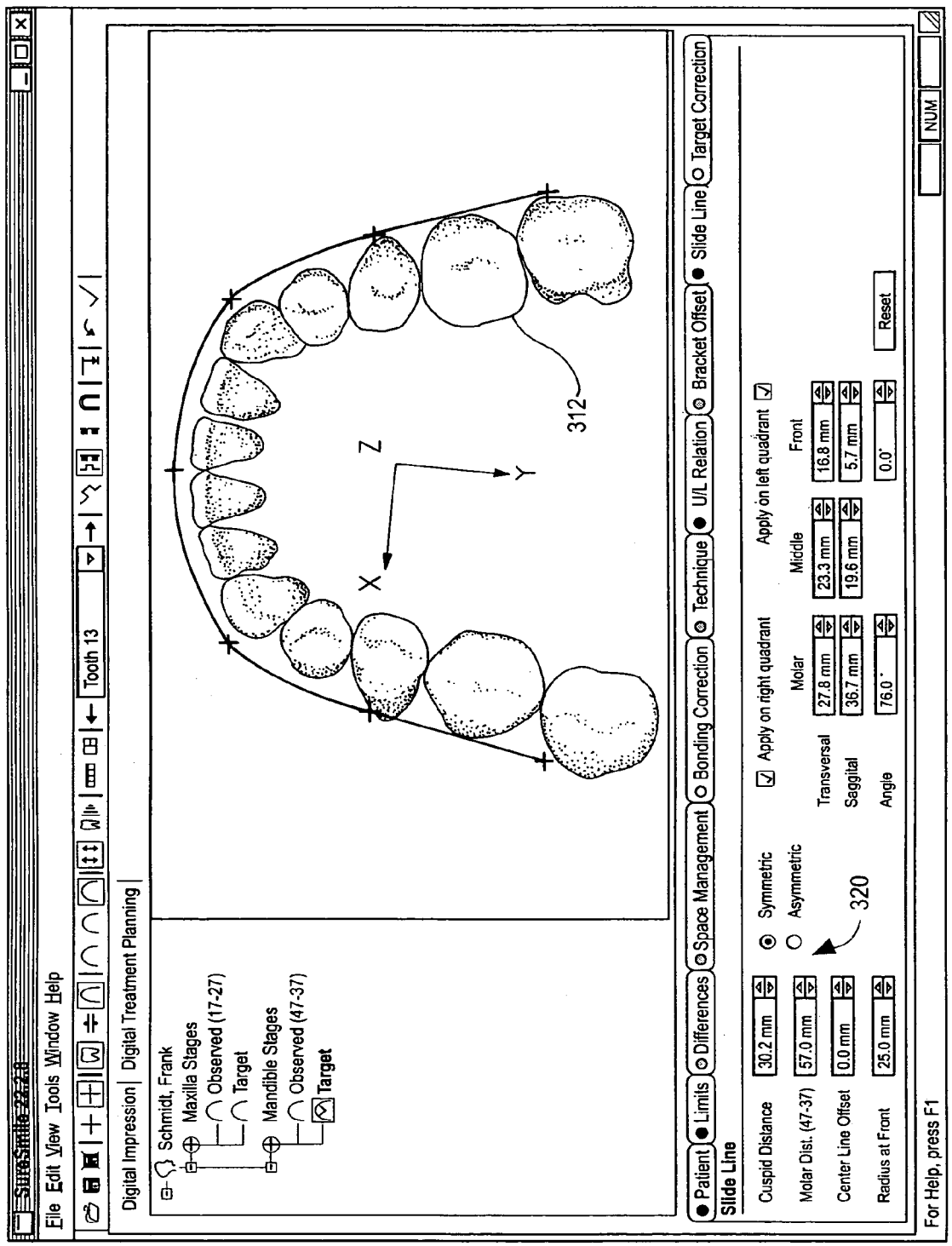
FIG. 60 is a screen shot from an orthodontic workstation showing the computer model of the patient's teeth positioned in a target or desired condition, as a result of the user selecting an archform for the patient and the computer placing the teeth along the arch selected by the user.
Figure 61:
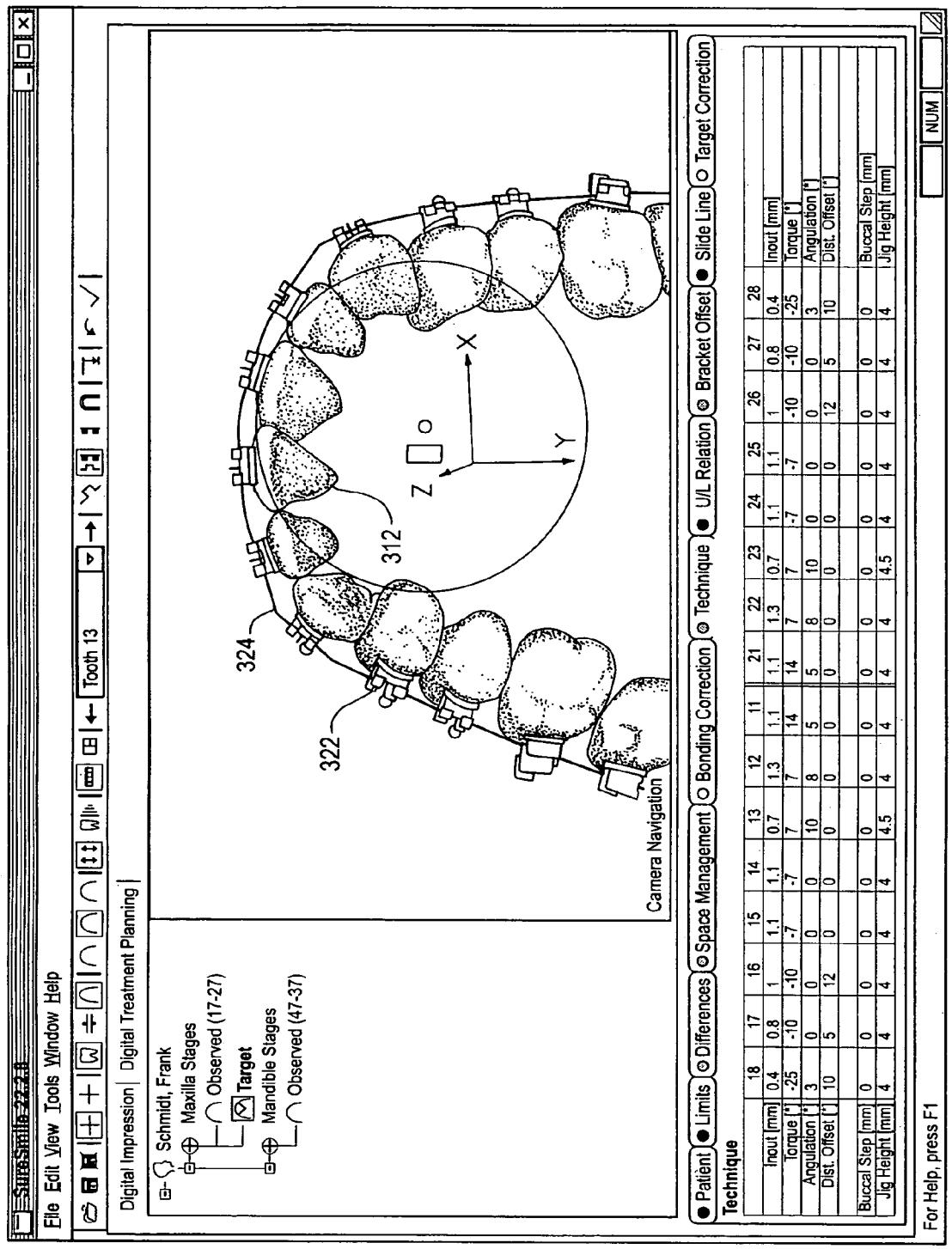
FIG. 61 is another screen shot showing the computer model of the patient's teeth in a target situation, also showing the numerous parameters available to the orthodontist to customize the tooth position, orientation, angulation, torque, and other parameters on a tooth by tooth basis for the target archform.

FIG. 60 is a screen shot from an orthodontic workstation showing the computer model of the patient's teeth objects 312 positioned in a target or desired condition. The illustration is the result of the user selecting an archform for the patient from a known type of archform (e.g., Roth), and the computer placing the teeth along the arch selected by the user. This is executed by placing the virtual brackets the orthodontist placed on the teeth along the curve selected by the orthodontist. The brackets are omitted from FIG. 60, but are shown in FIG. 61. The software allows the orthodontist to change many variables in the target situation, simply by entering new values in the slide line area 320 of the screen display, by mouse operation of up and down arrows to scroll through available values, or by mouse operation of a bar to change the values, or other similar technique. FIG. 60 shows some of the parameters by which the orthodontist can adjust the shape of the arch, the distance between the teeth, the distance between the molars, and other parameters, so as to provide a unique and customized target situation for the patient.

FIG. 61 is another screen shot showing the computer model of the patient's teeth in a target situation, also showing the numerous parameters available to the orthodontist to customize the tooth position, orientation, angulation, torque, and other parameters on a tooth by tooth basis for the target archform. Virtual brackets 322 are positioned on the tooth objects 312 at the location where the user placed the landmarks. A virtual archwire 324 passes through the slots in each virtual bracket.

Figure 62:
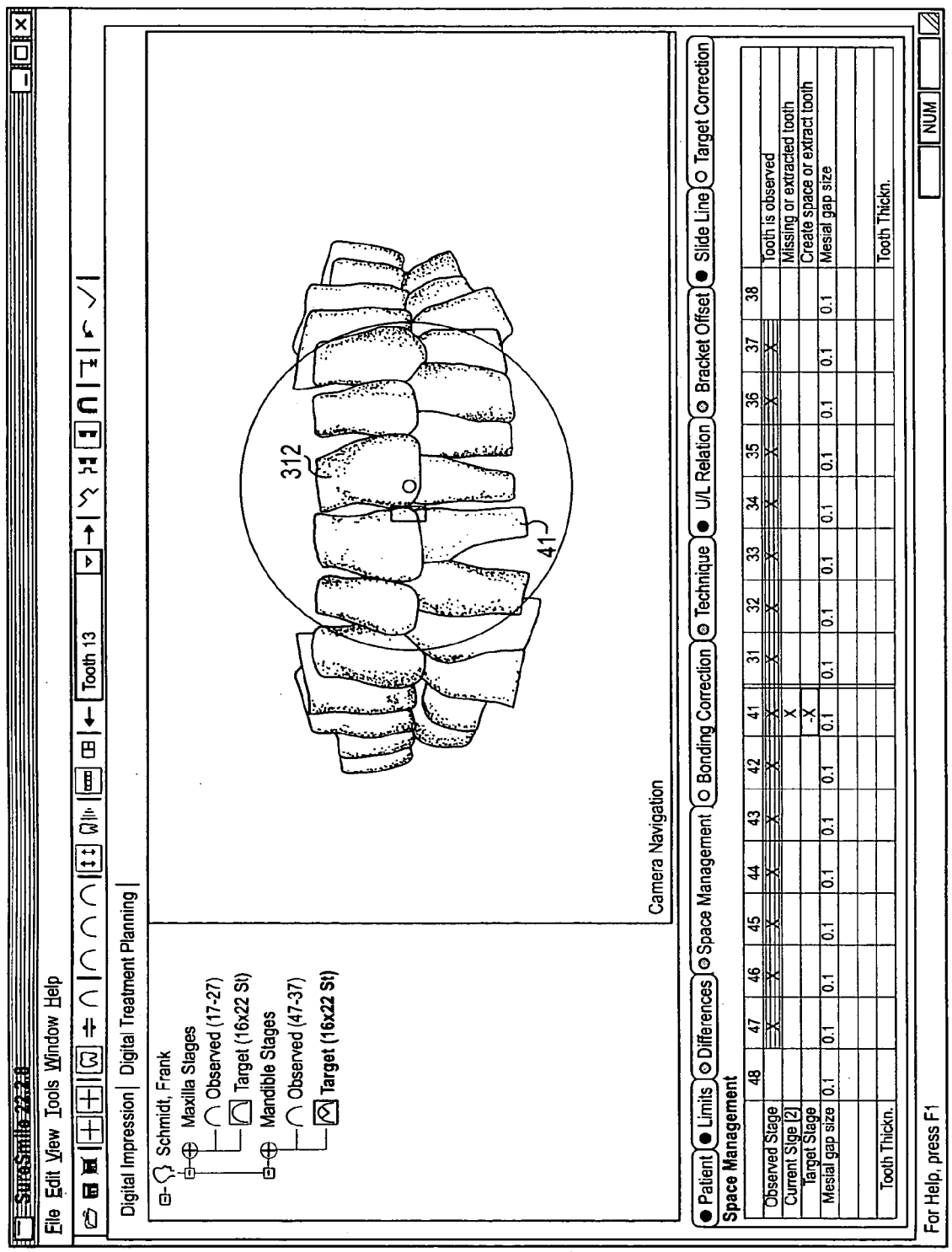
FIG. 62 is another screen shot showing a front view of the target situation and additional parameters available to the orthodontist for moving teeth relative to each other in planning treatment for the patient.

FIG. 62 is another screen shot showing a front view of the target situation and additional parameters available to the orthodontist for simulating the movement and positioning of teeth relative to each other in planning treatment for the patient. For example, in FIG. 62, the cursor is moved onto the virtual tooth 41 (in the tooth numbering convention) and the mouse is clicked. Tooth 41 is then highlighted. If the orthodontist wants to extract that tooth, they then click on the box 22 to extract the tooth in the simulation. Alternatively, tooth 41 could be rotated about any of three axis of rotation, moved in the X, Y or Z direction, or a larger or smaller gap could be created between teeth.

Figure 63:
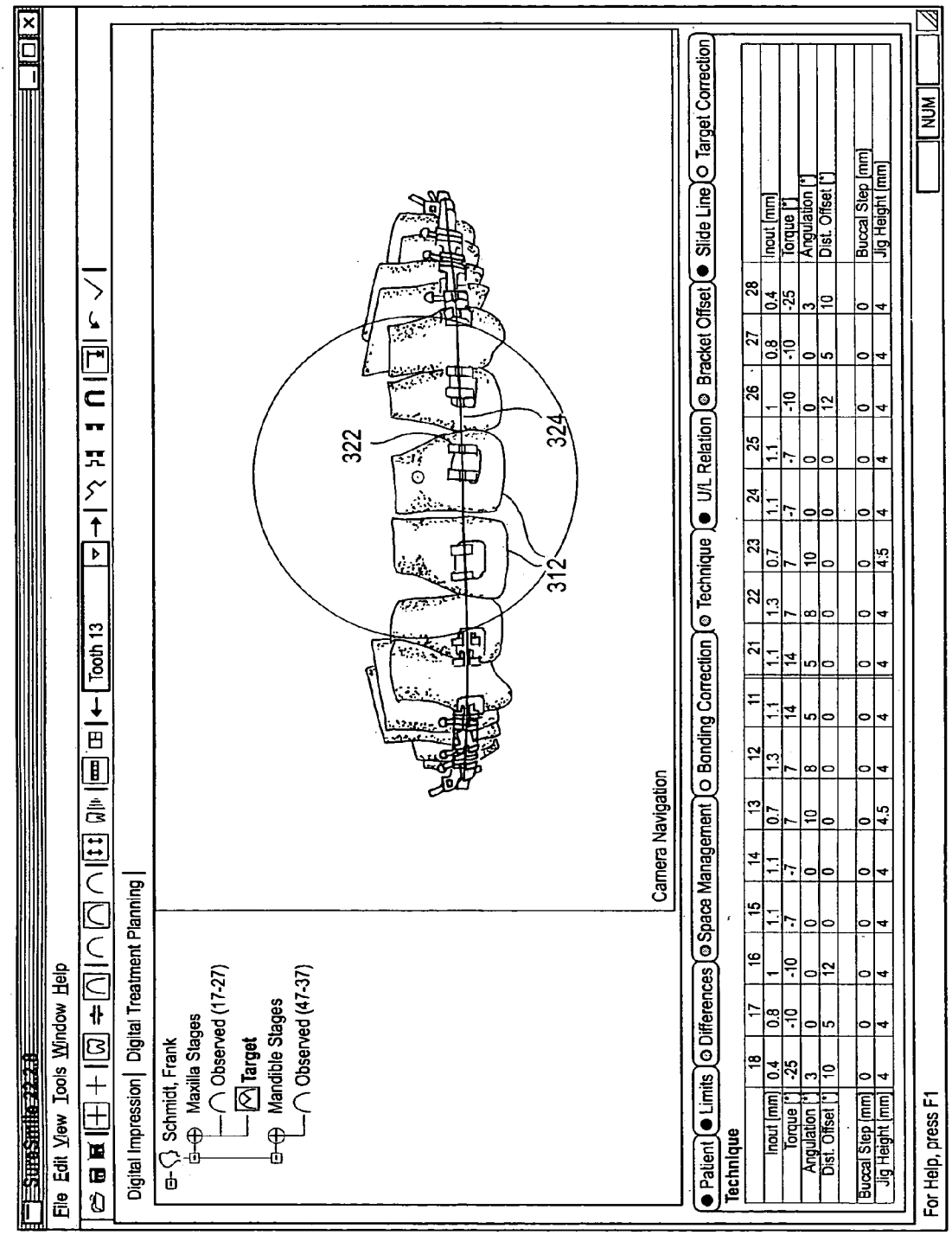
FIG. 63 is a screen shot of a target situation for the patient showing the virtual tooth in a target position, a set of virtual brackets placed on the teeth, and a virtual archwire.

FIG. 63 shows the target situation for the upper arch, with the virtual brackets 322 in place. The orthodontist can adjust the bracket 322 position, archwire shape 324, or tooth 312 position, on a tooth by tooth basis to thereby optimize treatment planning for the patient.

The result of the treatment planning is the generation of a set of bracket placement positions and the display on the monitor of the shape of a customized orthodontic archwire to treat the malocclusion. Information as to the location of the brackets, the three-dimensional model of the malocclusion, the three dimensional model of the target situation, and the type of archwire to use are sent to the precision appliance center 26 of FIG. 1. A customized orthodontic archwire is manufactured in accordance with the bracket location and type and the target situation for the patient. Additionally, a transfer tray is manufactured to assist the orthodontist to place the brackets at the proper location. The transfer tray, brackets and archwire are shipped to the orthodontist's clinic 22. The orthodontic appliance is then applied to the patient and treatment commences.

Because the hand-held scanner allows for scans of the dentition in a matter of minutes, the scanner becomes an important tool in monitoring treatment. As the treatment progresses, the movement and position of the teeth during treatment can be quantified with a high degree of precision. The orthodontist can discern during treatment that corrections in the wire need to be made, for example due to biological influences affecting tooth movement. The treatment planning software on the workstation displays the current situation, and also the target situation. A new customized archwire is designed on the computer. The relevant information for making the new archwire is sent to the precision appliance service center and a new archwire is manufactured and shipped to the clinic.

Monitoring scans are taken during treatment to measure and quantify progress and detect deviations from the expected treatment. Since each of the tooth objects is already stored, the monitoring scan need not be of the entire dentition, but rather needs to only be of one surface, such as the occlusal surface, or the lingual surface, or some combination of the two. A bite scan with the teeth in a clenched condition is also taken to get the current upper and lower relation. The position of the rest of the teeth is obtained from the virtual tooth objects 312 of the patient's teeth (FIG. 58F). After the monitoring scans are performed, a registration is performed of the scanned data relative to the tooth models to complete the teeth and derive a current virtual model of the patient at that point in treatment. Study of this virtual model and comparison to the target virtual model of the teeth and the virtual model at the beginning of treatment can indicate whether progress is as anticipated or if additional correction to the orthodontic appliance need to be made. These corrections will typically be carried out as wire changes in an archwire orthodontic treatment regime, in which new bends are placed in the orthodontic archwire.

Other Uses of Scanner

It is contemplated that the inventive scanning system and method of scanning can be used on virtually any type of object. The medical field is only one example of where three-dimensional information of a surface may be a valuable piece of information, and can be easily and quickly attained with the scanning system of the present invention. These other possible uses of the scanner for other types of objects are considered within the scope of the invention.

Precise three dimensional information of an object may be useful in the world of art as a way of authenticating a painting or sculpture. The work, or perhaps some portion of the work, is scanned. A registration is performed of the scanned images to create a complete three-dimensional model of the work. The model is archived or stored in memory, for example in a computer of a museum or gallery owning the work. Any work purporting to be that work of art that should later appear on the art market (e.g., if the work is lost or stolen), can be verified by scanning the work or the portion of the work. Then, a comparison of the three-dimensional model of the original work to the three-dimensional model of the work purporting to be the work can be made. Any substantial deviation from the original to the purported work will reveal the purported original to be a forgery. Thus, in another aspect of the invention, a machine-readable memory is provided that is accessible by a computing device. The memory comprises data storage regions storing surface information in three dimensions of at least a portion of a work of art. The surface information is obtained by scanning the work of art with a scanner and calculating the surface information in three dimensions from a series of images obtained by the scanner.

Furthermore, a memory may be created storing three-dimensional models of a large number of works, for example the works in the Museum of Modern Art in New York City. This archive can be used for authentication of any work of art that may be stolen or lost from the museum and later recovered.

The capability of the scanning system to store or archive accurate three dimensional models of objects can be a powerful tool in a variety of fields, including archeology, paleontology, forensic science, historic preservation and architecture, and other industrial or medical areas. As noted above, the scanner optics will be designed to have the proper range of focus and angle between projection and imaging axes to record images of these types of objects. The principles of operation of the scanner are applicable to all of these potential uses of the invention.

While a presently preferred embodiment of the invention has been described with particularity, variation from the illustrated embodiment is possible without departure from the scope of the invention. This scope is to be determined by reference to the appended claims.

The invention claimed is:

1. A method of registering a first frame, representing a first set of three-dimensional coordinates of points on the surface of an object, relative to second frame, representing a second set of three-dimensional coordinates of points on the surface of the object, comprising the steps of:

storing said sets of three-dimensional coordinates of points in a machine-readable memory;

processing said sets of three-dimensional coordinates with a data processing unit reading said machine-readable memory, said step of processing comprising the steps of:

a) determining $\Delta X$, $\Delta Y$ and $\Delta Z$ offsets between overlapping points in said frames;

b) changing the coordinates in second frame in accordance with said $\Delta X$, $\Delta Y$ and $\Delta Z$ offsets;

c) computing a surface for said first frame from points in said first frame;

d) computing normal vectors from said points in said second frame to said surface and a net normal vector;

e) determining X, Y and Z components of a rotation matrix from said surface and said points in said second frame, said rotation matrix indicting the amount of rotation required to fit said second frame to said first frame; and f) applying said net normal vector and said rotation matrix to said points in said second frame to thereby generate a new set of coordinates of said second frame in three dimensions to fit of said second frame to said first frame.

2. The method of claim 1, further comprising the following steps:

g) determining the closeness of said fit of said second frame to said first frame;

h) comparing said closeness to a quality index; and i) repeating steps at least steps c), d), e) and f) for said second frame, after application of step f), to said first frame.

3. The method of claim 2, wherein steps c)–i) are repeated numerous times until said closeness in step h) is less than or equal to said quality index.

4. The method of claim 1, wherein said first frame comprises a set of coordinates of said object arrived at after a cumulative registration of a set of frames of said object.

5. The method of claim 1, wherein said first frame comprises at least two frames previously registered with respect to each other.

6. The method claim 1, wherein said method is performed while a scanning system captures a plurality of images of the object, said scanning system comprising an electronic imaging device generating a stream of images and supplying said images to said memory.

7. The method of claim 6, wherein said scanning system includes said memory and said data processing unit, and wherein said scanning system further comprises a user interface including a display, and wherein the results of fitting said second frame to said first frame are displayed on said display while said scanning system is capturing said plurality of images, enabling the operator of said scanning system to see the results of scanning the object.

8. The method of claim 7, wherein said object comprises a human.

9. The method of claim 8, wherein said object comprises teeth and associated anatomical structures.

10. The method of claim 8, wherein said scanning system comprises a hand-held scanner.

11. The method of claim 1, wherein in step (a) a two dimensional cross-correlation is performed by said data processing unit on first and second images corresponding to said first and second frames to determine said $\Delta X$ and $\Delta Y$ offsets.

12. The method of claim 1, wherein in step (a) said $\Delta Z$ offset is determined by computing an average Z value for said first frame and an average Z value of said second frame and computing said $\Delta Z$ offset from said averages.

* * * * *